US007589116B2

(12) United States Patent
Chakravarty et al.

(10) Patent No.: US 7,589,116 B2
(45) Date of Patent: *Sep. 15, 2009

(54) BIARYL SUBSTITUTED PYRAZOLES AS SODIUM CHANNEL BLOCKERS

(75) Inventors: Prasun K. Chakravarty, Edison, NJ (US); Michael H. Fisher, Ringoes, NJ (US); Jeffrey M. Fisher, legal representative, Ringoes, NJ (US); William H. Parsons, Belle Mead, NJ (US); Sriram Tyagarajan, Edison, NJ (US); Bishan Zhou, Edison, NJ (US)

(73) Assignee: Merck & Co. Inc., Rahway, NJ (US)

( * ) Notice: Subject to any disclaimer, the term of this patent is extended or adjusted under 35 U.S.C. 154(b) by 534 days.

This patent is subject to a terminal disclaimer.

(21) Appl. No.: 10/552,024

(22) PCT Filed: Mar. 30, 2004

(86) PCT No.: PCT/US2004/009713

§ 371 (c)(1),
(2), (4) Date: Oct. 3, 2005

(87) PCT Pub. No.: WO2004/092140

PCT Pub. Date: Oct. 28, 2004

(65) Prior Publication Data

US 2006/0183785 A1  Aug. 17, 2006

Related U.S. Application Data

(60) Provisional application No. 60/460,106, filed on Apr. 3, 2003.

(51) Int. Cl.
*A61K 31/415* (2006.01)
*C07D 231/00* (2006.01)
(52) U.S. Cl. .................................. 514/403; 548/356.1
(58) Field of Classification Search .................. 514/403; 548/356.1
See application file for complete search history.

(56) References Cited

U.S. PATENT DOCUMENTS 6,100,259 A * 8/2000 Xiang et al. ............. 514/236.5
2005/0153986 A1  7/2005 Chen et al.
2006/0194807 A1 * 8/2006 Cosford et al. ............ 514/250

FOREIGN PATENT DOCUMENTS

| JP | 2001/315387 | 11/2001 |
|---|---|---|
| JP | 2001/335574 | 12/2001 |
| JP | 2002 365289 | 12/2002 |
| WO | WO 96/01254 | 1/1996 |
| WO | WO 97/01551 | 1/1997 |
| WO | WO 98/31227 | 7/1998 |
| WO | WO 01/68612 | 9/2001 |
| WO | WO 02/066462 | 8/2002 |
| WO | WO 03/055860 | 7/2003 |
| WO | WO 03/062206 | 7/2003 |
| WO | WO 2004/016606 | 2/2004 |
| WO | WO 2004/060305 | 7/2004 |
| WO | WO 2004/069158 | 8/2004 |

OTHER PUBLICATIONS

Patani, et al., Bioisosterism, Chem. Rev., 1996, 96, pp. 3147-3176, especially p. 3149.*
Finar et al., Journal of the Chemical Society, Section B: Physical Organic, vol. 2, pp. 211-214, 1968.*
Finar, I.L., Journal of the Chemical Society, Section B: Physical Organic, vol. 7, pp. 725-732, 1968.*
Finar, et al., Journal of the Chemical Society, Section B: Physical Organic, vol. 2, pp. 211-214, 1968.*
Finar et al., J. Chem. Soc., Sec. B: Phys. Org., vol. 2, pp. 211-214, 1968.*
S. Portnoy, "Fluorinated Nitrogen Heterocycles via Cyclization. III. 3-Trifluoromethyl-1-(4-trifluoromethyl-2-pyridyl)-pyrazoles from Fluorinated 1,3-Diketones and 4-Trifluoromethyl-2-hydrazinopyridines", 1969, vol. 6, pp. 223-228, J. Het. Chem.

* cited by examiner

*Primary Examiner*—Golam M. M. Shameem
*Assistant Examiner*—Susannah Chung
(74) *Attorney, Agent, or Firm*—Sylvia A. Ayler; William Krovatin

(57) ABSTRACT

Biaryl substituted pyrazole compounds are sodium channel blockers useful for the treatment of pain and other conditions. Pharmaceutical compositions comprise an effective amount of the instant compounds, either alone, or in combination with one or more therapeutically active compounds, and a pharmaceutically acceptable carrier. Methods of treatment of conditions, including acute pain, chronic pain, visceral pain, inflammatory pain, and neuropathic pain, comprise administering an effective amount of the present compounds, either alone, or in combination with one or more therapeutically active compounds.

31 Claims, No Drawings

BIARYL SUBSTITUTED PYRAZOLES AS SODIUM CHANNEL BLOCKERS

RELATED APPLICATION DATA

This is a National filing under 35 USC 371 of PCT/US2004/009713, filed Mar. 30, 2004, which claims priority from U.S. Ser. No. 60/460,106, filed Apr. 3, 2003.

FIELD OF THE INVENTION

The present invention is directed to a series of biaryl substituted pyrazole compounds. In particular, this invention is directed to biaryl substituted pyrazole compounds that are sodium channel blockers useful for the treatment of chronic and neuropathic pain. The compounds of the present invention are also useful for the treatment of other conditions, including, for example, central nervous system (CNS) disorders such as epilepsy, manic depression, bipolar disorder, depression, anxiety and diabetic neuropathy.

BACKGROUND OF THE INVENTION

Voltage-gated ion channels allow electrically excitable cells to generate and propagate action potentials and therefore are crucial for nerve and muscle function. Sodium channels play a special role by mediating rapid depolarization, which constitutes the rising phase of the action potential and in turn activates voltage-gated calcium and potassium channels. Voltage-gated sodium channels represent a multigene family. Nine sodium channel subtypes have been cloned and functionally expressed to date. [Clare, J. J., Tate, S. N., Nobbs, M. & Romanos, M. A. Voltage-gated sodium channels as therapeutic targets. *Drug Discovery Today* 5, 506-520 (2000)]. They are differentially expressed throughout muscle and nerve tissues and show distinct biophysical properties. All voltage-gated sodium channels are characterized by a high degree of selectivity for sodium over other ions and by their voltage-dependent gating. [Catterall, W. A. Structure and function of voltage-gated sodium and calcium channels. *Current Opinion in Neurobiology* 1, 5-13 (1991)]. At negative or hyperpolarized membrane potentials, sodium channels are closed. Following membrane depolarization, sodium channels open rapidly and then inactivate. Sodium channels only conduct currents in the open state and, once inactivated, have to return to the resting state, favored by membrane hyperpolarization, before they can reopen. Different sodium channel subtypes vary in the voltage range over which they activate and inactivate as well as in their activation and inactivation kinetics.

Sodium channels are the target of a diverse array of pharmacological agents, including neurotoxins, antiarrhythmics, anticonvulsants and local anesthetics. [Clare, J. J., Tate, S. N., Nobbs, M. & Romanos, M. A. Voltage-gated sodium channels as therapeutic targets. *Drug Discovery Today* 5, 506-520 (2000)]. Several regions in the sodium channel secondary structure are involved in interactions with these blockers and most are highly conserved. Indeed, most sodium channel blockers known to date interact with similar potency with all channel subtypes. Nevertheless, it has been possible to produce sodium channel blockers with therapeutic selectivity and a sufficient therapeutic window for the treatment of epilepsy (e.g. lamotrigine, phenytoin and carbamazepine) and certain cardiac arrhythmias (e.g. lignocaine, tocainide and mexiletine).

It is well known that the voltage-gated Na+ channels in nerves play a critical role in neuropathic pain. Injuries of the peripheral nervous system often result in neuropathic pain persisting long after the initial injury resolves. Examples of neuropathic pain include, but are not limited to, postherpetic neuralgia, trigeminal neuralgia, diabetic neuropathy, chronic lower back pain, phantom limb pain, pain resulting from cancer and chemotherapy, chronic pelvic pain, complex regional pain syndrome and related neuralgias. It has been shown in human patients as well as in animal models of neuropathic pain, that damage to primary afferent sensory neurons can lead to neuroma formation and spontaneous activity, as well as evoked activity in response to normally innocuous stimuli. [Carter, G. T. and B. S. Galer, *Advances in the management of neuropathic pain*. Physical Medicine and Rehabilitation Clinics of North America, 2001. 12(2): p. 447-459]. The ectopic activity of normally silent sensory neurons is thought to contribute to the generation and maintenance of neuropathic pain. Neuropathic pain is generally assumed to be associated with an increase in sodium channel activity in the injured nerve. [Baker, M. D. and J. N. Wood, *Involvement of Na channels in pain pathways*. TRENDS in Pharmacological Sciences, 2001. 22(1): p. 27-31].

Indeed, in rat models of peripheral nerve injury, ectopic activity in the injured nerve corresponds to the behavioral signs of pain. In these models, intravenous application of the sodium channel blocker and local anesthetic lidocaine can suppress the ectopic activity and reverse the tactile allodynia at concentrations that do not affect general behavior and motor function. [Mao, J. and L. L. Chen, Systemic lidocaine for neuropathic pain relief. Pain, 2000. 87: p. 7-17]. These effective concentrations were similar to concentrations shown to be clinically efficacious in humans. [Tanelian, D. L. and W. G. Brose, *Neuropathic pain can be relieved by drugs that are use-dependent sodium channel blockers: lidocaine, carbamazepine and mexiletine*. Anesthesiology, 1991. 74(5): p. 949-951]. In a placebo-controlled study, continuous infusion of lidocaine caused reduced pain scores in patients with peripheral nerve injury, and in a separate study, intravenous lidocaine reduced pain intensity associated with postherpetic neuralgia (PEN). [Mao, J. and L. L. Chen, *Systemic lidocaine for neuropathic pain relief*. Pain, 2000. 87: p. 7-17. Anger, T., et al., *Medicinal chemistry of neuronal voltage-gated sodium channel blockers*. Journal of Medicinal Chemistry, 2001. 44(2): p. 115-137]. Lidoderm®, lidocaine applied in the form of a dermal patch, is currently the only FDA approved treatment for PHN. [Devers, A. and B. S. Galer, *Topical lidocaine patch relieves a variety of neuropathic pain conditions: an open-label study*. Clinical Journal of Pain, 2000. 16(3): p. 205-208].

In addition to neuropathic pain, sodium channel blockers have clinical uses in the treatment of epilepsy and cardiac arrhythmias. Recent evidence from animal models suggests that sodium channel blockers may also be useful for neuroprotection under ischaemic conditions caused by stroke or neural trauma and in patients with multiple sclerosis (MS). [Clare, J. J. et. al. And Anger, T. et. al.].

International Patent Publication WO 00/57877 describes aryl substituted pyrazoles, imidazoles, oxazoles, thiazoles, and pyrroles and their uses as sodium channel blockers. International Patent Publication WO 01/68612 describes aryl substituted pyridines, pyrimidines, pyrazines and triazines and their uses as sodium channel blockers. International Patent Publication WO 99/32462 describes triazine compounds for the treatment for CNS disorders. However, there remains a need for novel compounds and compositions that therapeutically block neuronal sodium channels with less side effects and higher potency than currently known compounds.

SUMMARY OF THE INVENTION

The present invention is directed to biaryl pyrazole compounds which are sodium channel blockers useful for the treatment of chronic and neuropathic pain. The compounds of the present invention are also useful for the treatment of other conditions, including CNS disorders such as epilepsy, manic depression, anxiety, depression and bipolar disorder. This invention provides pharmaceutical compositions comprising a compound of the present invention, either alone, or in combination with one or more therapeutically active compounds, and a pharmaceutically acceptable carrier.

This invention further comprises methods for the treatment of conditions associated with, or resulting from, sodium channel activity, such as acute pain, chronic pain, visceral pain, inflammatory pain, neuropathic pain and disorders of the CNS including, but not limited to, epilepsy, manic depression, anxiety, depression and bipolar disorder.

DETAILED DESCRIPTION OF THE INVENTION

The compounds described in the present invention are represented by Formula (I), (II), (III) or (IV):

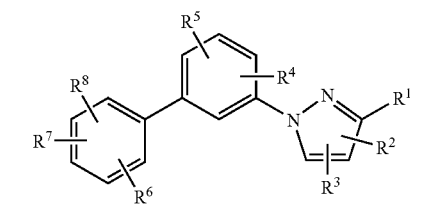
(I)

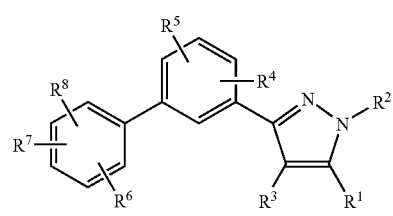
(II)

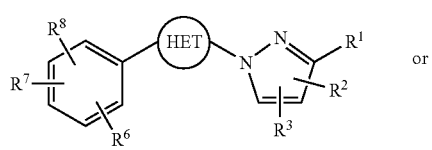
(III)

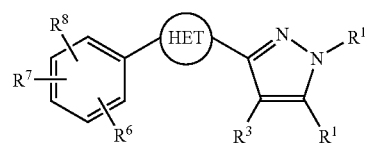
(IV)

or pharmaceutically acceptable salts thereof, wherein
HET is one of the following heterocycles:

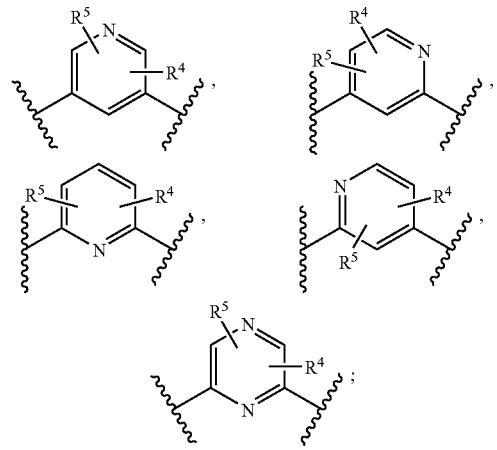

$R^1$ is
(a) H;
(b) $C_1$-$C_6$-alkyl, $C_2$-$C_4$-alkenyl, $C_2$-$C_4$-alkynyl, $C_3$-$C_6$-cycloalkyl, or $C_1$-$C_4$-alkyl-[$C_3$-$C_6$-cycloalkyl], any of which is optionally substituted with one or more of the following substituents: F, $CF_3$, OH, O—($C_1$-$C_4$)alkyl, $S(O)_{0-2}$—($C_1$-$C_4$)alkyl, O—$CONR^aR^b$, $NR^aR^b$, $N(R^a)CONR^aR^b$, COO—($C_1$-$C_4$)alkyl, COOH, CN, $CONR^aR^b$, $SO_2NR^aR^b$, $N(R^a)SO_2NR^aR^b$, —C(=NH)$NH_2$, tetrazolyl, triazolyl, imidazolyl, oxazolyl, oxadiazolyl, isooxazolyl, thiazolyl, furyl, thienyl, pyrazolyl, pyrrolyl, pyridyl, pyrimidinyl, pyrazinyl, phenyl, piperidinyl, morpholinyl, pyrrolidinyl or piperazinyl;
(c) —O—$C_1$-$C_6$-alkyl, —O—$C_3$-$C_6$-Cycloalkyl, —S—$C_1$-$C_6$-alkyl or —S—$C_3$-$C_6$-cycloalkyl, any of which is optionally substituted with one or more of the following substituents: F, $CF_3$, OH, O—($C_1$-$C_4$)alkyl, $S(O)_{0-2}$—($C_1$-$C_4$)alkyl, O—$CONR^aR^b$, $NR^aR^b$, $N(R^a)CONR^aR^b$, COO—($C_1$-$C_4$)alkyl, COOH, CN, $CONR^aR^b$, $SO_2NR^aR^b$, $N(R^a)SO_2NR^aR^b$, —C(=NH)$NH_2$, tetrazolyl, triazolyl, imidazolyl, oxazolyl, oxadiazolyl, isooxazolyl, thiazolyl, furyl, thienyl, pyrazolyl, pyrrolyl, pyridyl, pyrimidinyl, pyrazinyl, phenyl, piperidinyl, morpholinyl, pyrrolidinyl or piperazinyl;
(d) —$C_0$-$C_4$-alkyl-$C_1$-$C_4$-perfluoroalkyl, or —O-$C_0$-$C_4$-alkyl-$C_1$-$C_4$-perfluoroalkyl;
(e) —OH;
(f) —O-aryl, or —O—$C_1$-$C_4$-alkyl-aryl, wherein aryl is phenyl, pyridyl, pyrimidinyl, furyl, thienyl, pyrrolyl, triazolyl, pyrazolyl, thiazolyl, isoxazolyl, oxazolyl, or oxadiazolyl, any aryl of which is optionally substituted with 1-3 substituents selected from i) F, Cl, Br, I, ii) —CN, iii) —$NO_2$, iv) —C(=O)($R^a$), v) —$OR^a$, vi) —$NR^aR^b$, vii) —$C_{0-4}$alkyl-CO—$OR^a$, viii) —($C_{0-4}$alkyl)-NH—CO—$OR^a$, ix) —($C_{0-4}$alkyl)-CO—N($R^a$)($R^b$), x) —$S(O)_{0-2}R^a$, xi) —$SO_2N(R^a)(R^b)$, xii) —$NR^aSO_2R^a$, xiii) —$C_{1-10}$alkyl, and xiv) —$C_{1-10}$alkyl, wherein one or more of the alkyl carbons can be replaced by a —$NR^a$—, —O—, —$S(O)_{1-2}$—, —O—C(O)—, —C(O)—O—, —C(O)—N($R^a$)—, —N($R^a$)—C(O)—, —N($R^a$)—C(O)—N($R^a$)—, —C(O)—, —CH(OH)—, —C=C—, or —C≡C—;
(g) —OCON($R^a$)($R^b$), or —OSO$_2$N($R^a$)($R^b$);
(h) —SH, or —SCON($R^a$)($R^b$);
(i) $NO_2$;

(j) NR$^a$R$^b$, —N(COR$^a$)R$^b$, —N(SO$_2$R$^a$)R$^b$, —N(R$^a$)SO$_2$N(R$^a$)$_2$, —N(OR$^a$)CONR$^a$R$^b$, —N(R$^a$)SO$_2$R$^a$ or —N(R$^a$)CON(R$^a$)$_2$;

(k) —CH(OR$^a$)R$^a$, —C(OR$^b$)CF$_3$, —CH(NHR$^b$)R$^a$, —C(=O)R$^a$, C(=O)CF$_3$, —SOCH$_3$, —SO$_2$CH$_3$, COOR$^a$, CN, CONR$^a$R$^b$, —COCONR$^a$R$^b$, SO$_3$NR$^a$R$^b$, CH$_2$O—SO$_2$NR$^a$R$^b$, SO$_2$N(R$^a$)OR$^a$, —C(=NH)NH$_2$, —CR$^a$=N—OR$^a$, CH=CHCONR$^a$R$^b$;

(l) —CONR$^a$(CH$_2$)$_{0-2}$C(R$^a$)(R$^b$)(CH$_2$)$_{0-2}$CONR$^a$R$^b$;

(m) tetrazolyl, tetrazolinonyl, triazolyl, triazolinonyl, imidazolyl, imidozolonyl, oxazolyl, oxadiazolyl, isooxazolyl, thiazolyl, furyl, thienyl, pyrazolyl, pyrazolonyl, pyrrolyl, pyridyl, pyrimidinyl, pyrazinyl, or phenyl, any of which is optionally substituted with 1-3 substituents selected from i) F, Cl, Br, I, ii) —CN, iii) —NO$_2$, iv) —C(=O)R$^a$, v) C$_1$-C$_6$-alkyl, vi) —O—R$^a$, vii) —NR$^a$R$^b$, viii) —C$_0$-C$_4$-alkyl-CO —OR$^a$, ix) —(C$_0$-C$_4$-alkyl)-NH—CO—OR$^a$, x) —(C$_0$-C$_4$-alkyl)-CO—NR$^a$R$^b$, xi) —S(O)$_{0-2}$R$^a$, xii) —SO$_2$NR$^a$R$^b$, xiii) —NHSO$_2$R$^a$, xiv) —C$_1$-C$_4$-perfluoroalkyl, and xv) —O—C$_1$-C$_4$-perfluoroalkyl;

(n) —C(R$^a$)=C(R$^b$)—COOR$^a$, or —C(R$^a$)=C(R$^a$)—CONR$^a$R$^b$;

(o)

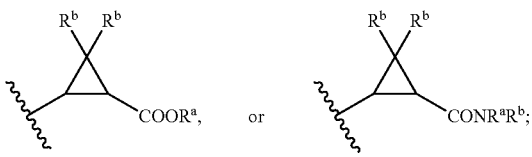

(p) piperidin-1-yl, morpholin-1-yl, pyrrolidin-1-yl, piperazin-1-yl or 4-susbstituted piperazin-1-yl, any of which is optionally substituted with 1-3 substituents selected from i) —CN, ii) —C(=O)(R$^a$), iii) C$_1$-C$_6$-alkyl, iv) —OR$^a$, v) —NR$^a$R$^b$, vi) —C$_0$-C$_4$-alkyl-CO—OR$^a$, vii) —(C$_0$-C$_4$-alkyl)-NH—CO—OR$^a$, viii) —(C$_0$-C$_4$-alkyl)-CON(R$^a$)(R$^b$), ix) —SR$^a$, x) —S(O)$_{0-2}$R$^a$, xi) —SO$_2$N(R$^a$)(R$^b$), xii) —NR$^a$SO$_2$R$^a$ xiii) —C$_1$-C$_4$-perfluoroalkyl and xiv) —O—C$_1$-C$_4$-perfluoroalkyl;

R$^a$ is
(a) H;
(b) C$_1$-C$_4$-alkyl, optionally substituted with one or more of the following substituents: F, CF$_3$, OH, O—(C$_1$-C$_4$)alkyl, S(O)$_{0-2}$—(C$_1$-C$_4$)alkyl, —OCONH$_2$, —OCONH(C$_1$-C$_4$alkyl), —OCON(C$_1$-C$_4$alkyl)(C$_1$-C$_4$alkyl), —OCONHC$_1$-C$_4$alkyl-aryl), —OCON(C$_1$-C$_4$alkyl)(C$_1$-C$_4$alkyl-aryl), NH$_2$, NH(C$_1$-C$_4$alkyl), N(C$_1$-C$_4$alkyl)(C$_1$-C$_4$alkyl), NH(C$_1$-C$_4$alkyl-aryl), N(C$_1$-C$_4$alkyl)(C$_1$-C$_4$alkyl-aryl), NHCONH$_2$, NHCONH(C$_1$-C$_4$alkyl), NHCONH(C$_1$-C$_4$alkyl-aryl), —NHCON(C$_1$-C$_4$alkyl)(C$_1$-C$_4$alkyl), NHCON(C$_1$-C$_4$alkyl)(C$_1$-C$_4$alkyl-aryl), N(C$_1$-C$_4$alkyl)CON(C$_1$-C$_4$alkyl)(C$_1$-C$_4$alkyl), N(C$_1$-C$_4$alkyl)CON(C$_1$-C$_4$alkyl)(C$_1$-C$_4$alkyl-aryl), COO—(C$_1$-C$_4$-alkyl), COOH, CN, CONH$_2$, CONH(C$_1$-C$_4$alkyl), CON(C$_1$-C$_4$alkyl)(C$_1$-C$_4$alkyl), SO$_2$NH$_2$, SO$_2$NH(C$_1$-C$_4$alkyl), SO$_2$NH(C$_1$-C$_4$alkyl-aryl), SO$_2$N(C$_1$-C$_4$alkyl)(C$_1$-C$_4$alkyl), NHSO$_2$NH$_2$, —C(=NH)NH$_2$, tetrazolyl, triazolyl, imidazolyl, oxazolyl, oxadiazolyl, isooxazolyl, thiazolyl, furyl, thienyl, pyrazolyl, pyrrolyl, pyridyl, pyrimidinyl, pyrazinyl, phenyl, piperidinyl, morpholinyl, pyrrolidinyl or piperazinyl;
(c) C$_0$-C$_4$-alkyl-(C$_1$-C$_4$)-perfluoroalkyl; or
(d) —C$_1$-C$_4$-alkyl-aryl, wherein aryl is phenyl, pyridyl, pyrimidinyl, furyl, thienyl, pyrrolyl, triazolyl, pyrazolyl, thiazolyl, isoxazolyl, oxazolyl, or oxadiazolyl, any aryl of which is optionally substituted with 1-3 substituents selected from i) F, Cl, Br, I, ii) —CN, iii) —NO$_2$, iv) —C(=O)(C$_1$-C$_4$-alkyl), v) —O(C$_1$-C$_4$-alkyl), vi) —N(C$_1$-C$_4$-alkyl)(C$_1$-C$_4$-alkyl), vii) —C$_{1-10}$alkyl, and viii) —C$_{1-10}$alkyl, wherein one or more of the alkyl carbons can be replaced by a —O—, —S(O)$_{1-2}$—, —O—C(O)—, —C(O)—O—, —C(O)—, —CH(OH)—, —C=C—, or —C≡C—;

R$^b$ is
(a) H; or
(b) C$_1$-C$_6$-alkyl, optionally substituted with one or more of the following substituents: F, CF$_3$, OH, O—(C$_1$-C$_4$)alkyl, S(O)$_{0-2}$—(C$_1$-C$_4$)alkyl, —OCONH$_2$, —OCONH(C$_1$-C$_4$alkyl), NH$_2$, NH(C$_1$-C$_4$alkyl), N(C$_1$-C$_4$alkyl)(C$_1$-C$_4$alkyl), NHCONH$_2$, NHCONH(C$_1$-C$_4$alkyl), —NHCON(C$_1$-C$_4$alkyl)(C$_1$-C$_4$alkyl), COO—(C$_1$-C$_4$-alkyl), COOH, CN, or CONH$_2$;

R$^2$ is:
(a) H;
(b) —C$_1$-C$_4$-alkyl, —C$_3$-C$_6$-Cycloalkyl or —C$_1$-C$_4$-alkyl-(C$_3$-C$_6$)-cycloalkyl, optionally substituted with one or more of the following substituents: F, CF$_3$, OH, O—(C$_1$-C$_4$)alkyl, S(O)$_{0-2}$—(C$_1$-C$_4$)alkyl, O—CONR$^a$R$^b$, NR$^a$R$^b$, N(R$^a$)CONR$^a$R$^b$, COO—(C$_1$-C$_4$)alkyl, COOH, CN, CONR$^a$R$^b$, SO$_2$NR$^a$R$^b$, N(R$^a$)SO$_2$NR$^a$R$^b$, —C(=NH)NH$_2$, tetrazolyl, triazolyl, imidazolyl, oxazolyl, oxadiazolyl, isooxazolyl, thiazolyl, furyl, thienyl, pyrazolyl, pyrrolyl, pyridyl, pyrimidinyl, pyrazinyl, phenyl, piperidinyl, morpholinyl, pyrrolidinyl or piperazinyl;
(c) —C$_0$-C$_4$-alkyl-C$_1$-C$_4$-perfluoroalkyl;
(d) aryl or —(C$_1$-C$_4$-alkyl)-aryl, wherein aryl is wherein aryl is phenyl, pyridyl, pyrimidinyl, furyl, thienyl, pyrrolyl, triazolyl, pyrazolyl, thiazolyl, isoxazolyl, oxazolyl, or oxadiazolyl, any aryl of which is optionally substituted with 1-3 substituents selected from i) F, Cl, Br, I, ii) —CN, iii) —NO$_2$, iv) —C(=O)(R$^a$), v) —OR$^a$, vi) —NR$^a$R$^b$, vii) —C$_{0-4}$alkyl-CO—OR$^a$, viii) —(C$_{0-4}$alkyl)-NH—CO—OR$^a$, ix) —(C$_{0-4}$alkyl)-CO—N(R$^a$)(R$^b$), x) —S(O)$_{0-2}$R$^a$, xi) —SO$_2$N(R$^a$)(R$^b$), xii) —NR$^a$SO$_2$R$^a$, xiii) —C$_{1-10}$alkyl, and xiv) —C$_{1-10}$alkyl, wherein one or more of the alkyl carbons can be replaced by a —NR$^a$—, —O—, —S(O)$_{1-2}$—, —O—C(O)—, —C(O)—O—, —C(O)—N(R$^a$)—, —N(R$^a$)—C(O)—, —N(R$^a$)—C(O)—N(R$^a$)—, —C(O)—, —CH(OH)—, —C=C—, or —C≡C—;
(e) —C(=O)(R$^a$), —CONR$^a$R$^b$, COO—(C$_1$-C$_4$)alkyl, —SO$_2$R$^a$, N(R$^a$)COR$^a$, —SO$_2$N(R$^a$)(R$^b$);

R$^3$ is
(a) H;
(b) —C$_1$-C$_4$-alkyl, —C$_3$-C$_6$-Cycloalkyl or —C$_1$-C$_4$-alkyl-(C$_3$-C$_6$)-cycloalkyl, optionally substituted with one or more of the following substituents: F, CF$_3$, OH, O—(C$_1$-C$_4$)alkyl, S(O)$_{0-2}$—(C$_1$-C$_4$)alkyl, O—CONR$^a$R$^b$, NR$^a$R$^b$, N(R$^a$)CONR$^a$R$^b$, COO—(C$_1$-C$_4$)alkyl, COOH, CN, CONR$^a$R$^b$, SO$_2$NR$^a$R$^b$, N(R$^a$)SO$_2$NR$^a$R$^b$, C(=NH)NH$_2$, tetrazolyl, triazolyl, imidazolyl, oxazolyl, oxadiazolyl, isooxazolyl, thiazolyl, furyl, thienyl, pyrazolyl, pyrrolyl, pyridyl, pyrimidinyl, pyrazinyl, phenyl, piperidinyl, morpholinyl, pyrrolidinyl or piperazinyl;
(c) —C$_0$-C$_4$-alkyl-C$_1$-C$_4$-perfluoroalkyl;
(d) aryl or —(C$_1$-C$_4$-alkyl)-aryl, wherein aryl is as defined above;
(e) —O—C$_1$-C$_4$-alkyl, —O—C$_0$-C$_4$-alkyl-C$_1$-C$_4$-perfluoroalkyl, —O-aryl or —O(C$_1$-C$_4$-alkyl)-aryl;

(f) —C(=O)($R^a$), —$SO_2R^a$, —$SO_2$N($R^a$)($R^b$), CN, N$R^aR^b$, $NO_2$, F, Cl, Br, I, OH, OCON$R^aR^b$, O($C_1$-$C_4$-alkyl)CON-$R^aR^b$, —$OSO_2$N$R^aR^b$, COO$R^a$, N($R^a$)CO$R^a$, or CON-$R^aR^b$;

$R^4$ and $R^5$ each independently is:

(a) H;

(b) —$C_1$-$C_6$-alkyl, —$C_2$-$C_6$-alkenyl, —$C_2$-$C_6$-alkynyl or —$C_3$-$C_6$-cycloalkyl, any of which is optionally substituted with one or more of the following substituents: F, $CF_3$, —O—($C_1$-$C_4$)alkyl, CN, —N($R^a$)($R^b$), —N($R^a$)CO—($C_1$-$C_4$)alkyl, COO$R^b$, CON($R^a$)($R^b$) or phenyl;

(c) —O—$C_0$-$C_6$-alkyl, —O-aryl, or —O—$C_1$-$C_4$-alkyl-aryl, wherein aryl is phenyl, pyridyl, pyrimidinyl, furyl, thienyl, pyrrolyl, triazolyl, pyrazolyl, thiazolyl, isoxazolyl, oxazolyl, or oxadiazolyl, any aryl of which is optionally substituted with 1-3 substituents selected from i) F, Cl, Br, I, ii) —CN, iii) —$NO_2$, iv) —C(=O)($R^a$), v) —O$R^a$, vi) —N$R^aR^b$, vii) —$C_{0-4}$alkyl-CO—O$R^a$, viii) —($C_{0-4}$alkyl)-NH—CO—O$R^a$, ix) —($C_{0-4}$alkyl)-CO—N($R^a$)($R^b$), x) —S(O)$_{0-2}R^a$, xi) —$SO_2$N($R^a$)($R^b$), xii) —N$R^a$$SO_2R^a$, xiii) —$C_{1-10}$alkyl, and xiv) —$C_{1-10}$alkyl, wherein one or more of the alkyl carbons can be replaced by a —N$R^a$—, —O—, —S(O)$_{1-2}$—, —O—C(O)—, —C(O)—O—, —C(O)—N($R^a$)—, —N($R^a$)—C(O)—, —N($R^a$)—C(O)—N($R^a$)—, —C(O)—, —CH(OH)—, —C=C—, or —C≡C—;

(d) —$C_0$-$C_4$-alkyl-$C_1$-$C_4$-perfluoroalkyl, or —O—$C_0$-$C_4$-alkyl-$C_1$-$C_4$-perfluoroalkyl; or (e) CN, $NH_2$, $NO_2$, F, Cl, Br, I, OH, OCON($R^a$)($R^b$)O($C_1$-$C_4$-alkyl)CON$R^aR^b$, —$OSO_2$N($R^a$)($R^b$), COO$R^b$, CON($R^a$)($R^b$), or aryl, wherein aryl is phenyl, pyridyl, pyrimidinyl, furyl, thienyl, pyrrolyl, triazolyl, pyrazolyl, thiazolyl, isoxazolyl, oxazolyl, or oxadiazolyl, any aryl of which is optionally substituted with 1-3 substituents selected from i) F, Cl, Br, I, ii) —CN, iii) —$NO_2$, iv) —C(=O)($R^a$), v) —O$R^a$, vi) —N$R^aR^b$, vii) —$C_{0-4}$alkyl-CO—O$R^a$, viii) —($C_{0-4}$alkyl)-NH—CO—O$R^a$, ix) —($C_{0-4}$alkyl)-CO—N($R^a$)($R^b$), x) —S(O)$_{0-2}R^a$, xi) —$SO_2$N($R^a$)($R^b$), xii) —N$R^a$$SO_2R^a$, xiii) —$C_{1-10}$alkyl, and xiv) —$C_{1-10}$alkyl, wherein one or more of the alkyl carbons can be replaced by a —N$R^a$—, —O—, —S(O)$_{1-2}$—, —O—C(O)—, —C(O)—O—, —C(O)—N($R^a$)—, —N($R^a$)—C(O)—, —N($R^a$)—C(O)—N($R^a$)—, —C(O)—, —CH(OH)—, —C=C—, or —C≡C; and $R^6$, $R^7$ and $R^8$ each independently is:

(a) H;

(b) $C_1$-$C_6$-alkyl, $C_2$-$C_4$-alkenyl, $C_2$-$C_4$-alkynyl or $C_3$-$C_6$-cycloalkyl, any of which is optionally substituted with one or more of the following substituents: F, $CF_3$, OH, O—($C_1$-$C_4$)alkyl, OCON($R^a$)($R^b$), N$R^aR^b$, COO$R^a$, CN, CON$R^aR^b$, N($R^a$)CON$R^aR^b$, N($R^a$)$SO_2$N$R^aR^b$, $SO_2$N$R^aR^b$, S(O)$_{0-2}$($C_1$-$C_4$-alkyl), —C(=NH)$NH_2$, tetrazolyl, triazolyl, imidazolyl, oxazolyl, oxadiazolyl, isooxazolyl, thiazolyl, furyl, thienyl, pyrazolyl, pyrrolyl, pyridyl, pyrimidinyl, pyrazinyl, phenyl, piperidinyl, morpholinyl, pyrrolidinyl, or piperazinyl;

(c) —O—$C_1$-$C_6$-alkyl, —O—$C_3$-$C_6$-cycloalkyl, —S—$C_1$-$C_6$-alkyl or —S—$C_3$-$C_6$-cycloalkyl, any of which is optionally substituted with one or more of the following substituents: F, $CF_3$, OH, O—($C_1$-$C_4$)alkyl, $NH_2$, NH($C_1$-$C_4$-alkyl), N($C_1$-$C_4$-alkyl)$_2$, COOH, CN, CON$H_2$, CONH($C_1$-$C_4$-alkyl), CONH($C_1$-$C_4$-alkyl)$_2$, $SO_2NH_2$, $SO_2$NH($C_1$-$C_4$-alkyl), tetrazolyl, triazolyl, imidazolyl, oxazolyl, oxadiazolyl, isooxazolyl, thiazolyl, furyl, thienyl, pyrazolyl, pyrrolyl, pyridyl, pyrimidinyl, pyrazinyl, phenyl, piperidinyl, morpholinyl, pyrrolidinyl, or piperazinyl;

(d) —$C_0$-$C_4$-alkyl-$C_1$-$C_4$-perfluoroalkyl, or —O—$C_0$-$C_4$-alkyl-$C_1$-$C_4$-perfluoroalkyl;

(e) —O-aryl, or —O—$C_1$-$C_4$-alkyl-aryl, wherein aryl is phenyl, pyridyl, pyrimidinyl, furyl, thienyl, pyrrolyl, triazolyl, pyrazolyl, thiazolyl, isoxazolyl, oxazolyl, or oxadiazolyl, any aryl of which is optionally substituted with 1-3 substituents selected from i) F, Cl, Br, I, ii) —CN, iii) —$NO_2$, iv) —C(=O)($R^a$), v) —O$R^a$, vi) —N$R^aR^b$, vii) —$C_{0-4}$alkyl-CO—O$R^a$, viii) —($C_{0-4}$alkyl)-NH—CO—O$R^a$, ix) —($C_{0-4}$alkyl)-CO—N($R^a$)($R^b$), x) —S(O)$_{0-2}R^a$, xi) —$SO_2$N($R^a$)($R^b$), xii) —N$R^a$$SO_2R^a$, xiii) —$C_{1-10}$alkyl, and xiv) —$C_{1-10}$alkyl, wherein one or more of the alkyl carbons can be replaced by a —N$R^a$—, —O—, —S(O)$_{1-2}$—, —O—C(O)—, —C(O)—O—, —C(O)—N($R^a$)—, —N($R^a$)—C(O)—, —N($R^a$)—C(O)—N($R^a$)—, —C(O)—, —CH(OH)—, —C=C—, or —C≡C; (f) CN, N($R^a$)($R^b$), $NO_2$, F, Cl, Br, I, —O$R^a$, —S$R^a$, —OCON($R^a$)($R^b$), —$OSO_2$N($R^a$)($R^b$), COO$R^b$, CON($R^a$)($R^b$), —N($R^a$)CON($R^a$)($R^b$), —N($R^a$)$SO_2$N($R^a$)($R^b$), —C(O$R^b$)$R^a$, —C(O$R^a$)$CF_3$, —C(NH$R^a$)$CF_3$, —C(=O)$R^a$, C(=O)$CF_3$, —$SOCH_3$, —$SO_2CH_3$, —$NHSO_2$($C_{1-6}$-alkyl), —$NHSO_2$-aryl, $SO_2$N($R^a$)($R^b$), —$CH_2OSO_2$N($R^a$)($R^b$), $SO_2$N($R^b$)—O$R^a$, —C(=NH)$NH_2$, —C$R_a$=N—O$R_a$, CH=CH or aryl, wherein aryl is phenyl, pyridyl, pyrimidinyl, furyl, thienyl, pyrrolyl, triazolyl, pyrazolyl, thiazolyl, isoxazolyl, oxazolyl, or oxadiazolyl, any aryl of which is optionally substituted with 1-3 substituents selected from i) F, Cl, Br, I, ii) —CN, iii) —$NO_2$, iv) —C(=O)($R^a$), v) —O$R^a$, vi) —N$R^aR^b$, vii) —$C_{0-4}$alkyl-CO—O$R^a$, viii) —($C_{0-4}$alkyl)-NH—CO—O$R^a$, ix) —($C_{0-4}$alkyl)-CO—N($R^a$)($R^b$), x) —S(O)$_{0-2}R^a$, xi) —$SO_2$N($R^a$)($R^b$), xii) —N$R^a$$SO_2R^a$, xiii) —$C_{1-10}$alkyl, and xiv) —$C_{1-10}$alkyl, wherein one or more of the alkyl carbons can be replaced by a —N$R^a$—, —O—, —S(O)$_{1-2}$—, —O—C(O)—, —C(O)—O—, —C(O)—N($R^a$)—, —N($R^a$)—C(O)—, —N($R^a$)—C(O)—N($R^a$)—, —C(O)—, —CH(OH)—, —C=C—, or —C≡C;

or when $R^6$ and $R^7$ are present on adjacent carbon atoms, $R^6$ and $R^7$, together with the ring to which they are attached, may form a bicyclic aromatic ring selected from naphthyl, indolyl, quinolinyl, isoquinolinyl, quinoxalinyl, benzofuryl, benzothienyl, benzoxazolyl, benzothiazolyl, and benzimidazolyl, any aromatic ring of which is optionally substituted with 1-4 independent substituents selected from i) halogen, ii) —CN, iii) —$NO_2$, iv) —CHO, v) —O—$C_{1-4}$ alkyl, vi) —N($C_{0-4}$alkyl)($C_{0-4}$alkyl), vii) —$C_{0-4}$alkyl-CO—O($C_{0-4}$alkyl), viii) —($C_{0-4}$alkyl)-NH—CO—O($C_{0-4}$ alkyl), ix) —($C_{0-4}$alkyl)-CO—N($C_{0-4}$alkyl)($C_{0-4}$alkyl), x) —S($C_{0-4}$alkyl), xi) —S(O)($C_{1-4}$alkyl), xii) —$SO_2$($C_{0-4}$ alkyl), xiii) —$SO_2$N($C_{0-4}$alkyl)($C_{0-4}$alkyl), xiv) —$NHSO_2$($C_{0-4}$alkyl)($C_{0-4}$alkyl), xv) —$C_{1-10}$alkyl and xvi) —$C_{1-10}$ alkyl in which one or more of the carbons can be replaced by a —N($C_{0-6}$alkyl)-, —O—, —S(O)$_{1-2}$—, —O—C(O)—, —C(O)—O—, —C(O)—N($C_{0-6}$alkyl)-, —N($C_{0-6}$alkyl)-C(O)—, —N($C_{0-6}$alkyl)-C(O)—N($C_{0-6}$ alkyl)-, —C(O)—, —CH(OH), —C=C—, or —C≡C—.

In one aspect, the present invention provides a compound described by the chemical Formula (I), or a pharmaceutically acceptable salt thereof, wherein $R^6$ is other than H and is attached at the ortho position.

In a second aspect, the present invention provides a compound described by the chemical Formula (II), or a pharmaceutically acceptable salt thereof, wherein $R^6$ is other than H and is attached at the ortho position.

In a third aspect, the present invention provides a compound described by the chemical Formula (III), or a pharmaceutically acceptable salt thereof, wherein
R⁶ is other than H and is attached at the ortho position.

In an embodiment of this third aspect, the present invention provides a compound described by the chemical Formula (III), or a pharmaceutically acceptable salt thereof, wherein
HET is

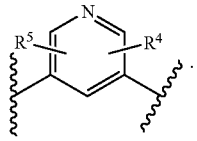

In another embodiment of this third aspect, the present invention provides a compound described by the chemical Formula (III), or a pharmaceutically acceptable salt thereof, wherein
HET is

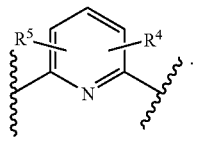

In a further embodiment of this third aspect, the present invention provides a compound described by the chemical Formula (III), or a pharmaceutically acceptable salt thereof, wherein
HET is

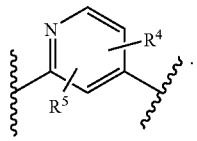

In a still further embodiment of this third aspect, the present invention provides a compound described by the chemical Formula (III), or a pharmaceutically acceptable salt thereof, wherein
HET is

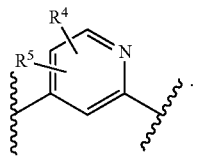

In yet another embodiment of this third aspect, the present invention provides a compound described by the chemical Formula (III), or a pharmaceutically acceptable salt thereof, wherein
HET is

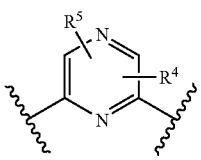

In a fourth aspect, the present invention provides a compound described by the chemical Formula (IV), or a pharmaceutically acceptable salt thereof, wherein R⁶ is other than H and is attached at the ortho position.

In an embodiment of this fourth aspect, the present invention provides a compound described by the chemical Formula (IV), or a pharmaceutically acceptable salt thereof, wherein
HET is

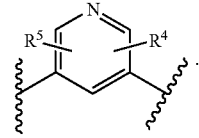

In another embodiment of this fourth aspect, the present invention provides a compound described by the chemical Formula (IV), or a pharmaceutically acceptable salt thereof, wherein
HET is

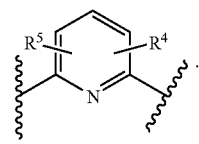

In a further embodiment of this fourth aspect, the present invention provides a compound described by the chemical Formula (IV), or a pharmaceutically acceptable salt thereof, wherein
HET is

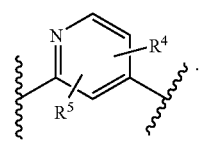

In a still further embodiment of this fourth aspect, the present invention provides a compound described by the chemical Formula (IV), or a pharmaceutically acceptable salt thereof, wherein
HET is

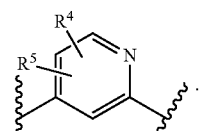

In a still further embodiment of this fourth aspect, the present invention provides a compound described by the chemical Formula (IV), or a pharmaceutically acceptable salt thereof, wherein
HET is

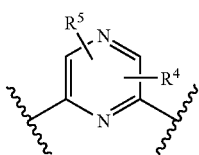

As used herein, "alkyl" as well as other groups having the prefix "alk" such as, for example, alkoxy, alkanoyl, alkenyl, and alkynyl means carbon chains which may be linear or branched or combinations thereof. Examples of alkyl groups include methyl, ethyl, propyl, isopropyl, butyl, sec- and tert-butyl, pentyl, hexyl, and heptyl. "Alkenyl," "alkynyl" and other like terms include carbon chains containing at least one unsaturated C—C bond.

The term "cycloalkyl" means carbocycles containing no heteroatoms, and includes mono-, bi- and tricyclic saturated carbocycles, as well as fused ring systems. Such fused ring systems can include one ring that is partially or fully unsaturated such as a benzene ring to form fused ring systems such as benzofused carbocycles. Cycloalkyl includes such fused ring systems as spirofused ring systems. Examples of cycloalkyl include cyclopropyl, cyclobutyl, cyclopentyl, cyclohexyl, decahydronaphthalene, adamantane, indanyl, indenyl, fluorenyl, and 1,2,3,4-tetrahydronaphalene. Similarly, "cycloalkenyl" means carbocycles containing no heteroatoms and at least one non-aromatic C—C double bond, and include mono-, bi- and tricyclic partially saturated carbocycles, as well as benzofused cycloalkenes. Examples of cycloalkenyl include cyclohexenyl, and indenyl.

The term "aryl" includes, but is not limited to, an aromatic substituent that is a single ring or multiple rings fused together. When formed of multiple rings, at least one of the constituent rings is aromatic. The term "aryl", unless specifically noted otherwise, also includes heteroaryls, and thus includes stable 5- to 7-membered monocyclic and stable 9- to 10-membered fused bicyclic heterocyclic ring systems that consist of carbon atoms and from one to four heteroatoms selected from the group consisting of N, O and S, wherein the nitrogen and sulfur heteroatoms may optionally be oxidized, and the nitrogen heteroatom may optionally be quaternized. Suitable aryl groups include phenyl, naphthyl, pyridyl, pyrimidinyl, furyl, thienyl, pyrrolyl, triazolyl, pyrazolyl, thiazolyl, isoxazolyl, oxazolyl, and oxadiazolyl.

The term "cycloalkyloxy," unless specifically stated otherwise, includes a cycloalkyl group connected by a short $C_{1-2}$alkyl to the oxy connecting atom.

The term "$C_{0-6}$alkyl" includes alkyls containing 6, 5, 4, 3, 2, 1, or no carbon atoms. An alkyl with no carbon atoms is a hydrogen atom substituent when the alkyl is a terminal group and is a direct bond when the alkyl is a bridging group.

The term "hetero," unless specifically stated otherwise, includes one or more O, S, or N atoms. For example, heterocycloalkyl and heteroaryl include ring systems that contain one or more O, S, or N atoms in the ring, including mixtures of such atoms. The hetero atoms replace ring carbon atoms. Thus, for example, a heterocyclo$C_5$alkyl is a five-member ring containing from 4 to no carbon atoms. Examples of heteroaryls include pyridinyl, quinolinyl, isoquinolinyl, pyridazinyl, pyrimidinyl, pyrazinyl, quinoxalinyl, furyl, benzofuryl, dibenzofuryl, thienyl, benzthienyl, pyrrolyl, indolyl, pyrazolyl, indazolyl, oxazolyl, benzoxazolyl, isoxazolyl, thiazolyl, benzothiazolyl, isothiazolyl, imidazolyl, benzimidazolyl, oxadiazolyl, thiadiazolyl, triazolyl, and tetrazolyl. Examples of heterocycloalkyls include azetidinyl, pyrrolidinyl, piperidinyl, piperazinyl, morpholinyl, tetrahydrofuranyl, imidazolinyl, pyrolidin-2-one, piperidin-2-one, and thiomorpholinyl.

The term "hetero$C_{0-4}$alkyl" means a heteroalkyl containing 3, 2, 1, or no carbon atoms. However, at least one heteroatom must be present. Thus, as an example, a hetero$C_{0-4}$alkyl having no carbon atoms but one N atom would be a —NH— if a bridging group and a —NH$_2$ if a terminal group. Analogous bridging or terminal groups are clear for an O or S heteroatom.

The term "amine," unless specifically stated otherwise, includes primary, secondary and tertiary amines.

The term "carbonyl," unless specifically stated otherwise, includes a $C_{0-6}$alkyl substituent group when the carbonyl is terminal.

The term "halogen" includes fluorine, chlorine, bromine and iodine atoms.

The term "optionally substituted" is intended to include both substituted and unsubstituted. Thus, for example, optionally substituted aryl could represent a pentafluorophenyl or a phenyl ring. Further, optionally substituted multiple moieties such as, for example, alkylaryl are intended to mean that the alkyl and the aryl groups are optionally substituted. If only one of the multiple moieties is optionally substituted then it will be specifically recited such as "an alkylaryl, the aryl optionally substituted with halogen or hydroxyl."

Compounds described herein may contain one or more double bonds and may thus give rise to cis/trans isomers as well as other conformational isomers. The present invention includes all such possible isomers as well as mixtures of such isomers unless specifically stated otherwise.

Compounds described herein can contain one or more asymmetric centers and may thus give rise to diastereoisomers and optical isomers. The present invention includes all such possible diastereoisomers as well as their racemic mixtures, their substantially pure resolved enantiomers, all possible geometric isomers, and pharmaceutically acceptable salts thereof. The above chemical Formulas are shown without a definitive stereochemistry at certain positions. The present invention includes all stereoisomers of the chemical Formulas and pharmaceutically acceptable salts thereof. Further, mixtures of stereoisomers as well as isolated specific stereoisomers are also included. During the course of the synthetic procedures used to prepare such compounds, or in using racemization or epimerization procedures known to those skilled in the art, the products of such procedures can be a mixture of stereoisomers.

The term "pharmaceutically acceptable salts" refers to salts prepared from pharmaceutically acceptable non-toxic bases or acids. When the compound of the present invention is acidic, its corresponding salt can be conveniently prepared from pharmaceutically acceptable non-toxic bases, including inorganic bases and organic bases. Salts derived from such inorganic bases include aluminum, ammonium, calcium, copper (ic and ous), ferric, ferrous, lithium, magnesium, manganese (ic and ous), potassium, sodium, zinc and the like salts. Salts derived from pharmaceutically acceptable organic non-toxic bases include salts of primary, secondary, and tertiary amines, as well as cyclic amines and substituted amines such as naturally occurring and synthesized substituted amines. Other pharmaceutically acceptable organic non-toxic bases from which salts can be formed include ion exchange resins such as, for example, arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, and tromethamine.

When the compound of the present invention is basic, its corresponding salt can be conveniently prepared from pharmaceutically acceptable non-toxic acids, including inorganic and organic acids. Such acids include, for example, acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like.

The pharmaceutical compositions of the present invention comprise a compound represented by Formula I, II, III or IV (or pharmaceutically acceptable salts thereof) as an active ingredient, a pharmaceutically acceptable carrier, and optionally one or more additional therapeutic agents or adjuvants. Such additional therapeutic agents can include, for example, i) opiate agonists or antagonists, ii) calcium channel antagonists, iii) 5HT receptor agonists or antagonists iv) sodium channel antagonists, v) NMDA receptor agonists or antagonists, vi) COX-2 selective inhibitors, vii) NK1 antagonists, viii) non-steroidal anti-inflammatory drugs ("NSAID"), ix) selective serotonin reuptake inhibitors ("SSRI") and/or selective serotonin and norepinephrine reuptake inhibitors ("SS-NRI"), x) tricyclic antidepressant drugs, xi) norepinephrine modulators, xii) lithium, xiii) valproate, and xiv) neurontin (gabapentin). The instant compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions may be conveniently presented in unit dosage form and prepared by any of the methods well known in the art of pharmacy.

The present compounds and compositions are useful for the treatment of chronic, visceral, inflammatory and neuropathic pain syndromes. They are useful for the treatment of pain resulting from traumatic nerve injury, nerve compression or entrapment, postherpetic neuralgia, trigeminal neuralgia, and diabetic neuropathy. The present compounds and compositions are also useful for the treatment of chronic lower back pain, phantom limb pain, chronic pelvic pain, neuroma pain, complex regional pain syndrome, chronic arthritic pain and related neuralgias, and pain associated with cancer, chemotherapy, HIV and HIV treatment-induced neuropathy. Compounds of this invention may also be utilized as local anesthetics. Compounds of this invention are useful for the treatment of irritable bowel syndrome and related disorders, as well as Crohns disease.

The instant compounds have clinical uses for the treatment of epilepsy and partial and generalized tonic seizures. They are also useful for neuroprotection under ischaemic conditions caused by stroke or neural trauma and for treating multiple sclerosis. The present compounds are useful for the treatment of tachy-arrhythmias. Additionally, the instant compounds are useful for the treatment of neuropsychiatric disorders, including mood disorders, such as depression or more particularly depressive disorders, for example, single episodic or recurrent major depressive disorders and dysthymic disorders, or bipolar disorders, for example, bipolar I disorder, bipolar II disorder and cyclothymic disorder; anxiety disorders, such as panic disorder with or without agoraphobia, agoraphobia without history of panic disorder, specific phobias, for example, specific animal phobias, social phobias, obsessive-compulsive disorder, stress disorders including post-traumatic stress disorder and acute stress disorder, and generalised anxiety disorders.

It will be appreciated that for the treatment of depression or anxiety, a compound of the present invention may be used in conjunction with other anti-depressant or anti-anxiety agents, such as norepinephrine reuptake inhibitors, selective serotonin reuptake inhibitors (SSRIs), monoamine oxidase inhibitors (MAOIs), reversible inhibitors of monoamine oxidase (RIMAs), serotonin and noradrenaline reuptake inhibitors (SNRIs), α-adrenoreceptor antagonists, atypical anti-depressants, benzodiazepines, $5-HT_{1A}$ agonists or antagonists, especially $5-HT_{1A}$ partial agonists, neurokinin-1 receptor antagonists, corticotropin releasing factor (CRF) antagonists, and pharmaceutically acceptable salts thereof.

Further, it is understood that compounds of this invention can be administered at prophylactically effective dosage levels to prevent the above-recited conditions and disorders, as well as to prevent other conditions and disorders associated with sodium channel activity.

Creams, ointments, jellies, solutions, or suspensions containing the instant compounds can be employed for topical use. Mouth washes and gargles are included within the scope of topical use for the purposes of this invention.

Dosage levels from about 0.01 mg/kg to about 140 mg/kg of body weight per day are useful in the treatment of inflammatory and neuropathic pain, or alternatively about 0.5 mg to about 7 g per patient per day. For example, inflammatory pain may be effectively treated by the administration of from about 0.01 mg to about 75 mg of the compound per kilogram of body weight per day, or alternatively about 0.5 mg to about 3.5 g per patient per day. Neuropathic pain may be effectively treated by the administration of from about 0.01 mg to about 125 mg of the compound per kilogram of body weight per day, or alternatively about 0.5 mg to about 5.5 g per patient per day.

The amount of active ingredient that may be combined with the carrier materials to produce a single dosage form will vary depending upon the host treated and the particular mode of administration. For example, a formulation intended for the oral administration to humans may conveniently contain from about 0.5 mg to about 5 g of active agent, compounded with an appropriate and convenient amount of carrier material which may vary from about 5 to about 95 percent of the total composition. Unit dosage forms will generally contain between from about 1 mg to about 1000 mg of the active ingredient, typically 25 mg, 50 mg, 100 mg, 200 mg, 300 mg, 400 mg, 500 mg, 600 mg, 800 mg or 1000 mg.

It is understood, however, that the specific dose level for any particular patient will depend upon a variety of factors. Such patient-related factors include the age, body weight, general health, sex, and diet of the patient. Other factors include the time and route of administration, rate of excretion, drug combination, and the severity of the particular disease undergoing therapy.

In practice, the compounds represented by Formula I, II, III and IV, or pharmaceutically acceptable salts thereof, can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). Thus, the pharmaceutical compositions of the present invention can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oil-in-water emulsion or as a water-in-oil liquid emulsion. In addition to the common dosage forms set out above, the compounds represented by Formula I, II, III, and IV, or pharmaceutically acceptable salts thereof, may also be administered by controlled release means and/or delivery devices. The compositions may be prepared by any of the methods of pharmacy. In general, such methods include a step of bringing into association the active ingredient with the carrier that constitutes one or more necessary ingredients. In general, the compositions are prepared by uniformly and intimately admixing the active ingredient with liquid carriers or finely divided solid carriers or both. The product can then be conveniently shaped into the desired presentation.

Thus, the pharmaceutical compositions of this invention may include a pharmaceutically acceptable carrier and a compound or a pharmaceutically acceptable salt of Formula I, II, III, or IV. The compounds of Formula I, II, III, and IV, or pharmaceutically acceptable salts thereof, can also be included in pharmaceutical compositions in combination with one or more therapeutically active compounds.

The pharmaceutical carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen.

In preparing the compositions for oral dosage form, any convenient pharmaceutical media may be employed. For example, water, glycols, oils, alcohols, flavoring agents, preservatives, coloring agents and the like may be used to form oral liquid preparations such as suspensions, elixirs and solutions; while carriers such as starches, sugars, microcrystalline cellulose, diluents, granulating agents, lubricants, binders, and disintegrating agents can be used to form oral solid preparations such as powders, capsules and tablets. Because of their ease of administration, tablets and capsules are the preferred oral dosage units whereby solid pharmaceutical carriers are employed. Optionally, tablets may be coated by standard aqueous or nonaqueous techniques A tablet containing the composition of this invention may be prepared by compression or molding, optionally with one or more accessory ingredients or adjuvants. Compressed tablets may be prepared by compressing, in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Each tablet preferably contains from about 0.1 mg to about 500 mg of the active ingredient and each cachet or capsule preferably containing from about 0.1 mg to about 500 mg of the active ingredient. Thus, a tablet, cachet, or capsule conveniently contains 0.1 mg, 1 mg, 5 mg, 25 mg, 50 mg, 100 mg, 200 mg, 300 mg, 400 mg, or 500 mg of the active ingredient taken one or two tablets, cachets, or capsules, once, twice, or three times daily.

Pharmaceutical compositions of the present invention suitable for parenteral administration may be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions of the present invention suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage, and thus should be preserved against the contaminating action of microorganisms such as bacteria and fungi. The carrier can be a solvent or dispersion medium containing, for example, water, ethanol, polyol (e.g. glycerol, propylene glycol and liquid polyethylene glycol), vegetable oils, and suitable mixtures thereof.

Pharmaceutical compositions of the present invention can be in a form suitable for topical use such as, for example, an aerosol, cream, ointment, lotion, and dusting powder. Further, the compositions can be in a form suitable for use in transdermal devices. These formulations may be prepared, utilizing a compound represented by Formula I, II, III, or IV, or pharmaceutically acceptable salts thereof, via conventional processing methods. As an example, a cream or ointment is prepared by mixing hydrophilic material and water, together with about 5 wt % to about 10 wt % of the compound, to produce a cream or ointment having a desired consistency.

Pharmaceutical compositions of this invention can be in a form suitable for rectal administration wherein the carrier is a solid, such as, for example, where the mixture forms unit dose suppositories. Suitable carriers include cocoa butter and other materials commonly used in the art. The suppositories may be conveniently formed by first admixing the composition with the softened or melted carrier(s) followed by chilling and shaping in moulds.

In addition to the aforementioned carrier ingredients, the pharmaceutical formulations described above may include, as appropriate, one or more additional carrier ingredients such as diluents, buffers, flavoring agents, binders, surface-active agents, thickeners, lubricants, and preservatives (including anti-oxidants). Furthermore, other adjuvants can be included to render the formulation isotonic with the blood of the intended recipient. Compositions containing a compound described by Formula I, II, III, or IV, or pharmaceutically acceptable salts thereof, can also be prepared in powder or liquid concentrate form.

The compounds and pharmaceutical compositions of this invention have been found to block sodium channels. Accordingly, an aspect of the invention is the treatment in mammals of maladies that are amenable to amelioration through blockage of neuronal sodium channels, including, for example, acute pain, chronic pain, visceral pain, inflammatory pain, and neuropathic pain by administering an effective amount of a compound of this invention. The term "mammals" includes humans, as well as other animals, such as, for example, dogs, cats, horses, pigs, and cattle. Accordingly, it is understood that the treatment of mammals other than humans refers to the treatment of clinical conditions in non-human mammals that correlate to the above-recited conditions.

Further, as described above, the instant compounds can be utilized in combination with one or more therapeutically active compounds. In particular, the inventive compounds can be advantageously used in combination with i) opiate agonists or antagonists, ii) calcium channel antagonists, iii) 5HT receptor agonists or antagonists iv) sodium channel antagonists, v) N-methyl-D-aspartate (NMDA) receptor agonists or antagonists, vi) COX-2 selective inhibitors, vii) neurokinin receptor 1 (NK1) antagonists, viii) non-steroidal anti-inflammatory drugs (NSAID), ix) selective serotonin reuptake inhibitors (SSRI) and/or selective serotonin and norepinephrine reuptake inhibitors (SSNRI), x) tricyclic antidepressant drugs, xi) norepinephrine modulators, xii) lithium, xiii) valproate, and xiv) neurontin (gabapentin).

The abbreviations used herein have the following tabulated meanings. Abbreviations not tabulated below have their meanings as commonly used unless specifically stated otherwise.

| | |
|---|---|
| Ac | Acetyl |
| AIBN | 2,2'-azobis(isobutyronitrile) |
| BINAP | 1,1'-bi-2-naphthol |
| Bn | Benzyl |
| CAMP | cyclic adenosine-3',5'-monophosphate |
| DAST | (diethylamino)sulfur trifluoride |
| DEAD | diethyl azodicarboxylate |
| DBU | 1,8-diazabicyclo[5.4.0]undec-7-ene |
| DIBAL | diisobutylaluminum hydride |
| DMAP | 4-(dimethylamino)pyridine |
| DMF | N,N-dimethylformamide |
| Dppf | 1,1'-bis(diphenylphosphino)-ferrocene |
| EDCI | 1-(3-dimethylaminopropyl)-3-ethylcarbodiimide hydrochloride |
| $Et_3N$ | Triethylamine |
| GST | glutathione transferase |
| HMDS | Hexamethyldisilazide |
| LDA | lithium diisopropylamide |
| m-CPBA | metachloroperbenzoic acid |
| MMPP | monoperoxyphthalic acid |
| MPPM | monoperoxyphthalic acid, magnesium salt $6H_2O$ |
| Ms | methanesulfonyl = mesyl = $SO_2Me$ |
| MsO | methanesulfonate = mesylate |
| NBS | N-bromo succinimide |
| NSAID | non-steroidal anti-inflammatory drug |
| o-Tol | ortho-tolyl |
| OXONE ® | $2KHSO_5 \cdot KHSO_4 \cdot K_2SO_4$ |
| PCC | pyridinium chlorochromate |
| $Pd_2(dba)_3$ | Bis(dibenzylideneacetone)palladium(0) |
| PDC | pyridinium dichromate |
| PDE | Phosphodiesterase |
| Ph | Phenyl |
| Phe | Benzenediyl |
| PMB | para-methoxybenzyl |
| Pye | Pyridinediyl |
| r.t. or RT | room temperature |
| Rac. | Racemic |
| SAM | aminosulfonyl or sulfonamide or $SO_2NH_2$ |
| SEM | 2-(trimethylsilyl)ethoxymethoxy |
| SPA | scintillation proximity assay |
| TBAF | tetra-n-butylammonium fluoride |
| Th | 2- or 3-thienyl |
| TFA | trifluoroacetic acid |
| TFAA | trifluoroacetic acid anhydride |
| THF | Tetrahydrofuran |
| Thi | Thiophenediyl |
| TLC | thin layer chromatography |
| TMS-CN | trimethylsilyl cyanide |
| TMSI | trimethylsilyl iodide |
| Tz | 1H (or 2H)-tetrazol-5-yl |
| XANTPHOS | 4,5-Bis-diphenylphosphanyl-9,9-dimethyl-9H-xanthene |
| $C_3H_5$ | Allyl |

Alkyl Group Abbreviations

| | |
|---|---|
| Me = | Methyl |
| Et = | ethyl |
| n-Pr = | normal propyl |
| i-Pr = | isopropyl |
| n-Bu = | normal butyl |
| i-Bu = | isobutyl |
| s-Bu = | secondary butyl |
| t-Bu = | tertiary butyl |
| c-Pr = | cyclopropyl |
| c-Bu = | cyclobutyl |
| c-Pen = | cyclopentyl |
| c-Hex = | cyclohexyl |

The following in vitro and in vivo assays were used in assessing the biological activity of the instant compounds.

Compound Evaluation (In Vitro Assay):

The identification of inhibitors of the sodium channel is based on the ability of sodium channels to cause cell depolarization when sodium ions permeate through agonist-modified channels. In the absence of inhibitors, exposure of an agonist-modified channel to sodium ions will cause cell depolarization. Sodium channel inhibitors will prevent cell depolarization caused by sodium ion movement through agonist-modified sodium channels. Changes in membrane potential can be determined with voltage-sensitive fluorescence resonance energy transfer (FRET) dye pairs that use two components, a donor coumarin ($CC_2$DMPE) and an acceptor oxanol ($DiSBAC_2(3)$). Oxanol is a lipophilic anion and distributes across the membrane according to membrane potential. In the presence of a sodium channel agonist, but in the absence of sodium, the inside of the cell is negative with respect to the outside, oxanol is accumulated at the outer leaflet of the membrane and excitation of coumarin will cause FRET to occur. Addition of sodium will cause membrane depolarization leading to redistribution of oxanol to the inside of the cell, and, as a consequence, to a decrease in FRET. Thus, the ratio change (donor/acceptor) increases after membrane depolarization. In the presence of a sodium channel inhibitor, cell depolarization will not occur, and therefore the distribution of oxanol and FRET will remain unchanged.

Cells stably transfected with the PN1 sodium channel (HEK-PN1) were grown in polylysine-coated 96-well plates at a density of ca. 140,000 cells/well. The media was aspirated, and the cells were washed with PBS buffer, and incubated with 100 µL of 10 µM $CC_2$-DMPE in 0.02% pluronic acid. After incubation at 25° C. for 45 min, media was removed and cells were washed 2× with buffer. Cells were incubated with 100 µL of $DiSBAC_2(3)$ in TMA buffer containing 20 µM veratridine, 20 nM brevetoxin-3, and test sample. After incubation at 25° C. for 45 min in the dark, plates were placed in the VIPR instrument, and the fluorescence emission of both $CC_2$-DMPE and $DiSBAC_2(3)$ recorded for 10 s. At this point, 100 µL of saline buffer was added to the wells to determine the extent of sodium-dependent cell depolarization, and the fluorescence emission of both dyes recorded for an additional 20 s. The ratio $CC_2$-DMPE/$DiSBAC_2(3)$, before addition of saline buffer equals 1. In the absence of inhibitors, the ratio after addition of saline buffer is >1.5. When the sodium channel has been completely inhibited by either a known standard or test compound, this ratio remains at 1. It is possible, therefore, to titrate the activity of a sodium channel inhibitor by monitoring the concentration-dependent change in fluorescence ratio.

Electrophysiological Assays (In Vitro Assays):

Cell preparation: A HEK-293 cell line stably expressing the PN1 sodium channel subtype was established in-house. The cells were cultured in MEM growth media (Gibco) with 0.5 mg/mL G418, 50 units/mL Pen/Strep and 1 mL heat-inactivated fetal bovine serum at 37° C. and 10% $CO_2$. For electrophysiological recordings, cells were plated on 35 mm dishes coated with poly-D-lysine.

Whole-cell recordings: HEK-293 cells stably expressing the PN1 sodium channel subtype were examined by whole cell voltage clamp (Hamill et. al. Pfluegers Archives 391:85-100 (1981)) using an EPC-9 amplifier and Pulse software (HEKA Electronics, Lamprecht, Germany). Experiments were performed at room temperature. Electrodes were fire-polished to resistances of 2-4 MΩ. Voltage errors were minimized by series resistance compensation, and the capacitance transient was canceled using the EPC-9's built-in circuitry. Data were acquired at 50 kHz and filtered at 7-10 kHz. The bath solution consisted of 40 mM NaCl, 120 mM NMDG Cl, 1 mM KCl, 2.7 mM $CaCl_2$, 0.5 mM $MgCl_2$, 10 mM NMDG HEPES, pH 7.4, and the internal (pipet) solution contained 110 mM Cs-methanesulfonate, 5 mM NaCl, 20 mM CsCl, 10 mM CsF, 10 mM BAPTA (tetra Cs salt), 10 mM Cs HEPES, pH 7.4.

The following protocols were used to estimate the steady-state affinity of compounds for the resting and inactivated state of the channel ($K_r$ and $K_i$, respectively):

1) 8 ms test-pulses to depolarizing voltages from −60 mV to +50 mV from a holding potential of −90 mV were used to construct current-voltage relationships (IV-curves). A voltage near the peak of the IV-curve (typically −10 or 0 mV) was used as the test-pulse voltage throughout the remainder of the experiment.

2) Steady-state inactivation (availability) curves were constructed by measuring the current activated during an 8 ms test-pulse following 10 s conditioning pulses to potentials ranging from −120 mV to −10 mV.

3) Compounds were applied at a holding potential at which 20-50% of the channels was inactivated and sodium channel blockage was monitored during 8 ms test pulses at 2 s intervals.

4) After the compounds equilibrated, the voltage-dependence of steady-state inactivation in the presence of compound was determined according to protocol 2) above. Compounds that block the resting state of the channel decrease the current elicited during test-pulses from all holding potentials, whereas compounds that primarily block the inactivated state shift the mid-point of the steady-state inactivation curve. The maximum current at negative holding potentials ($I_{max}$) and the difference in the mid-points of the steady-state inactivation curves (ΔV) in control and in the presence of a compound were used to calculate $K_r$ and $K_i$ using the following equations:

$$K_r = \frac{[\text{Drug}] * I_{\text{Max},Drug}}{I_{\text{Max},Control} - I_{\text{Max},Drug}}$$

$$K_i = \frac{[\text{Drug}]}{\left(1 + \frac{[\text{Drug}]}{K_r}\right) * e^{\frac{-\Delta V}{k}} - 1}$$

In cases where the compound did not affect the resting state, $K_i$ was calculated using the following equation:

$$K_i = \frac{[\text{Drug}]}{e^{\frac{-\Delta V}{k}} - 1}$$

Rat Formalin Paw Test (In Vivo Assay):

Compounds were assessed for their ability to inhibit the behavioral response evoked by a 50 μL injection of formalin (5%). A metal band was affixed to the left hind paw of male Sprague-Dawley rats (Charles River, 200-250 g) and each rat was conditioned to the band for 60 min within a plastic cylinder (15 cm diameter). Rats were dosed with either vehicle or a test compound either before (local) or after (systemic) formalin challenge. For local administration, compounds were prepared in a 1:4:5 vehicle of ethanol, PEG400 and saline (EPEGS) and injected subcutaneously into the dorsal surface of the left hind paw 5 min prior to formalin. For systemic administration, compounds were prepared in either a EPEGS vehicle or a Tween80 (10%)/sterile water (90%) vehicle and were injected i.v. (via the lateral tail vein 15 min after formalin) or p.o. (60 min before formalin). The number of flinches was counted continuously for 60 min using an automated nociception analyzer (UCSD Anesthesiology Research, San Diego, Calif.). Statistical significance was determined by comparing the total flinches detected in the early (0-10 min) and late (11-60 min) phase with an unpaired t-test.

In Vivo Assay Using Rat CFA Model:

Unilateral inflammation was induced with a 0.2 ml injection of complete Freund's adjuvant (CFA: *Mycobacterium tuberculosis*, Sigma; suspended in an oil/saline (1:1) emulsion; 0.5 mg *Mycobacterium*/mL) in the plantar surface of the left hindpaw. This dose of CFA produced significant hind paw swelling but the animals exhibited normal grooming behavior and weight gain over the course of the experiment. Mechanical hyperalgesia was assessed 3 days after tissue injury using a Randall-Selitto test. Repeated Measures ANOVA, followed by Dunnett's Post Hoc test.

SNL: Mechanical Allodynia (In Vivo Assay):

Tactile allodynia was assessed with calibrated von Frey filaments using an up-down paradigm before and two weeks following nerve injury. Animals were placed in plastic cages with a wire mesh floor and allowed to acclimate for 15 min before each test session. To determine the 50% response threshold, the von Frey filaments (over a range of intensities from 0.4 to 28.8 g) were applied to the mid-plantar surface for 8 s, or until a withdrawal response occurred. Following a positive response, an incrementally weaker stimulus was tested. If there was no response to a stimulus, then an incrementally stronger stimulus was presented. After the initial threshold crossing, this procedure was repeated for four stimulus presentations per animal per test session. Mechanical sensitivity was assessed 1 and 2 hr post oral administration of the test compound.

The compounds described in this invention displayed sodium channel blocking activity of from about <0.1 μM to about <50 μM in the in vitro assays described above. It is advantageous that the compounds display sodium channel blocking activity of <5 μM in the in vitro assays. It is more advantageous that the compounds display sodium channel blocking activity of <1 μM in the in vitro assays. It is even more advantageous that the compounds display sodium channel blocking activity of <0.5 μM in the in vitro assays. It is still more advantageous that the compounds display sodium channel blocking activity of <0.1 μM in the in vitro assays.

Methods of Synthesis

Compounds of the present invention can be prepared according to the Schemes provided below as well as the procedures provided in the Examples. The following Schemes and Examples further describe, but do not limit, the scope of the invention. The substituents are the same as in the above Formulas except where defined otherwise or otherwise apparent to one skilled in the art.

The novel compounds of the present invention can be readily synthesized using techniques known to those skilled in the art, such as those described, for example, in *Advanced Organic Chemistry*, March, 4th Ed., John Wiley and Sons, New York, N.Y., 1992; *Advanced Organic Chemistry*, Carey and Sundberg, Vol. A and B, 3rd Ed., Plenum Press, Inc., New York, N.Y., 1990; *Protective groups in Organic Synthesis*, Green and Wuts, 2nd Ed., John Wiley and Sons, New York, N.Y., 1991; *Comprehensive Organic Transformations*, Larock, VCH Publishers, Inc., New York, N.Y., 1988; *Handbook of Heterocyclic Chemistry*, Katritzky and Pozharskii, 2nd Ed., Pergamon, New York, N.Y., 2000 and references cited therein. The starting materials for the compounds of the present invention may be prepared from the chemical precursors that are readily available from commercial sources, including Aldrich Chemical Co. (Milwaukee, Wis.); Sigma Chemical Co. (St. Louis, Mo.); Lancaster Synthesis (Windham, N.H.); Ryan Scientific (Columbia, S.C.); Maybridge (Cornwall, UK); Matrix Scientific (Columbia, S.C.); Arcos, (Pittsburgh, Pa.) and Trans World Chemicals (Rockville, Md.).

The procedures described herein for the synthesis of compounds of this invention may include one or more steps of protecting group manipulations and of purification, such as, recrystallization, distillation, column chromatography, flash chromatography, thin-layer chromatography (TLC), radial chromatography and high-pressure chromatography (HPLC). The products can be characterized by using various techniques well known in the chemical arts, including proton and carbon-13 nuclear magnetic resonance ($^1$H and $^{13}$C NMR), infrared and ultraviolet spectroscopy (IR and UV), X-ray crystallography, elemental analysis and HPLC and mass spectrometry (LC-MS). Methods of protecting group manipulation, purification, structure identification and quantification are well known to one skilled in the art of chemical synthesis.

The compounds of the present invention can be prepared by using one or more of the following schemes:

Scheme 1:

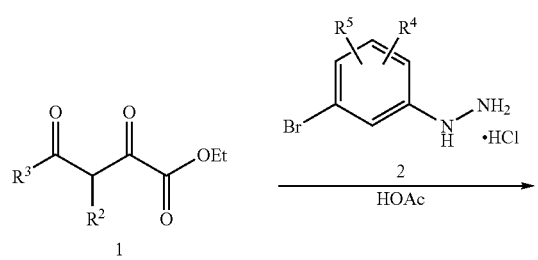

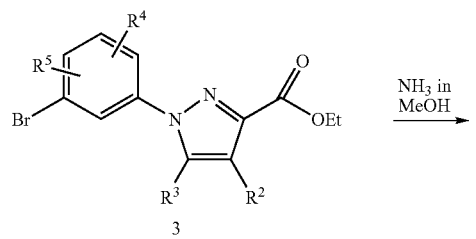

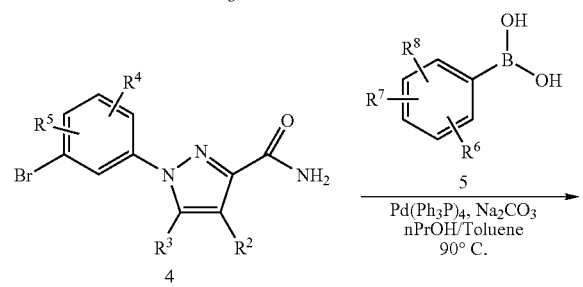

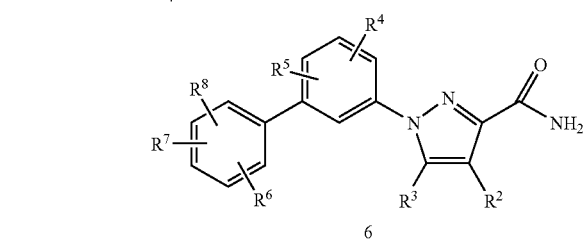

An appropriate 1,3-diketone 1 can be reacted with an aryl hydrazine 2 to give the pyrazole-3-carboxylate 3, which can be easily converted into the corresponding amide 4. Reaction of 4 with an appropriate phenyl boronic acid 5 under Pd-catalyzed cross-coupling condition [Suzuki et. al., Chem. Rev., 95: 2457, (1995)] can produce the desired biphenyl pyrazole 6. The Pd-catalyzed cross-coupling reaction, known as a Suzuki Reaction, is one of the most versatile methods for the synthesis of biaryl compounds. In this reaction, an appropriate aryl bromo, iodo, or triflate compound such as 3 or 4 is reacted with an aryl boronic acid in the presence of a palladium catalyst such as palladium acetate with triphenyl phosphine and aqueous sodium carbonate in a solvent such as toluene and a co-solvent such as n-propanol [Suzuki et. al., Chem. Rev., 95: 2457, (1995)]. A variety of aryl boronic acids are commercially available or can be prepared conveniently from the corresponding aryl bromide or iodide by converting it to an organolithium derivative [Baldwin, J. E. et al., Tetrahedron Lett., 39: 707-710 (1998)], or a Grignard reagent followed by treatment with trialkylborate [Li, J. J. et al, J. Med. Chem, 38: 4570-4578(1995) and Piettre, S. R. et al., J. Med Chem., 40: 4208-4221 (1997)].

Scheme 2:

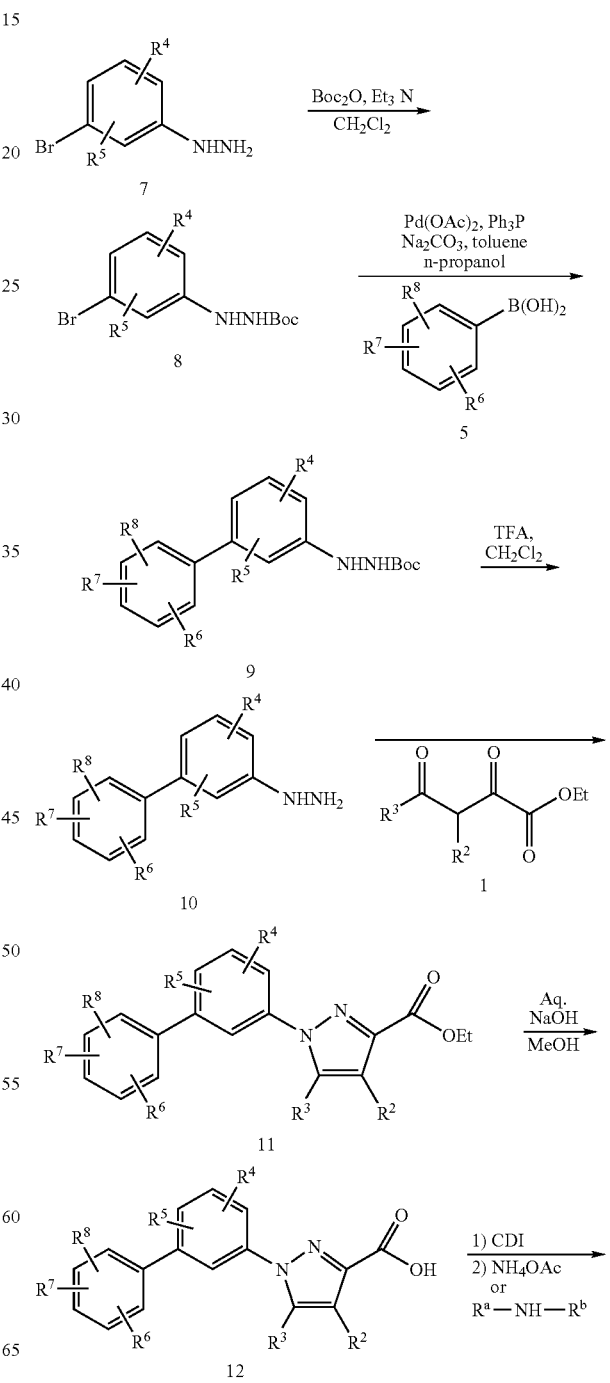

-continued

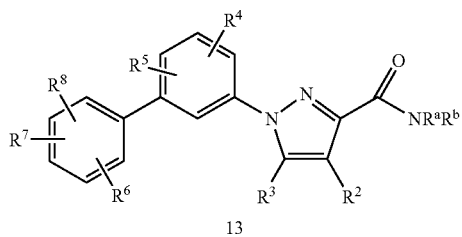

In an alternative approach, the pyrazole 6 can be synthesized as shown in Scheme 2. The Boc protected aryl hydrazide 8 can be cross-coupled, as described above, to provide the protected biaryl hydrazide 9. The Boc protecting group of compound 9 can be removed under standard conditions, trifluoroacetic acid in dichloromethane, to give the TFA salt of hydrazide 10 which can be desalted with aqueous NaOH solution and reacted with a diketone 1 to provide the ester 11. Ester 11 is hydrolyzed to the corresponding acid 12 which is then reacted with carbonyldiimidazole (CDI) in DMF, followed by ammonium acetate or an appropriate amine to give the pyrazole amide 13.

Scheme 3:

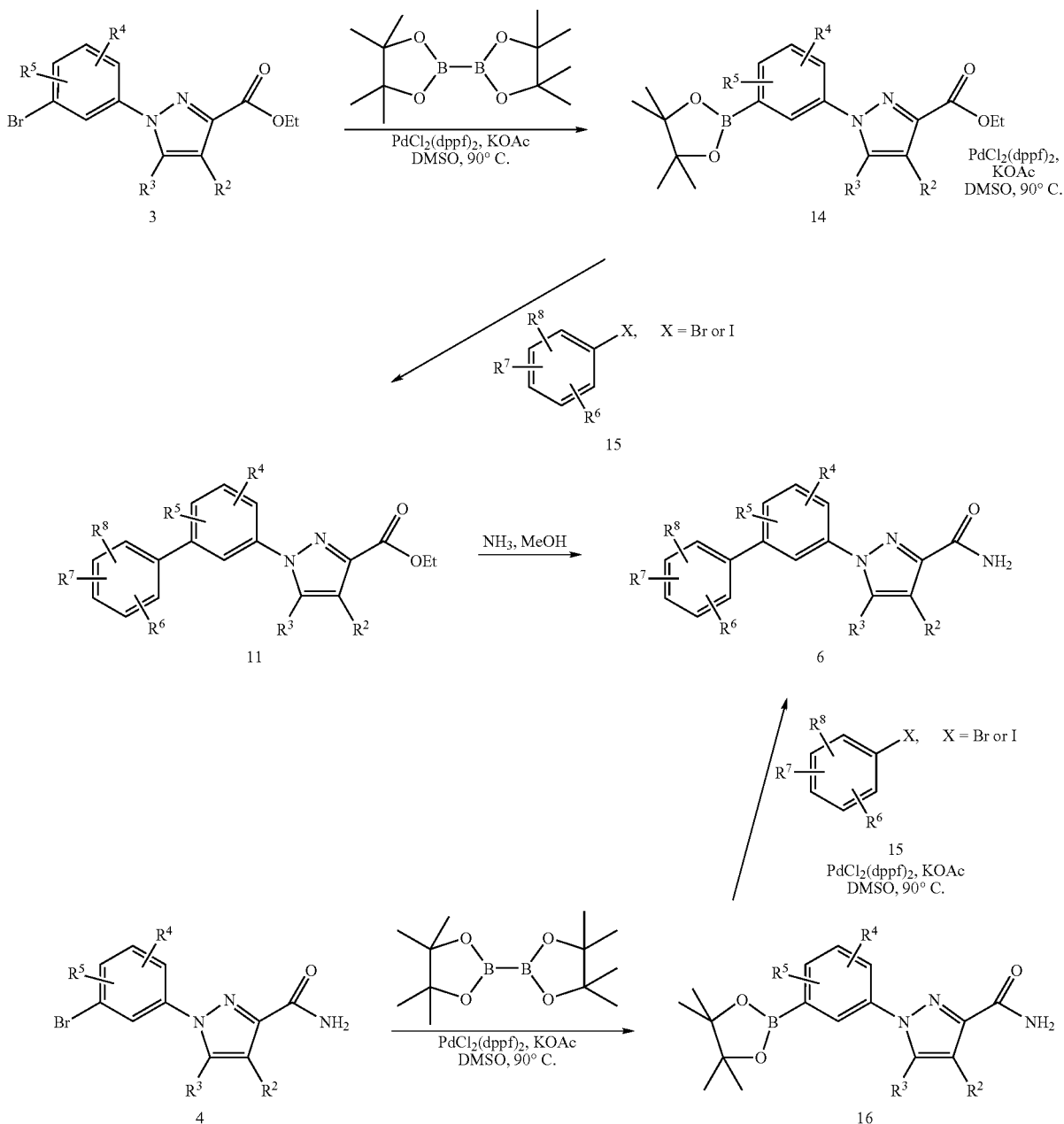

In Scheme 3, the biaryl compounds, such as 11 and 6, can be prepared by forming the aryl boronates (14 and 16) from the corresponding halo compounds such as 3 and 4, respectively. Aryl boronates can be used as an alternative to aryl boronic acids in these Pd-catalyzed coupling reactions [Giroux, A. et. al., *Tetrahedron Lett.*, 38, 3841(1997)]. The boronates can be easily prepared from the aryl bromides, iodides and trifluoromethane sulfonates using the method described by Murata, M. et. al., *J. Org. Chem.* 65: 164-168 (2000).

Scheme 4:

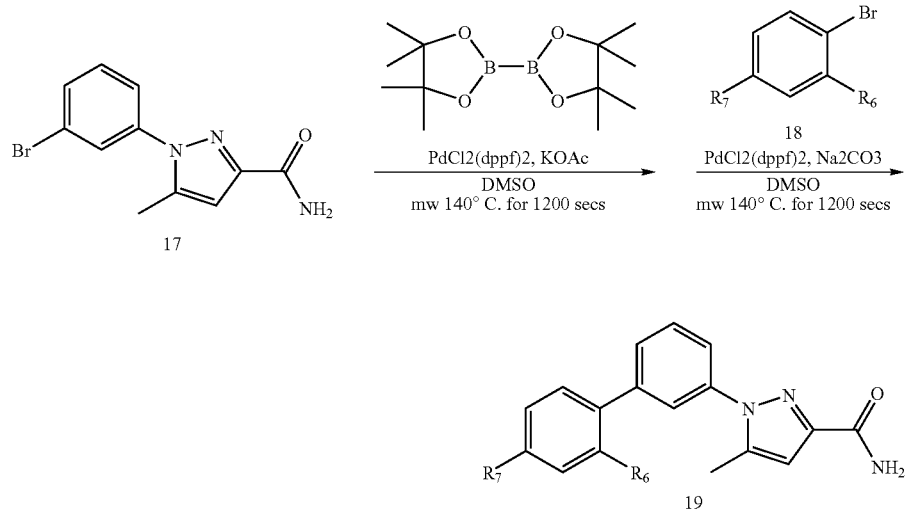

The chemistry described in Scheme 3 can be also accomplished by forming the boronates in situ, followed by their coupling with an appropriate aryl halide 18 under microwave heating to provide a pyrazole 19.

Scheme 5:

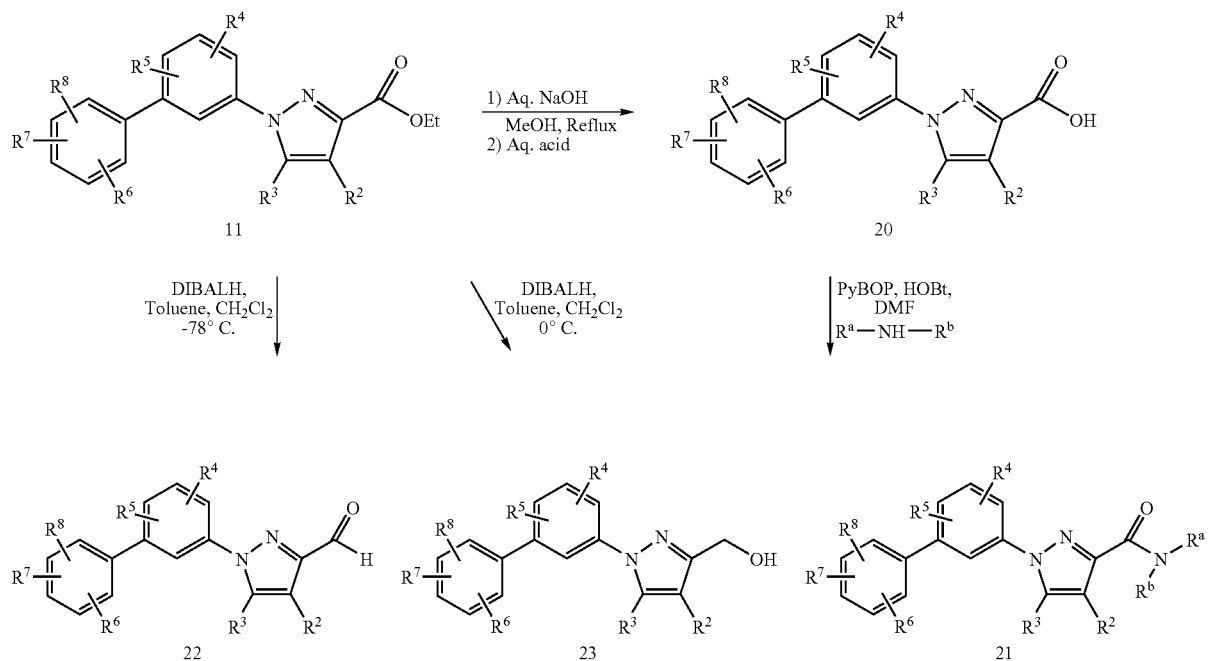

The pyrazole 3-carboxamides 21 can be prepared from the corresponding carboxylic acid 20 as outlined in Scheme 5. The aldehyde 22 can be prepared by treating the ester 11 with a reducing agent such as diisobutylaluminium hydride (DIBALH) at −78° C. However, treatment of 11 with DIBALH at 0° C. can provide the corresponding alcohol 23, which can be converted into carbamates 27 from Scheme 7.

Scheme 6:

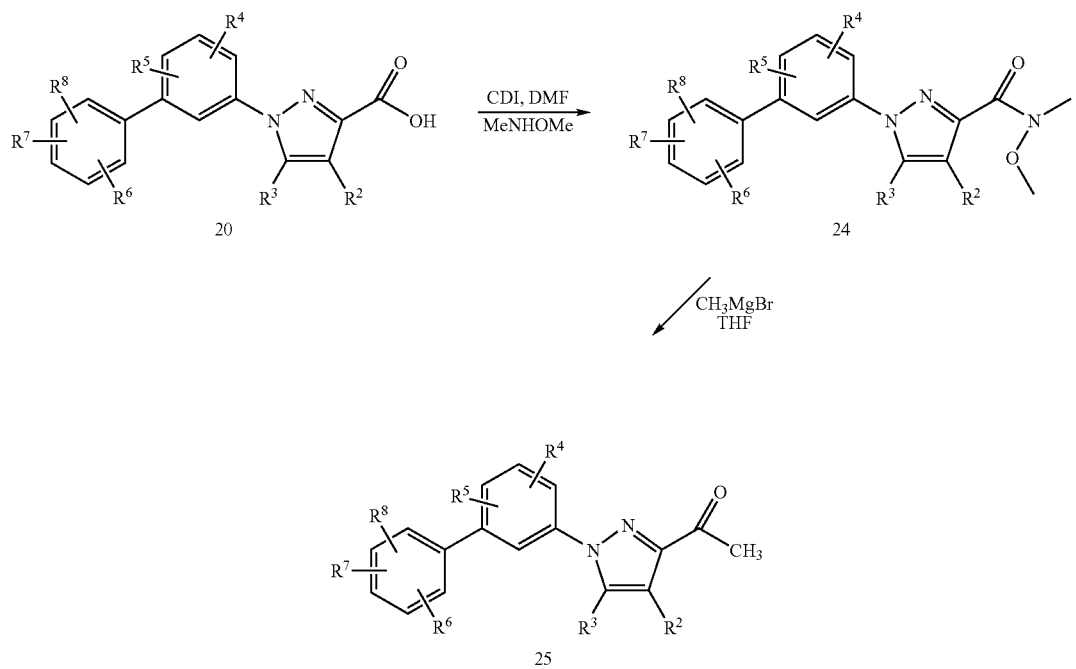

The synthesis of ketone 25 can be accomplished by the reaction of methyl magnesium bromide with the amide 24.

Scheme 7:

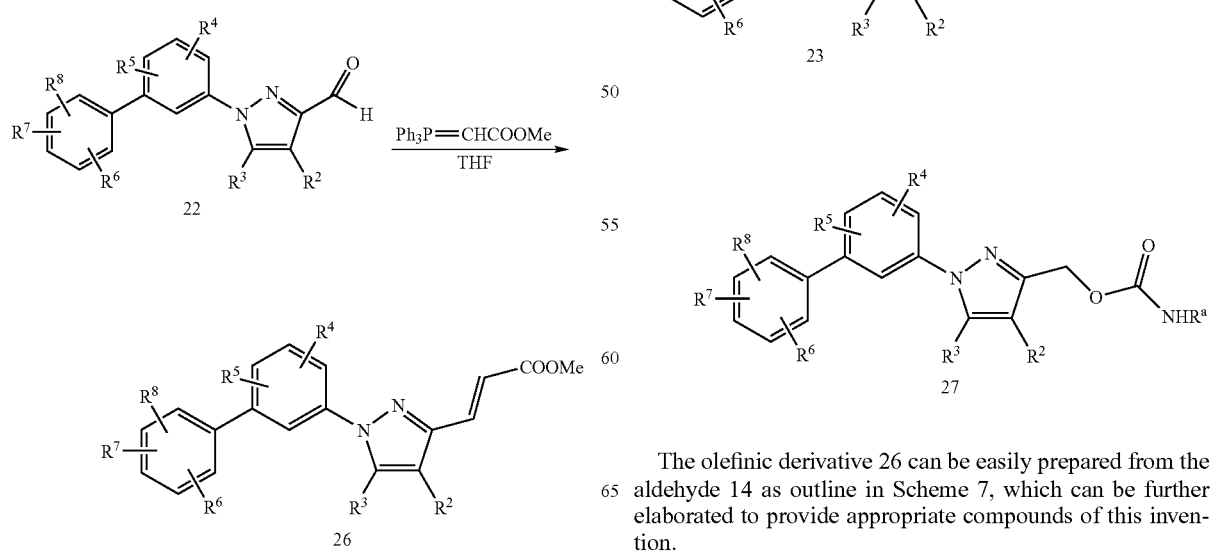

The olefinic derivative 26 can be easily prepared from the aldehyde 14 as outline in Scheme 7, which can be further elaborated to provide appropriate compounds of this invention.

Scheme 8:
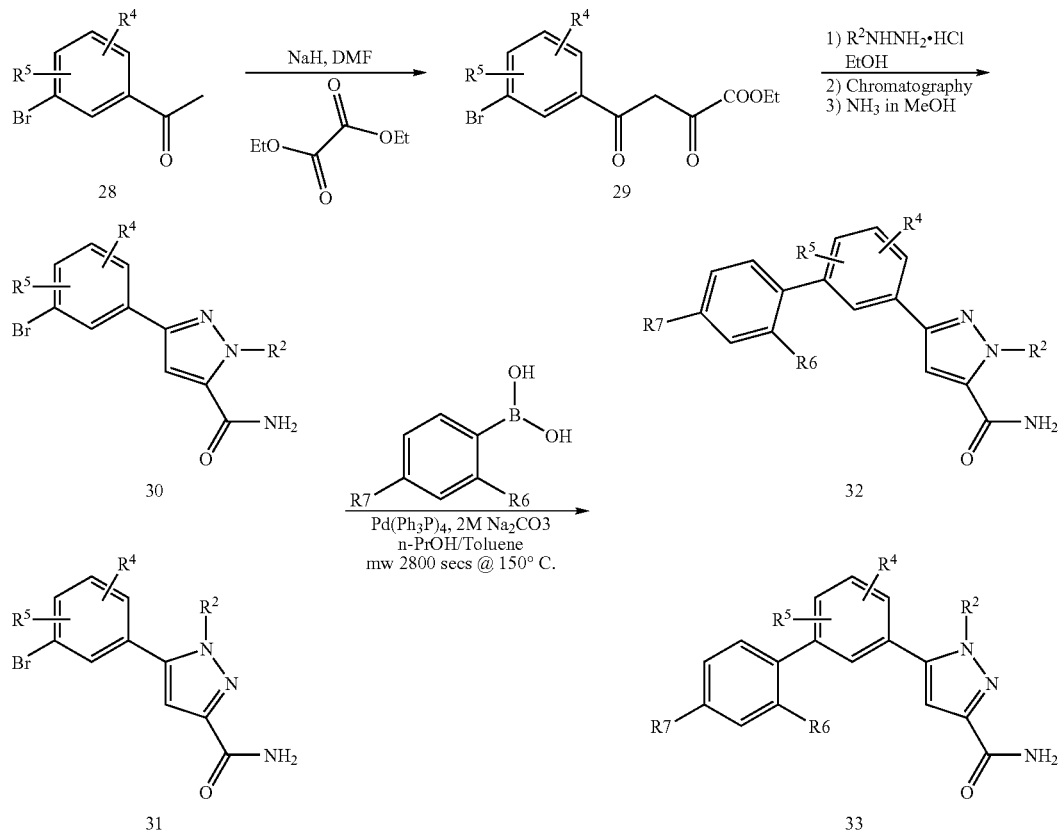
In a protocol to prepare the isomeric pyrazoles 32 and 33, the α-ketoester 29 is reacted with an appropriate substituted hydrazine to provide a mixture of pyrazole esters, which can be separated by chromatography. The individual ester derivative is then reacted with ammonia to give 30 and 31, which after reaction with aryl boronic acids affords 32 and 33.
Scheme 9:
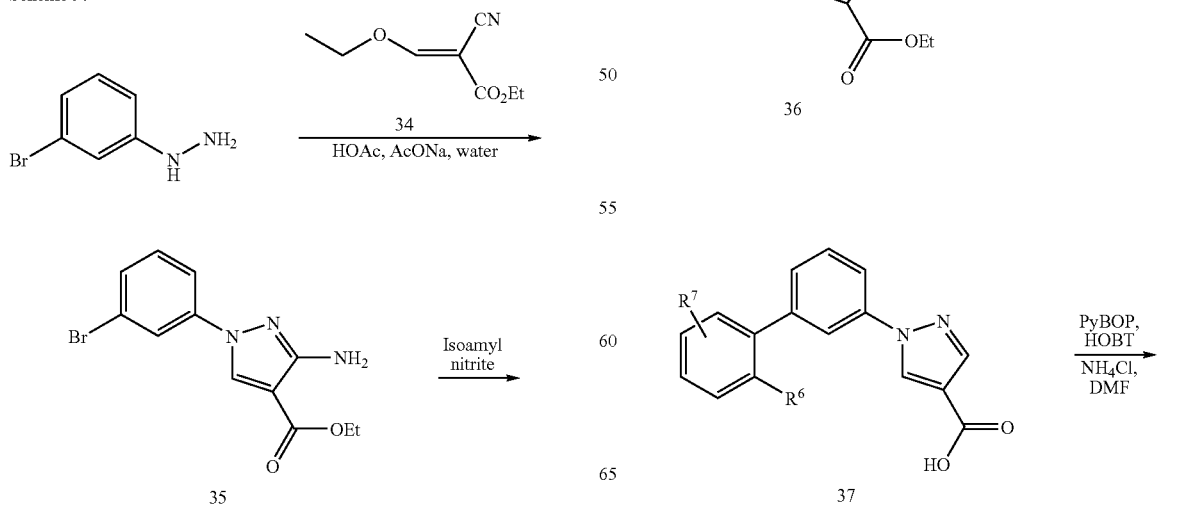

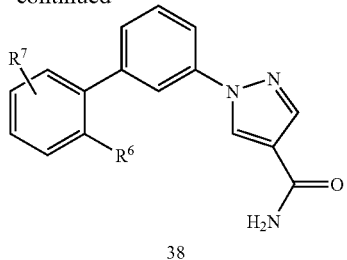

38

A typical scheme for the synthesis of pyrazole 4-carboxamides 38 is outlined in Scheme 9. Reaction of an appropriate hydrazine with 34 provides 3-amino-pyrazole-4-carboxylic acid ester 35, which can be treated with isoamyl nitrite in THF (See, e.g., *J. Het. Chem* 1987, p. 267) to produce the desamino pyrazole 36.

Scheme 11:

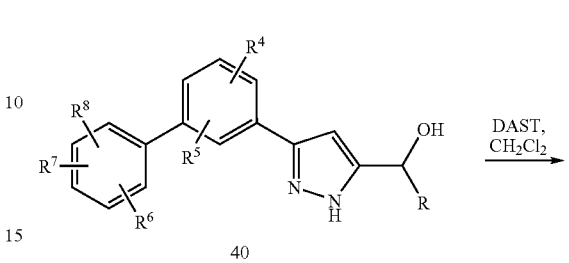

40

Scheme 10:

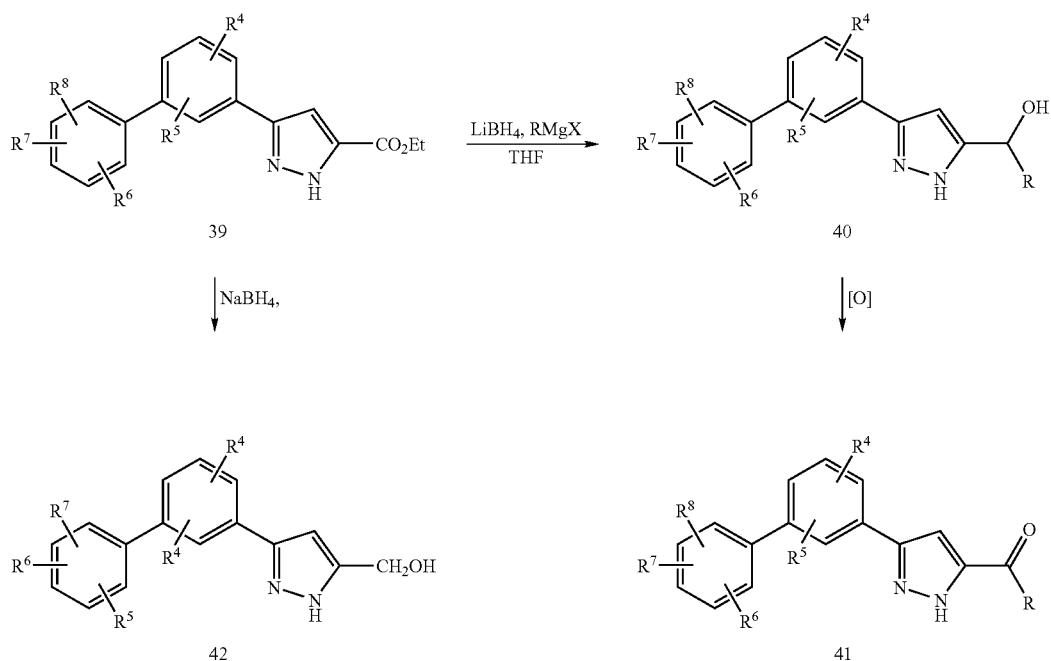

In Scheme 10, pyrazole ester 39 can be converted into a secondary alcohol 40 by reaction with a mixture of lithium borohydride and a Grignard reagent in an aprotic solvent such as THF. Alternatively, ester 39 can be reduced to primary alcohol 42 by any of several reducing agents, which include lithium aluminum hydride (LAH), diisobutylaluminum hydride (DIBALH) and sodium borohydride (NaBH$_4$). Either alcohol 40 or 42 can be further derivatized by any number of methods. In one example, alcohol 40 can be oxidized to the ketone 41 by a variety of oxidizing reagents which include chromium-based reagents, and Swern type reagents (DMSO and oxalyl chloride).

-continued

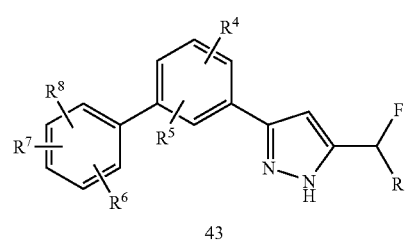

43

The alcohol 48 also can be converted to fluoro derivative 43 by reaction with diethylaminosulfurtrifluoride (DAST) in dichlormethane at reduced temperatures, as described in Scheme 11.

Scheme 12:

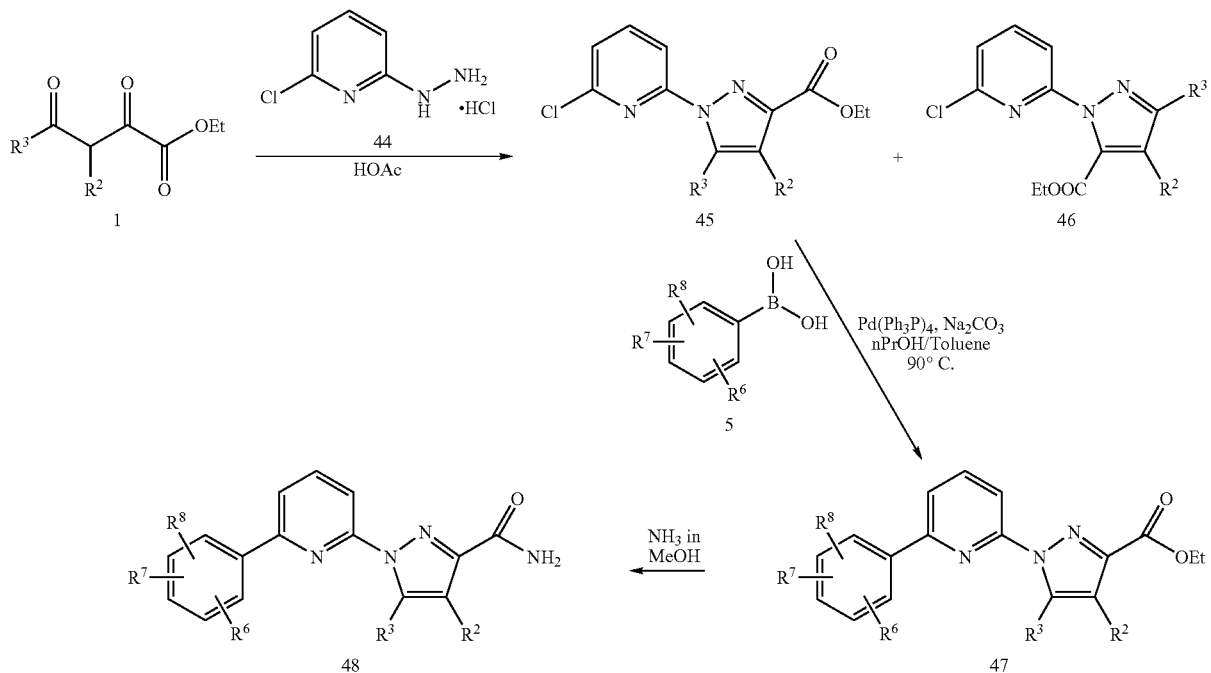

The pyridyl-pyrazole-3-carboxylate 48 can be prepared as outlined in Scheme 12.

Appropriate solvents are those in which one or all of the reactants will at least partially be soluble and will not adversely interact with either the reactants or the product. Suitable solvents include aromatic hydrocarbons (e.g. toluene, xylenes), halogenated solvents (e.g, methylene chloride, chloroform, carbontetrachloride, chlorobenzenes), ethers (e.g, diethyl ether, diisopropylether, tert-butyl methyl ether, diglyme, tetrahydrofuran, dioxane, anisole), nitriles (e.g, acetonitrile, propionitrile), ketones (e.g, 2-butanone, dithyl ketone, tert-butyl methyl ketone), alcohols (e.g, methanol, ethanol, n-propanol, iso-propanol, n-butanol, t-butanol), dimethyl formamide (DM), dimethylsulfoxide (DMSO) and water. Mixtures of two or more solvents can also be used. Suitable bases are, generally, alkali metal hydroxides, alkaline earth metal hydroxides such as lithium hydroxide, sodium hydroxide, potassium hydroxide, barium hydroxide, and calcium hydroxide; alkali metal hydrides and alkaline earth metal hydrides such as lithium hydride, sodium hydride, potassium hydride and calcium hydride; alkali metal amides such as lithium amide, sodium amide and potassium amide; alkali metal carbonates and alkaline earth metal carbonates such as lithium carbonate, sodium carbonate, cesium carbonate, sodium hydrogen carbonate, and cesium hydrogen carbonate; alkali metal alkoxides and alkaline earth metal alkoxides such as sodium methoxide, sodium ethoxide, potassium tert-butoxide and magnesium ethoxide; alkali metal alkyls such as methyllithium, n-butyllithium, sec-butyllithium, t-bultyllithium, phenyllithium, and alkyl magnaesium halides; organic bases such as trimethylamine, triethylamine, triisopropylamine, N,N-diisopropylethylamine, piperidine, N-methyl piperidine, morpholine, N-methyl morpholine, pyridine, collidines, lutidines, and 4-dimethylaminopyridine; and also bicyclic amines such as DBU and DABCO.

As described previously, in preparing the compositions for oral dosage form, any of the usual pharmaceutical media can be employed. For example, in the case of oral liquid preparations such as suspensions, elixirs and solutions, water, glycols, oils, alcohols, flavoring agents, preservatives, coloring agents and the like may be used; or in the case of oral solid preparations such as powders, capsules and tablets, carriers such as starches, sugars, microcrystalline cellulose, diluents, granulating agents, lubricants, binders, disintegrating agents, and the like may be included. Because of their ease of administration, tablets and capsules represent the most advantageous oral dosage unit form in which solid pharmaceutical carriers are obviously employed. If desired, tablets may be coated by standard aqueous or nonaqueous techniques. In addition to the common dosage forms set out above, controlled release means and/or delivery devices may also be used in administering the instant compounds and compositions.

It is understood that the functional groups present in compounds described in the above schemes can be further manipulated, when appropriate, using the standard functional group transformation techniques available to those skilled in the art, to provide desired compounds described in this invention.

Unless specifically stated otherwise, the experimental procedures were performed under the following conditions: All operations were carried out at room or ambient temperature; that is, at a temperature in the range of 18-25° C. Evaporation of solvent was carried out using a rotary evaporator under reduced pressure (600-4000 pascals: 4.5-30 mm. Hg) with a bath temperature of up to 60° C. The course of reactions was followed by thin layer chromatography (TLC) and reaction times are given for illustration only. Melting points are uncorrected and 'd' indicates decomposition. The melting points given are those obtained for the materials prepared as

EXAMPLE 1

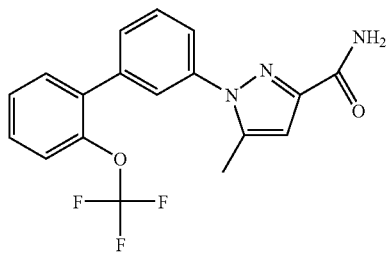

5-Methyl-1-[2'-(trifluoromethoxy)-1,1'-biphenyl-3-yl]-1H-pyrazole-3-carboxamide

Step 1:

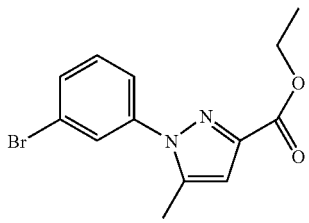

Ethyl 1-(3-bromophenyl)-5-methyl-1H-pyrazole-3-carboxylate

A solution of 3-bromophenylhydrazine hydrochloride (2 g, 8.9 mmol) and ethyl-2,4-dioxovalerate (1.69 g, 10.7 mmol) in acetic acid (44 ml) was refluxed for 16 hours. The reaction was cooled to room temperature and concentrated under reduced pressure. The residue was partitioned between ethyl acetate and water. The organic layer was washed with water, saturated bicarbonate and brine, and then dried over sodium sulfate, filtered and concentrated in vacuo. The crude product, thus obtained, was purified by silica-gel column chromatography (4.8:0.2 hexanes/ethyl acetate) to give the product (2.34 g, 84%) as a syrup.

$^1$HNMR (CDCl$_3$)(δ, ppm): 7.71 (s, 1H), 7.65 (d, 1H), 7.38 (d, 1H), 7.32 (t, 1H), 6.76 (s, 1H), 4.45 (q, 2M), 2.38 (s, 3H), 1.42 (t, 3H). MS (ESI): m/e 310.3 (M+2)$^+$.

Step 2:

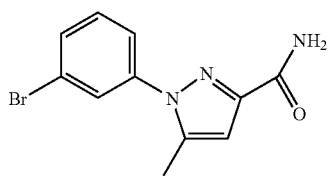

1-(3-bromophenyl)-5-methyl-1H-pyrazole-3-carboxamide

A solution of ethyl 1-(3-bromophenyl)-5-methyl-1H-pyrazole-3-carboxylate (4.28 g, 17.8 mmol) in 2N NaOH (17.85 ml) was refluxed for 16 hours. The reaction was cooled to room temperature, neutralized with 10% citric acid and extracted with ethylacetate. The organic phase was washed with brine, dried over sodium sulfate, filtered and concentrated to give 1-(3-bromophenyl)-1H-pyrazole-3-carboxylic acid (3.29 g, 89%).

To a solution of the carboxylic acid (3.79 g, 14.1 mmol) in DMF (47 ml) was added 1,1-carbonyldiimidazole (3.45 g, 21.2 mmol) and the mixture was stirred at room temperature for 3 hours. Anhydrous ammonium acetate (10.9 g, 141 mmol) was then added and the reaction was stirred at room temperature for an additional 16 hours. The reaction mixture was partitioned between ethylacetate and saturated sodium bicarbonate. The organic phase was washed with water, brine, then dried over sodium sulfate and concentrated. The crude product obtained was purified by silica-gel column chromatography (2:3 hexanes/ethyl acetate) to give the product as a white solid (3.23 g, 82%).

$^1$HNMR (CDCl$_3$)(δ, ppm): 7.69 (s, 1H), 7.61 (d, 1H), 7.44-7.39 (m, 2H), 6.81 (br s, 1H), 6.77 (s, 1H), 5.50 (br s, 1H). MS (ESI): m/e 281.2 (M+1)$^+$.

Step 3:

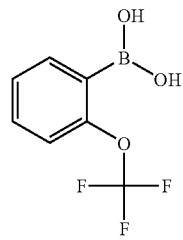

2-(Trifluoromethoxy)phenylboronic acid n-Butyllithium (5.9 ml, 9.5 mmol) was added to a solution of 1-bromo-2-(trifluoromethoxy)benzene (2 g, 8.2 mmol) in tetrahydrofuran (28 ml) at −78° C. and stirred for 45 minutes. Triisopropyl borate (2.58 ml, 11.1 mmol) was added dropwise to the reaction mixture and the solution was slowly brought to room temperature over 16 hours. The reaction mixture was quenched with water, made basic with 2N NaOH and extracted with ethyl acetate. The aqueous solution was acidified with 2N HCl, stirred for 1 hour at room temperature and extracted into ethyl acetate. The organic layer was washed with water, brine solution and dried over sodium sulfate. It was filtered and concentrated to give the product (1.10 g, 65%) as a white solid.

¹HNMR (CDCl₃)(δ, ppm): 7.96 (dd, J=7.2, 1.6 Hz, 1H), 7.53 (ddd, J=9.1, 7.3, 1.8 Hz, 1H), 7.38 (td, J =7.3, 0.7 Hz, 1H), 7.28 (d, J=8.2 Hz, 1H), 5.25 (br s, 2H). MS: m/e 206.9 (M+1)⁺.

Step 4:

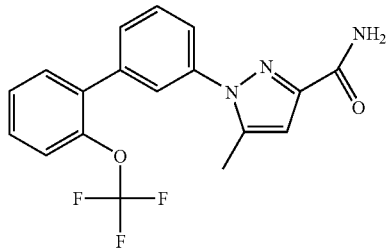

5-Methyl-1-[2'-(trifluoromethoxy)-1,1'-biphenyl-3-yl]-1H-pyrazole-3-carboxamide

To a solution of ethyl 1-(3-bromophenyl)-5-methyl-1H-pyrazole-3-carboxamide (0.237 g, 0.8 mmol) and 2-trifluoromethoxyphenyl boronic acid (0.262 g, 1.2 mmol) in n-propanol/toluene (1.27 ml:0.42 ml) mixture were added tetrakis(triphenylphosphine)palladium (0.019 g, 0.01 mmol) and 2M sodium carbonate (0.84 ml). The reaction mixture was heated at 90° C. for 16 hours, and then cooled and partitioned between ethyl acetate and water. The organic phase was washed with saturated sodium bicarbonate and brine, then dried over sodium sulfate and concentrated. The crude product was purified by silica-gel column chromatography (3.5:1.5 hexanes/acetone) to give the product (0.270 g, 88%) as a solid.
¹HNMR (CDCl₃)(δ, ppm): 7.64-7.57 (m, 3H), 7.53-7.41 (m, 5H), 6.85 (br s, 1H), 6.79 (s, 1H, 5.49 (br s, 1H), 2.42 (s, 3H). MS (ESI): m/e: 362.0 (M+1)⁺.

EXAMPLE 2

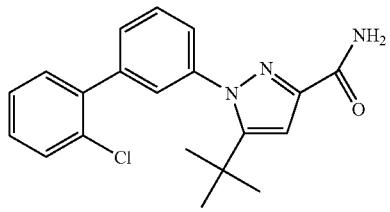

5-tert-butyl-1-(2'-chloro-1,1'-biphenyl-3-yl)-1H-pyrazole-3-carboxamide

A solution of 3-bromophenylhydrazine hydrochloride (0.5 g, 2.2 mmol) and ethyl 5,5-dimethyl-2,4-dioxohexanoate (0.54 g, 2.68 mmol) in acetic acid (10 ml) was refluxed for 16 hours. The reaction was cooled to room temperature, and the solvent was removed under reduced pressure. The residue was partitioned between ethyl acetate and water. The organic layer was washed with water, saturated bicarbonate and brine, and dried over sodium sulfate, filtered and concentrated. The crude material was purified by column chromatography (4.8:0.2 hexanes/ethyl acetate) to give ethyl 1-(3-bromophenyl)-5-tert-butyl-1H-pyrazole-3-carboxylate (0.59 g, 74%) as a syrup.
To a solution of ethyl 1-(3-bromophenyl)-5-tert-butyl-1H-pyrazole-3-carboxylate and 2-chlorophenylboronic acid (0.279 g, 1.78 mmol) in n-propanol:water (2.35 ml:0.482 ml) mixture were added palladium acetate (0.005 g), triphenylphosphine (0.016 g) and 2N sodium carbonate (0.497 ml) and the solution was refluxed for 16 hours. To the reaction, a 2N solution of NaOH (1.5 ml) was added and refluxed for an additional 2 hours. The solution was cooled, acidified with 10% citric acid and extracted into ethyl acetate. The organic phase was washed with brine, dried over sodium sulfate, filtered and concentrated to give 0.212 g of 5-tert-butyl-1-(2'-chloro-1,1'-biphenyl-3-yl)-1H-pyrazole-3-carboxylic acid.

To a solution of the carboxylic acid (0.062 g, 0.17 mmol) in DMF (1 ml) were added pyBOP (0.138 g, 0.26 mmol), HOBT (0.035 g, 0.2 mmol), diethylisopropylamine (0.147 ml, 0.87 mmol) and ammonium chloride (0.056 g, 1.05 mmol). The reaction mixture was stirred at room temperature for 16 hours, then cooled and partitioned between ethylacetate and water. The organic phase was washed with brine, dried over sodium sulfate, filtered and concentrated. Purification of the crude product by silica-gel chromatography (3:2 hexanes/ethylacetate) yielded the product (0.062 g, 64%) as a solid.
¹HNMR (CDCl₃)(δ, ppm): 7.61-7.56 (m, 2H), 7.54-7.49 (m, 2H), 7.43 (d, 1H), 7.38-7.321 (m, 3H), 6.80 (s, 1H), 6.75 (br s, 1H), 5.39 (br s, 1H), 1.26 (s, 9H). MS (ESI): m/e 354.2 (M+1)⁺

EXAMPLE 3

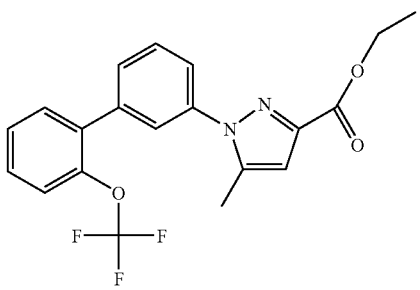

Ethyl-5-methyl-1-[2'-(trifluoromethoxy)-1,1'-biphenyl-3-yl]-1H-pyrazole-3-carboxylate The titled compound was prepared by reacting ethyl 1-(3-bromophenyl)-5-methyl-1H-pyrazole-3-carboxylate (from Step 1 of EXAMPLE 1) with 2-(Trifluoromethoxy)phenylboronic acid (from Step 3 of EXAMPLE 1) under the reaction condition described in Step 4 of EXAMPLE 1.
MS (ESI): m/e 391.0 (M+1)⁺

EXAMPLE 4

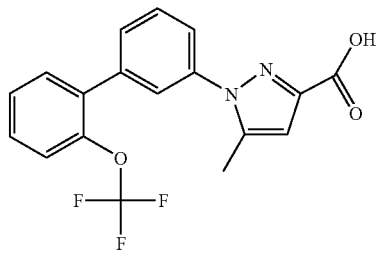

5-Methyl-1-[2'-(trifluoromethoxy)-1,1'-biphenyl-3-yl]-1H-pyrazole-3-carboxylic acid A solution of ethyl-5-methyl-1-[2'-(trifluoromethoxy)-1,1'-biphenyl-3-yl]-1H-pyrazole-3-carboxylate (0.39 g, 1 mmol) (from EXAMPLE 3) in a mixture of MeOH (5 ml) and 2N NaOH (2 ml) was refluxed for 16 hours. The reaction was then cooled, diluted with water, acidified with 10% citric acid and extracted with ethylacetate. The organic phase was washed with water, dried (sodium sulfate) and concentrated in vacuo to give the titled product.

$^1$HNMR (CD$_3$OD)(δ, ppm): 7.64-7.57 (m, 3H), 7.53-7.41 (m, 5H), 6.79 (s, 1H), 2.42 (s, 3H). MS (ESI): m/e 363.0 (M+1)$^+$

EXAMPLE 5

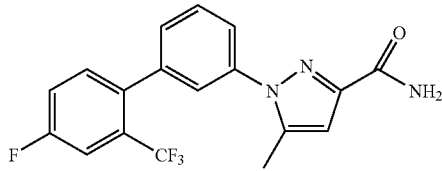

1-[4'-Fluoro-2'-(trifluoromethyl)-1,1'-biphenyl-3-yl]-5-methyl-1H-pyrazole-3-carboxamide To a solution of ethyl 1-(3-bromophenyl)-5-methyl-1H-pyrazole-3-carboxamide (from step 2 of EXAMPLE 1) (0.069 g, 0.24 mmol) in DMSO (1.14 mL), bis(pinacoloato)diboron (0.075 g, 0.3 mmol) was added followed by potassium acetate (0.072 g, 0.74 mmol) and PdCl$_2$(dppf)$_2$ (0.005 g, 3 mol %). The solution was heated in a Smith Creator™ microwave reactor (commercially available from Personal Chemistry, Inc.) at 140° C. for 1200 seconds. The reaction mixture was cooled to room temperature, and 2-bromo-5-fluorobenzotrifluoride (0.12 g, 0.5 mmol), PdCl$_2$(dppf)$_2$ (0.005 g, 3 mol %) and 2M sodium carbonate (0.61 mL, 1.2 mmol) were added to the reaction mixture. The reaction was then subjected to microwave radiation at 140° C. for 2800 seconds. After cooling to room temperature, the reaction mixture was partitioned between EtOAc and water. The organic layer was washed with saturated sodium bicarbonate and brine, then dried over sodium sulfate, filtered and concentrated. Purification of the crude product by reverse phase HPLC (acetonitrile/water system) (gradient: 45% to 100% acetonitrile over 10 minutes) yielded 0.036 mg of the product (41% yield, retention time 5.1 minutes).

$^1$HNMR (CD$_3$OD)(δ, ppm): 7.63-7.59 (m, 3H), 7.49-7.44 (m, 4H), 6.71 (s, 1H), 2.38 (s, 3H). MS (ESI): m/e 363.2 (M+1)$^+$.

The following additional EXAMPLES, summarized in TABLE 1, were prepared using the methods described in EXAMPLES 1-5 above:

TABLE 1

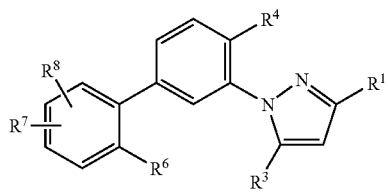

| EX. # | R$^8$ | R$^7$ | R$^6$ | R$^4$ | R$^3$ | R$^1$ | MS (m/e) (M + 1) |
|---|---|---|---|---|---|---|---|
| 6 | H | H | CF$_3$ | H | H | CH$_3$ | 302.9 |
| 7 | H | H | OCF$_3$ | H | H | CH$_3$ | 319.0 |
| 8 | H | H | OCF$_3$ | H | CH$_3$ | H | 318.8 |
| 9 | H | H | CF$_3$ | H | CH$_3$ | H | 303.1 |
| 10 | H | H | CF$_3$ | H | CH$_3$ | CH$_3$ | 316.9 |
| 11 | H | H | OCF$_3$ | H | CH$_3$ | CH$_3$ | 332.8 |
| 12 | H | H | Cl | H | H | CF$_3$ | 323.2 |
| 13 | H | H | Cl | H | CH$_3$ | CONH$_2$ | 312.0 |
| 14 | H | H | CF$_3$ | H | CH$_3$ | CONH$_2$ | 345.9 |
| 15 | H | H | CF$_3$ | H | CH$_3$ | COOCH$_3$ | 361.0 |
| 16 | H | H | CF$_3$ | H | CH$_3$ | COOH | 346.9 |
| 17 | H | H | Cl | H | t-Bu | COOH | 389.2 |
| 18 | H | H | OCF$_3$ | H | CH$_3$ | COOCH$_3$ | 377.1 |
| 19 | H | H | OCF$_3$ | H | CH$_3$ | CONH$_2$ | 362.0 |
| 20 | H | H | OCF$_3$ | H | CH$_3$ | COOH | 363.1 |
| 21 | H | H | OCF$_3$ | H | COOEt | CH$_3$ | 391.2 |
| 22 | H | H | CF$_3$ | H | COOEt | CH$_3$ | 375.0 |
| 23 | H | H | OCF$_3$ | H | COOH | CH$_3$ | 363.1 |
| 24 | H | H | CF$_3$ | H | COOH | CH$_3$ | 347.0 |
| 25 | H | H | OH | H | CH$_3$ | CONH$_2$ | 294.2 |
| 26 | H | H | O-Ph | H | CH$_3$ | COOH | 370.9 |
| 27 | H | H | O-Ph | H | CH$_3$ | COOMe | 385.0 |
| 28 | H | H | O-Ph | H | CH$_3$ | COOEt | 399.2 |
| 29 | H | H | O-Ph | H | CH$_3$ | CONH$_2$ | 370.1 |
| 30 | H | H | CHO | H | CH$_3$ | CONH$_2$ | 306.1 |
| 31 | H | 4-Cl | Cl | H | CH$_3$ | CONH$_2$ | 346.0 |
| 32 | H | 4-CF$_3$ | H | H | CH$_3$ | CONH$_2$ | 346.0 |
| 33 | H | 3-CF$_3$ | H | H | CH$_3$ | CONH$_2$ | 345.8 |
| 34 | 5-Cl | 3-Cl | H | H | CH$_3$ | CONH$_2$ | 346.1 |
| 35 | H | 3-F | H | H | CH$_3$ | CONH$_2$ | 296.0 |
| 36 | 5-CF$_3$ | 3-CF$_3$ | H | H | CH$_3$ | CONH$_2$ | 414.1 |
| 37 | 4-F | 3-Cl | H | H | CH$_3$ | CONH$_2$ | 330.1 |

TABLE 1-continued

| EX. # | R⁸ | R⁷ | R⁶ | R⁴ | R³ | R¹ | MS (m/e) (M + 1) |
|---|---|---|---|---|---|---|---|
| 38 | H | 4-Cl | H | H | CH₃ | CONH₂ | 312.0 |
| 39 | H | 4-F | H | H | CH₃ | CONH₂ | 296.0 |
| 40 | 4-Cl | 3-Cl | H | H | CH₃ | CONH₂ | 346.0 |
| 41 | H | 3-OCH₃ | OCH₃ | H | CH₃ | CONH₂ | 338.2 |
| 42 | H | 3-Cl | CH₃ | H | CH₃ | CONH₂ | 326.0 |
| 43 | H | 5-Cl | OCH₃ | H | CH₃ | CONH₂ | 341.9 |
| 44 | H | H | (2H-tetrazol-5-yl) | H | CH₃ | CONH₂ | 346.0 |
| 45 | H | 3-(1-methyl-1H-pyrazol-3-yl) | H | H | CH₃ | CONH₂ | 344.2 |
| 46 | H | 3-Ph | H | H | CH₃ | CONH₂ | 354.1 |
| 47 | H | H | 1-(4-oxopiperidinyl)methyl | H | CH₃ | CONH₂ | 389.2 |
| 48 | H | 4-CH₂OH | H | H | CH₃ | CONH₂ | 308.1 |
| 49 | H | H | H | H | CH₃ | CONH₂ | 278.0 |
| 50 | H | H | CH₃ | H | CH₃ | CONH₂ | 292.1 |
| 51 | H | 3-COOH | CH₃ | H | CH₃ | CONH₂ | 336.0 |
| 52 | H | 3-F | CH₃ | H | CH₃ | CONH₂ | 310.2 |
| 53 | H | 4-OPh | H | H | CH₃ | CONH₂ | 370.0 |
| 54 | H | 3-Cl | H | H | CH₃ | CONH₂ | 311.8 |
| 55 | H | 3-OEt | H | H | CH₃ | CONH₂ | 322.0 |
| 56 | H | H | F | H | CH₃ | CONH₂ | 295.8 |
| 57 | H | 4-OEt | H | H | CH₃ | CONH₂ | 321.9 |
| 58 | H | 6-F | F | H | CH₃ | CONH₂ | 313.0 |
| 59 | H | 6-CH₃ | CH₃ | H | CH₃ | CONH₂ | 316.1 |
| 60 | H | 4-t-Bu | H | H | CH₃ | CONH₂ | 334.0 |
| 61 | H | 4-OCF₃ | H | H | CH₃ | CONH₂ | 361.9 |
| 62 | H | 4-COCH₃ | H | H | CH₃ | CONH₂ | 320.1 |
| 63 | H | 3-COCH₃ | H | H | CH₃ | CONH₂ | 320.0 |
| 64 | H | 3-CH₃ | CH₃ | H | CH₃ | CONH₂ | 316.0 |
| 65 | H | 4-COOH | H | H | CH₃ | CONH₂ | 321.9 |
| 66 | H | 4-CHO | H | H | CH₃ | CONH₂ | 306.0 |
| 67 | H | 4-CF₃ | CF₃ | H | CH₃ | CONH₂ | 414.0 |
| 68 | H | 6-CF₃ | CF₃ | H | CH₃ | CONH₂ | 413.9 |
| 69 | H | 6-F | CF₃ | H | CH₃ | CONH₂ | 364.1 |
| 70 | H | 5-F | CF₃ | H | CH₃ | CONH₂ | 363.9 |
| 71 | H | 4-Cl | CF₃ | H | CH₃ | CONH₂ | 380.0 |
| 72 | H | 3-Cl | Cl | H | CH₃ | CONH₂ | 346.2 |
| 73 | H | H | OCH₂CF₃ | H | CH₃ | CONH₂ | 376.0 |
| 74 | H | H | OCF₃ | F | CH₃ | COOEt | 425.0 |
| 75 | H | H | OCF₃ | F | CH₃ | CONH₂ | 379.9 |
| 76 | H | H | OCF₃ | F | COOEt | CH₃ | 424.8 |
| 77 | H | H | OCF₃ | F | CONH₂ | CH₃ | 380.1 |
| 78 | H | 3-Cl | Cl | F | CH₃ | CONH₂ | 409.1 |
| 79 | H | 4-CF₃ | CF₃ | F | CH₃ | CONH₂ | 432.1 |
| 80 | H | H | OCF₃ | F | CH₃ | COOH | 381.0 |

TABLE 1-continued

| EX. # | $R^8$ | $R^7$ | $R^6$ | $R^4$ | $R^3$ | $R^1$ | MS (m/e) (M + 1) |
|---|---|---|---|---|---|---|---|
| 81 | H | 5-F | OH | H | $CH_3$ | $CONH_2$ | 312.0 |
| 82 | H | 5-$NMe_2$ | $OCF_3$ | H | $CH_3$ | $CONH_2$ | 405.1 |
| 83 | H | 4-F | $CF_3$ | H | $CH_3$ | COOH | 365.0 |
| 84 | H | 4-$CF_3$ | $CF_3$ | H | $CH_3$ | COOH | 415.0 |
| 85 | H | 4-$CF_3$ | F | H | $CH_3$ | COOH | 364.8 |
| 86 | H | 3-$CF_3$ | $CF_3$ | H | $CH_3$ | COOH | 414.9 |
| 87 | H | H | $OCF_3$ | H | $CH_3$ | $CF_3$ | 386.0 |
| 88 | H | H | $OCF_3$ | H | t-Bu | $CONH_2$ | 404.1 |
| 89 | H | H | $OCF_3$ | H | $OCH_2CH_3$ | $CH_3$ | 363.0 |
| 90 | H | 5-F | $CF_3$ | H | $CH_3$ | COOH | 364.9 |
| 91 | H | 3-Cl | Cl | H | $CH_3$ | COOH | 347.1 |
| 92 | H | 4-Cl | $CF_3$ | H | $CH_3$ | COOH | 337.0 (M − $CO_2$ + 1)$^+$ |
| 93 | H | 3-Cl | Cl | F | $CH_3$ | COOH | 365.0 |
| 94 | H | 6-Cl | Cl | H | $CH_3$ | COOH | 346.9 |
| 95 | H | 6-Cl | Cl | H | $CH_3$ | $CONH_2$ | 346.0 |
| 96 | H | 6-F | $CF_3$ | H | $CH_3$ | COOH | 365.0 |
| 97 | H | H | $CF_3$ | H | $CH_3$ | COOH | 345.9 |
| 98 | H | 6-$CF_3$ | $CF_3$ | H | $CH_3$ | COOH | 415.1 |
| 99 | H | 6-Cl | $CF_3$ | H | $CH_3$ | $CONH_2$ | 380.0 |

The following additional EXAMPLES were also prepared using the methods described in EXAMPLES 1-5 above and are summarized in TABLE 2:

TABLE 2

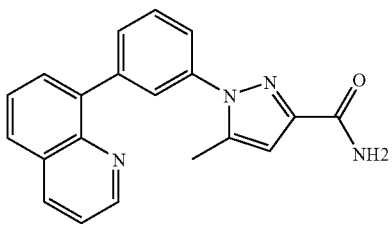

EXAMPLE 100
MS: m/e 329.2 (M + 1)$^+$

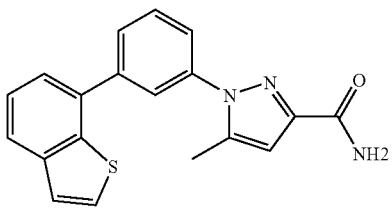

EXAMPLE 101
MS: m/e 334.0 (M + 1)$^+$

TABLE 2-continued

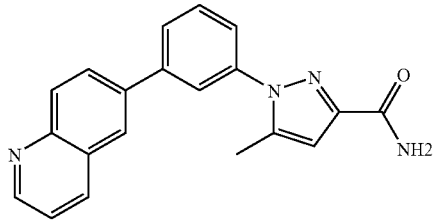

EXAMPLE 102
MS: m/e 329.1 (M + 1)$^+$

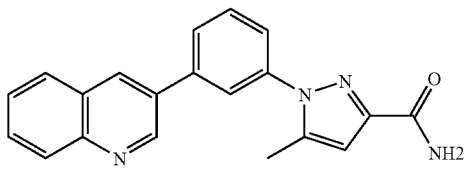

EXAMPLE 103
MS: m/e 328.9 (M + 1)$^+$

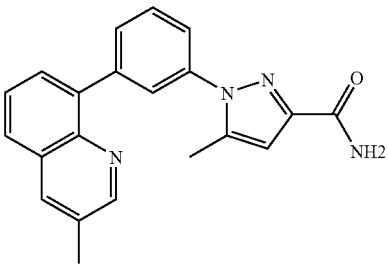

EXAMPLE 104
MS: m/e 343.0 (M + 1)$^+$

TABLE 2-continued

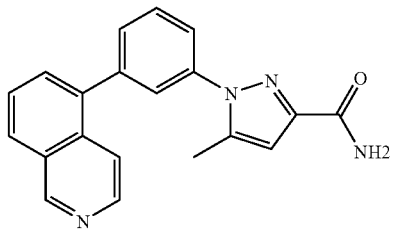

EXAMPLE 105
MS: m/e 329.0 (M + 1)+

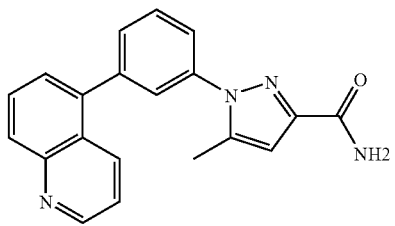

EXAMPLE 106
MS: m/e 329.2 (M + 1)+

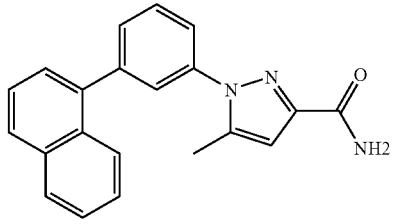

EXAMPLE 107
MS: m/e 328.0 (M + 1)+

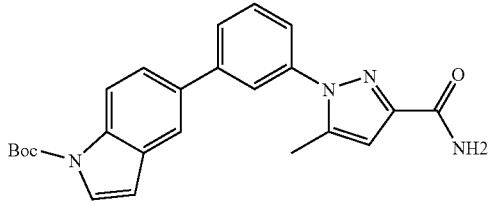

EXAMPLE 108
MS: m/e 417.9 (M + 1)+

EXAMPLE 112

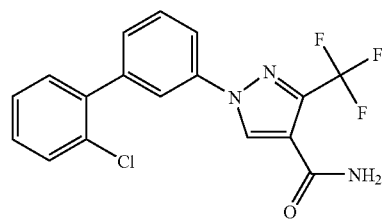

1-(2'-chloro-1,1'-biphenyl-3-yl)-3-(trifluoromethyl)-1H-pyrazole-4-carboxamide

A solution of 3-bromophenylhydrazine hydrochloride (1 g, 4.4 mmol) and ethyl 2-(ethoxymethylene)-4,4,4-trifluoro-3-oxobutyrate (1.16 g, 4.8 mmol) in AcOH (20 ml) was refluxed for 16 hours, and then cooled to room temperature. The solvent was removed under reduced pressure and the residue was partitioned between ethyl acetate and water. The organic layer was washed with water, saturated bicarbonate and brine solution, and then dried over sodium sulfate, filtered and concentrated in vacuo. The crude product obtained was purified by silica-gel column chromatography (using 6% ethyl acetate in hexanes) to give the titled compound (0.75 g, 92%) as a syrup.

To a solution of ethyl 1-(3-bromophenyl)-3-(trifluoromethyl)-1H-pyrazole-4-carboxylate (0.5 g, 1.37 mmol) and 2-chlorophenylboronic acid (0.28 g, 1.78 mmol) in n-propanol:water (2.35 ml:0.482 ml) mixture were added palladium acetate (0.005 g), triphenylphosphine (0.016 g) and 2N sodium carbonate (0.497 ml). The mixture was refluxed for 16 hours. A 2N NaOH (1.5 ml) was then added and refluxing continued for an additional 2 hours. The reaction was cooled, acidified with 10% citric acid and extracted with ethyl acetate. The organic phase was washed with brine, dried over sodium sulfate, filtered and concentrated to give 0.402 g of 1-(3-bromophenyl)-3-(trifluoromethyl)-1H-pyrazole-4-carboxylic acid.

To a solution of the above carboxylic acid (0.103 g, 0.2 mmol) in 1.4 mol of DMF were added pyBOP (0.219 g, 0.42 mmol), HOBT (0.056 g, 0.4 mmol), diethylisopropylethylamine (0.236 ml, 1.4 mmol) and ammonium chloride (0.090 mg, 1.6 mmol), and the mixture was stirred at room temperature for 16 hours. The reaction mixture was then partitioned between ethylacetate and water, and the organic phase was washed with brine, dried over sodium sulfate, filtered and concentrated. Purification of the crude product by silica-gel column chromatography (using 60% ethylacetate in hexanes) yielded the product (0.034 g, 32%) as a solid. $^1$HNMR (CDCl$_3$)($\delta$, ppm): 8.01 (s, 1H), 7.63-7.52 (m, 3H), 7.42 (s, 1H), 7.52-7.48 (m, 1H), 7.45 (d, 1H), 7.38-7.32 (m, 2H).
MS (ESI): m/e 366.2 (M+1)+

EXAMPLE 113

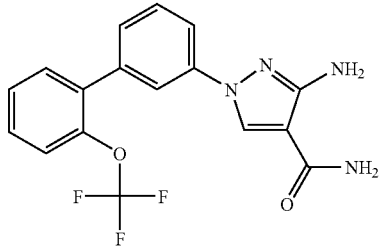

3-Amino-1-[2'-(trifluoromethoxy)-1,1'-biphenyl-3-yl]-1H-pyrazole-4-carboxamide

Step 1: Ethyl 3-amino-1-(3-bromophenyl)-1H-pyrazole-4-carboxylate

To a solution of 3-bromophenylhydrazine hydrochloride (2.25 g, 10.1 mmol) in acetic acid (15.1 mL) and water (5.04 mL) were added ethyl(ethoxymethylene)cyanoacetate (1.88 g, 11.1 mmol) and sodium acetate (3.02 g, 22.2 mmol), and the solution was refluxed for 16 hours. The reaction was cooled and quenched with ice-water. The precipitate formed was filtered, washed with water and dried under vacuum for 24 hours to give 2.95 g of the titled compound (93% yield).

Step 2: Ethyl 3-amino-1-[2'-(trifluoromethoxy)-1,1'-biphenyl-3-yl]-1H-pyrazole-4-carboxylate To a solution of the product from Step 1 (0.452 g, 1.45 mmol) in toluene (4 mL) were added 2-trifluoromethoxyphenylboronic acid (0.450 g, 2.18 mmol), tetrakis(triphenylphosphine)palladium (0.050 g, 3 mol %) and 2M sodium carbonate (1.45 mL, 2.9 mmol). The reaction was refluxed for 16 hours, then cooled and partitioned between EtOAc and water. The organic phase was washed with saturated sodium bicarbonate, brine and dried over sodium sulfate. The filtrate was concentrated in vacuo, and the crude product was purified by silica-gel chromatography using 4% EtOAc in hexanes to yield 0.42 g of the product (73% yield).

$^1$HNMR (CDCl$_3$)($\delta$, ppm): 7.83 (s, 1H), 7.63 (s, 1H), 7.62-7.60 (d, 2H), 7.53-7.39 (m, 5H), 5.39 (s, 2H), 4.34 (q, 2H), 1.39 (t, 3H). MS: m/e: 392.2(M+1)$^+$.

Step 3: 3-Amino-1-[2'-(trifluoromethoxy)-1,1'-biphenyl-3-yl]-1H-pyrazole-4-carboxamide To a solution of the ester from Step 2 (0.215 g, 5.49 mmol) in methanol (2.74 mL) was added 2N NaOH (549 □L, 1.09 mmol), and the mixture was refluxed for 3 hours. The reaction was then cooled, acidified with 10% citric acid and extracted with EtOAc. The organic phase was washed with brine, dried over sodium sulfate, filtered and concentrated to give 0.199 g of the corresponding carboxylic acid which was used as such for the subsequent step.

To a solution of the carboxylic acid (0.186 g, 5.12 mmol) in DMF (2.1 mL) was added 1,1'-carbonyldiimidazole (0.25 g, 1.54 mmol), and the solution was stirred at room temperature for 4 hours. Ammonium acetate (0.5 g, 6.48 mmol) was added and stirring continued for 16 hours at room temperature. The reaction mixture was partitioned between EtOAc and water, and the organic phase was washed with saturated sodium bicarbonate solution, brine, dried over sodium sulfate, filtered and concentrated to give the crude product. Purification using reverse phase HPLC (acetonitrile/water system) (gradient: 10% to 90% acetonitrile over 12 minutes) gave the titled compound (0.036 mg) in 19% yield (retention time 6.53 minutes).

$^1$HNMR (CDCl$_3$)($\delta$, ppm): 7.85 (s, 1H), 7.68-7.65 (m, 2H), 7.58 (t, 2H), 7.53-7.42 (m, 4H). MS (ESI): m/e 363.3(M+1)$^+$.

EXAMPLE 114

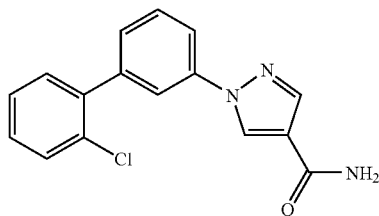

1-(2'-chloro-1,1'-biphenyl-3-yl)-1H-pyrazole-4-carboxamide

Step 1: Ethyl 3-amino-1-(3-bromophenyl)-1H-pyrazole-4-carboxylate

To a solution of 3-bromophenylhydrazine hydrochloride (2.25 g, 10.1 mmol) in 15.1 mL of acetic acid and 5.04 mL of water, ethyl(ethoxymethylene) cyanoacetate (1.88 g, 11.1 mmol) and sodium acetate (3.02 g, 22.2 mmol) were added and the solution was refluxed for 16 hours. The solution was cooled to room temperature and ice water was added. The precipitate formed was filtered, washed with water and dried under vacuum for 24 hours to give 2.95 g of the product (93% yield).

Step 2: Ethyl-1-(3-bromophenyl)-1H-pyrazole-4-carboxylate

To a solution of the ester from Step 1 (0.5 g, 1.61 mmol) in THF (4.3 mL) was added isoamylnitrite (0.434 mL, 3.23 mmol), and the mixture was refluxed for 16 hours. It was cooled to room temperature, concentrated, dried and used as such for the subsequent step without any purification.

Step 3: Ethyl 1-(2'-chloro-1,1'-biphenyl-3-yl)-1H-pyrazole-4-carboxylate

To a solution of the product from Step 2 (0.477 g, 1.6 mmol) in n-propanol (2.76 mL) and water (0.56 mL) were added 2-chlorophenylboronic acid (0.328 g, 2.1 mmol), palladium acetate (0.001 g, 0.3 mol %), triphenylphosphine (0.004 g, 0.9 mol %) and 2M sodium carbonate (0.96 mL, 1.9 mmol), and the reaction was refluxed for 16 hours. The reaction mixture was cooled and partitioned between EtOAc and water. The organic phase was washed with saturated sodium bicarbonate, brine and dried over sodium sulfate. It was then filtered, concentrated and purified by chromatography using 20% EtOAc in hexanes to yield 0.412 g of the product (79%).

Step 4: 1-(2'-chloro-1,1'-biphenyl-3-yl)-1H-pyrazole-4-carboxamide

A solution of the ester from Step 3 (215 mg, 0.6 mmol) in a mixture of methanol (2.19 mL) and 2N NaOH (0.66 mL, 1.3 mmol) was refluxed for 3 hours, then cooled and acidified with 10% citric acid. The mixture was extracted with EtOAc. The organic layer was washed with brine, dried over sodium sulfate, filtered and concentrated to give 0.2 g of the corresponding carboxylic acid.

To a solution of the carboxylic acid (0.2 g, 0.6 mmol) in DMF (2.6 mL) were added PyBOP (0.522 g, 1 mmol), HOBT (0.135 g, 1 mmol), N,N-diisopropylethylamine (0.562 mL, 3.3 mmol) and ammonium chloride (0.071 g, 1.3 mmol), and the mixture was stirred at room temperature for 16 hours. The reaction mixture was partitioned between EtOAc and water, and the organic phase was washed with saturated sodium bicarbonate solution, brine, dried over sodium sulfate, filtered and concentrated to give the crude product, which was purified by flash chromatography using 30% EtOAc in hexanes to give 0.125 g of the titled product (63%).

$^1$HNMR (CD$_3$)$_2$SO)($\delta$, ppm): 8.9 (s, 1H), 8.15 (s, 1H), 7.84 (d, 2H), 7.62-7.58 (m, 2H), 7.52-7.39 (m, 4H). MS (ESI): m/e 298.3 (M+1)$^+$.

The following additional EXAMPLES (summarized in TABLE 3) were prepared using the methods described in EXAMPLES 113 and 114 above:

TABLE 3

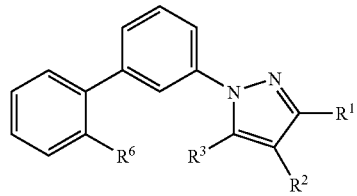

| EX. # | R$^6$ | R$^3$ | R$^2$ | R$^1$ | MS: m/e (M + 1) |
|---|---|---|---|---|---|
| 115 | Cl | H | CONH-t-Bu | H | 354.1 |
| 116 | Cl | H | CONH-Me | H | 311.0 |

TABLE 3-continued

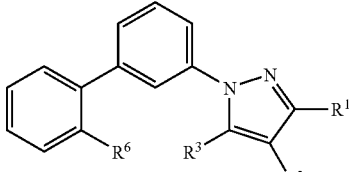

| EX. # | R⁶ | R³ | R² | R¹ | MS: m/e (M + 1) |
|---|---|---|---|---|---|
| 117 | Cl | H | 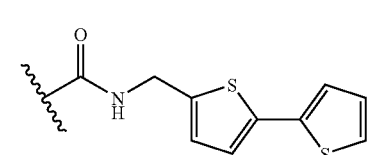 | H | 476.0 |
| 118 | Cl | H | 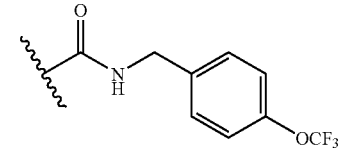 | H | 471.9 |
| 119 | CF₃ | H | COOEt | NH₂ | 376.1 |
| 120 | CF₃ | H | COOH | H | 332.8 |
| 121 | OCF₃ | H | COOEt | H | 377.0 |
| 122 | OCF₃ | H | COOH | NH₂ | 364.0 |

EXAMPLE 123

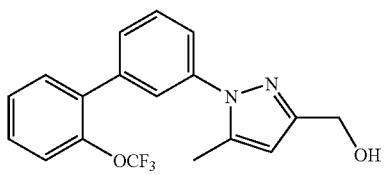

{5-Methyl-1-[2'-(trifluoromethoxy)-1,1'-biphenyl-3-yl]-1H-pyrazol-3-yl}methanol

To a cold (0° C.) solution of ethyl-5-methyl-1-[2'-(trifluoromethoxy)-1,1'-biphenyl-3-yl]1H-pyrazole-3-carboxylate (EXAMPLE 3) (1.1 g, 2.82 mmol) in anhydrous dichloromethane (10 mL) was added DIBAL-H in toluene solution (1.0M, 6.8 mL, 6.8 mmol). The reaction was stirred at 0° C. for 30 minutes, then 0.5 mL of methanol was added. The reaction was warmed up to room temperature, and stirred continuously for another 30 minutes. After the addition of 5 g of Celite and 5 g of anhydrous MgSO₄, the saturated NH₄Cl aqueous was added dropwise. The resulting slurry was stirred vigorously for an hour. Then the mixture was filtered and concentrated to give the crude product. The crude alcohol obtained was purified by flash-column chromatography on silica-gel to provide the pure titled product as a yellow oil (0.9 g, 93% yield).

¹H NMR (CDCl₃) (δ, ppm): 7.52-7.35 (m, 8H), 6.19 (s, 1H), 4.69 (s, 2H), 2.34 (s, 3H). MS (ESI): m/e 348.9 (M+1)⁺

EXAMPLE 124

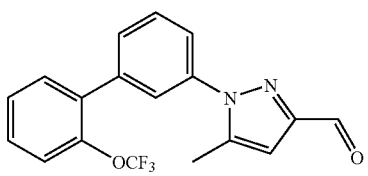

5-Methyl-1-[2'-(trifluoromethoxy)-1,1'-biphenyl-3-yl]-1H-pyrazole-3-carbaldehyde To a solution of ethyl 5-methyl-1-[2'-(trifluoromethoxy)-1,1'-biphenyl-3-yl]-1H-pyrazole-3-carboxylate (from EXAMPLE 3) (1.1 g, 2.82 mmol) in anhydrous dichloromethane (10 mL) was added DIBAL-H in toluene solution (1.0M, 6.8 mL, 6.8 mmol) at −78° C. After stirring for 20 min at that temperature, the reaction was quenched with methanol as described above in EXAMPLE 123. Further work-up and purification, as described in EXAMPLE 123, produced the titled compound.

¹H NMR (CDCl₃) (δ, ppm): 7.52-7.35 (m, 8H), 6.19 (s, 1H), 4.69 (s, 2H), 2.34 (s, 3H). MS (ESI): m/e 347 (M+1)⁺

EXAMPLE 125

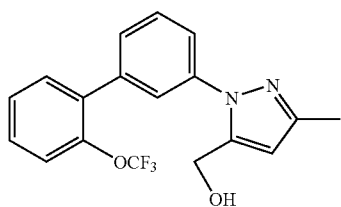

{3-Methyl-1-[2'-(trifluoromethoxy)-1,1'-biphenyl-3-yl]-1H-pyrazol-5-yl}methanol

The titled compound was prepared by reacting ethyl 3-methyl-1-[2'-(trifluoromethoxy)-1,1'-biphenyl-3-yl]-1H-pyrazole-5-carboxylate (EXAMPLE 21) with DIBALH in a manner described in EXAMPLE 123. MS (ESI): m/e 349 (M+1)$^+$ The following additional EXAMPLES (summarized in TABLES 4 and 5) were prepared from the products of EXAMPLES 123 and 124 using the methods described above.

TABLE 4

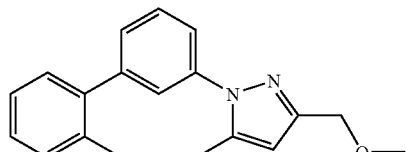

EXAMPLE 126
MS (ESI): m/e 362.9 (M + 1)$^+$

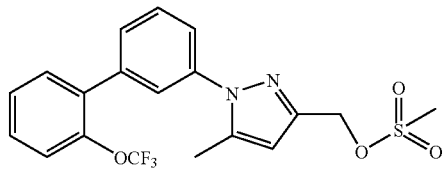

EXAMPLE 127
MS (ESI): m/e 427.0 (M + 1)$^+$

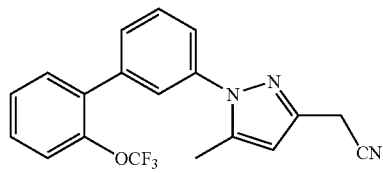

EXAMPLE 128
MS (ESI): m/e 358.1 (M + 1)$^+$

TABLE 5

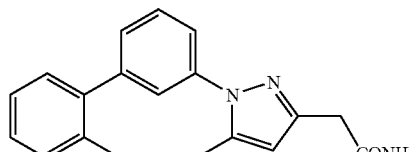

EXAMPLE 129
MS (ESI): m/e 375.9 (M + 1)$^+$

TABLE 5-continued

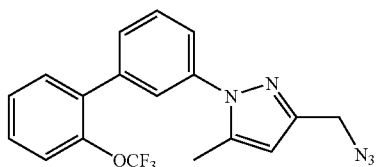

EXAMPLE 130
MS (ESI): m/e 374.0 (M + 1)$^+$

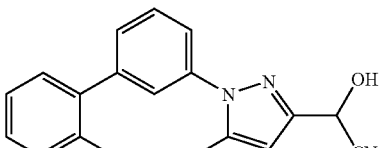

EXAMPLE 131
MS (ESI): m/e 374.0 (M + 1)$^+$

EXAMPLE 132

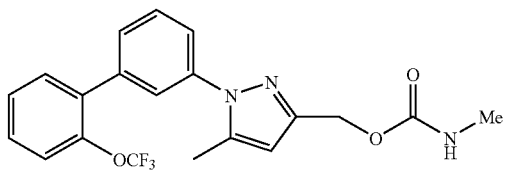

{5-Methyl-1-[2'-(trifluoromethoxy)-1,1'-biphenyl-3-yl]-1H-pyrazol-3-yl}methyl methylcarbamate To the solution of the alcohol from EXAMPLE 123 (0.050 g, 0.14 mmol) in dry dichloromethane (3 mL) was added 1,1'-carbonyldiimidazole (0.023 g, 0.14 mmol). The reaction solution was stirred at room temperature for one hour before the methylamine was added. The reaction was then stirred at the same temperature for overnight. The reaction was quenched with 10% HCl aqueous, and extracted with dichloromethane (3 times). The combined organic layer was washed with brine, and dried over anhydrous sodium sulfate. The product was purified via a column chromatography on silica gel. The carbamate was obtained as a white solid, 0.0565 g, 97% yield.

$^1$H NMR (CDCl$_3$) (δ, ppm): 7.56-7.37 (m, 10H), 6.37 (s, 1H), 5.59 (s, 2H), 2.36 (s, 3H). MS (ESI): m/e 428.0 (M+Na)$^+$

EXAMPLE 133

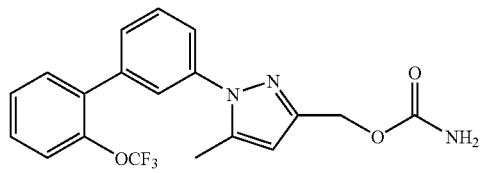

{5-Methyl-1-[2'-(trifluoromethoxy)-1,1'-biphenyl-3-yl]-1H-pyrazol-3-yl}methyl carbamate To the solution of the alcohol from EXAMPLE 123 (0.050 g, 0.14 mmol) in ethanol (2 mL) was added tirmethylsilyisocyanate (0.023 g, 0.14 mmol). The reaction solution was refluxed for two hours. The reaction was cooled to room temperature, and concentrated. The product was purified via a column chromatography on silica gel. The carbamate was obtained as a white solid, 0.055 g, 97% yield.

$^1$H NMR (CDCl$_3$) (δ, ppm): 7.68-7.24 (m, 9H), 6.20 (s, 1H), 5.15 (bs, 1H), 4.70 (s, 2H), 2.35 (s, 3H). MS (ESI): m/e 349.9 (M-CONH$_2$+1)$^+$ The following additional EXAMPLES (summarized in TABLE 6) were prepared using the methods described in EXAMPLE 132 above.

TABLE 6

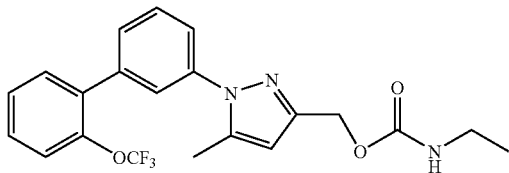

EXAMPLE 134
MS (ESI): m/e 442.0 (M + Na)$^+$

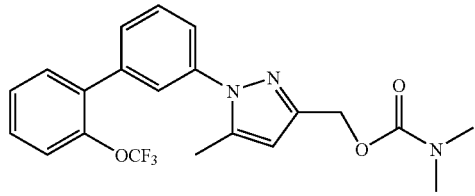

EXAMPLE 135
MS (ESI): m/e 442.0 (M + Na)$^+$

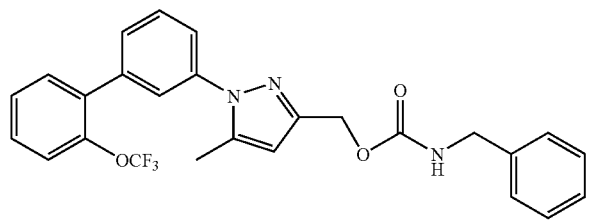

EXAMPLE 136
MS (ESI): m/e 399.9 (M − NHBn + Na)$^+$

EXAMPLE 137

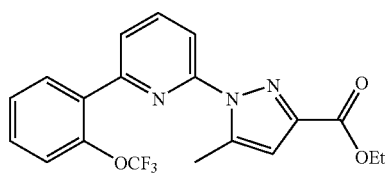

Ethyl 5-methyl-1-{6-[2-(trifluoromethoxy)phenyl] pyridin-2-yl}-1H-pyrazole-3-carboxylate
Step 1:

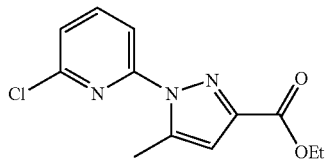

Ethyl 1-(6-chloropyridin-2-yl)-5-methyl-1H-pyrazole-3-carboxylate

To the solution of 2-chloro-6-pyridinehydrazine (0.23 g, 1.6 mmol) in acetic acid (5 mL) was added ethyl 2,4-dioxy-valerate (0.278 g, 1.78 mmol). The reaction was stirred at room temperature for 12 hours. The reaction was concentrated, and the residue was taken by ethyl acetate, and washed with 0.5N HCl, brine. The crude product obtained was purified by flash-column chromatography on silica gel to provide the pure pyrazole as a white solid, 0.165 g, 38% yield. Its corresponding regioisomer was also isolated as a white solid, 0.214 g (50%).

$^1$H NMR (CDCl$_3$) (δ, ppm): 8.01 (d, J=8 Hz, 1H), 7.84 (t, J=9 Hz, 1H), 7.32 (d, J=8 Hz, 1H), 6.74 (s, 1H), 4.46 (q, J=7.5, 21.5 Hz, 2H), 2.76 (s, 3H), 1.46 (t, J=7.0 Hz, 3H). MS (ESI): m/e 266.0 (M+1)$^+$ Step 2:

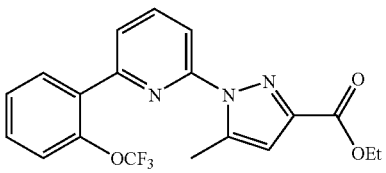

Ethyl 5-methyl-1-{6-[2-(trifluoromethoxy)phenyl] pyridin-2-yl}-1H-pyrazole-3-carboxylate To the solution of 2-trifluoromethoxyphenyl boronic acid (0.192 g, 0.92 mmol) and the 2-chloropyridine compound from Step 1 (0.165 g, 0.62 mmol) in toluene:n-propanol (3 mL:3 mL) were added tetrabis(triphenylphosphine)palladium (0.072 g, 0.062 mmol) and aqueous sodium bicarbonate (2.0M, 0.62 mL, 1.2 mmol). The reaction mixture was stirred at 90° C. for 16 hours. After cooling to room temperature, the mixture was filtered through a Celite pad, and washed with ethyl acetate (3 times). The filtrate was concentrated. The resulting residue was dissolved in ethyl acetate and washed with saturated sodium carbonate aqueous solution and brine, the organic layer was dried over anhydrous sodium sulfate. After concentration, the crude product was applied to column chromatography on silica gel to afford the titled compound, as yellow oil, 30 mg, 12.3% yield.

$^1$H NMR (CDCl$_3$) (δ, ppm): 7.95-7.90 (m, 2H), 7.71 (m, 2H), 7.46-7.29 (m, 3H), 6.69 (s, 1H), 4.20 (q, J=7.5, 21.5 Hz, 2H), 2.41 (s, 3H), 1.51 (t, J=7.0 Hz, 3H). MS (ESI): n/e 413.6 (M+Na)$^+$

EXAMPLE 138

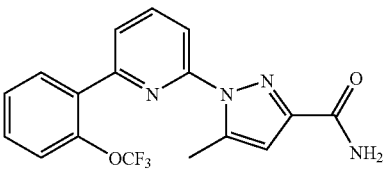

5-methyl-1-{6-[2-(trifluoromethoxy)phenyl]pyridin-2-yl}-1H-pyrazole-3-carboxamide A solution of the ester from Step 2 of EXAMPLE 137 (0.025 g, 0.064 mmol) in ammonium-methanol solution (7.0M, 3 mL) (placed in a sealed tube) was stirred at 70° C. for 2 days. After cooling, the reaction was concentrated to give the titled compound as yellow powder (0.02 g).

¹H NMR (CDCl₃) (δ, ppm): 7.94-7.77 (m, 3H), 7.60 (d, J=5 Hz, 1H), 7.46-7.35 (m, 3H), 6.79 (s, 1H), 5.64 (bs, 1H), 5.40 (bs, 1H), 2.35 (s, 3H). MS (ESI): m/e 363.1 (M+1)⁺

EXAMPLE 139

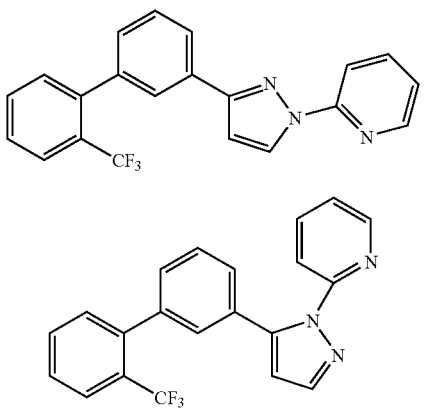

2-{3-[2'-(trifluoromethyl)-1,1'-biphenyl-3-yl]-1H-pyrazol-1-yl}pyridine: (A)

2-{5-[2'-(trifluoromethyl)-1,1'-biphenyl-3-yl]-1H-pyrazol-1-yl}pyridine: (B)

Step 1: 3-(dimethylamino)-1-[2'-(trifluoromethyl)-1,1'-biphenyl-3-yl]prop-2-en-1-one To a solution of 1-(2'-trifluoromethyl-1,1'-biphenyl-3-yl)ethanone (0.325 g, 1.3 mmol) in DMF (1.45 mL) was added 1,1-dimethoxy-N,N-dimethylmethanamine (0.18 mL, 1.43 mL), and the solution was heated in a Smith Creator™ microwave reactor (commercially available from Personal Chemistry, Inc.) at 165° C. for 1200 seconds. The mixture was cooled to room temperature, partitioned between EtOAc and water, washed with brine, dried over sodium sulfate filtered and concentrated to give 0.395 g of the crude product (95%) (which was used as such for the subsequent step.

Step 2: 2-{3-[2'-(trifluoromethyl)-1,1'-biphenyl-3-yl]-1H-pyrazol-1-yl}pyridine: (A) and 2-{5-[2'-(trifluoromethyl)-1,1'-biphenyl-3-yl]-1H-pyrazol-1-yl}pyridine: (B)

To a solution of the product from Step 1 (0.224 g, 0.7 mmol) in ethanol (3.5 mL) was added 2-hydrazinopyridine (0.076 g, 0.7 mmol) and the solution was refluxed for 16 hours. The reaction was cooled, diluted with EtOAc, washed with saturated sodium bicarbonate, brine and dried over sodium sulfate. The organic phase was filtered, concentrated, and the crude product was purified by reverse phase HPLC (acetonitrile/water system) (gradient: 30% to 100% acetonitrile over 12 minutes) to give product A (0.033 g, 29% yield, retention time 5.28 minutes) and the regioisomeric product B (0.021 g, 18% yield, retention time 7.25 minutes).

Product A: ¹HNMR (CD₃OD)(δ, ppm): 8.39 (s, 1H), 7.93 (t, 1H), 7.79 (s, 1H), 7.73 (d, 1H), 7.60 (t, 1H), 7.52 (t, 1H), 7.49 (d, 1H), 7.48-7.39 (m, 3H), 7.34 (d, 1H), 7.28 (d, 1H), 7.09 (s, 1H), 6.67 (s, 1H). MS (ESI): m/e 366.5 (M+1)⁺.

Product B: ¹HNMR (CD₃OD)(δ, ppm): 8.63 (s, 1H), 8.43 (d, 1H), 8.06 (d, 1H), 8.00 (d, 1H), 7.97 (t, 1H), 7.90 (s, 1H), 7.82 (d, 1H), 7.69 (t, 1H), 7.58 (t, 1H), 7.58 (t, 1H), 7.50 (t, 1H), 7.45 (d, 1H), 7.33-7.30 (m, 2H), 6.94 (s, 1H). MS (ESI): m/e 366.2 (M+1)⁺.

EXAMPLE 140

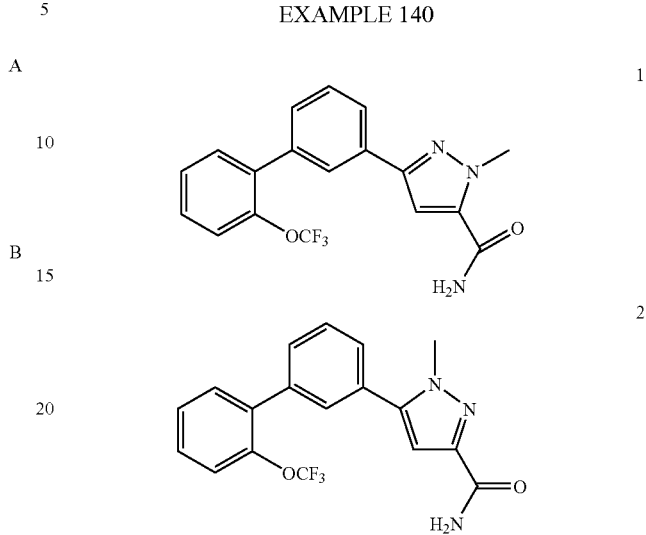

1-methyl-3-[2'-(trifluoromethyl)-1,1'-biphenyl-3-yl]-1H-pyrazole-5-carboxamide (1)

1-methyl-5-[2'-(trifluoromethyl)-1,1'-biphenyl-3-yl]-1H-pyrazole-3-carboxamide (2)

Step 1: Ethyl 3-(3-bromophenyl)-3-oxopropanoate

To a suspension of sodium hydride (0.361 g, 9 mmol) in DMF (9.4 mL) was added 3-bromoacetophenone (0.99 mL, 9.53 mmol) at 0° C. and stirred at room temperature for 35 minutes. The reaction mixture was then cooled to 0° C. and diethyloxalate (1.32 mL, 9.7 mmol) was added followed by stirring at room temperature for 16 hours. The reaction was then poured into ice-water and acidified with 1N HCl. The solid precipitate formed was filtered, washed with cold water and dried under vacuum to give the titled product (2.1 g, 93%) as a yellow solid.

Step 2: Ethyl 3-(3-bromophenyl)-1-methyl-1H-pyrazole-5-carboxylate (3)

Ethyl 5-(3-bromophenyl)-1-methyl-1H-pyrazole-3-carboxylate: (4)

A solution of ethyl-3-(3-bromophenyl)-3-oxopropanoate from Step 1 (1 g, 3.3 mmol) in ethanol (16.5 mL) and methyl hydrazine (0.177 ml, 3.3 mmol) was refluxed for 16 hours. The reaction was cooled, diluted with EtOAc and washed with saturated sodium bicarbonate, water, brine, then dried over sodium sulfate, filtered and concentrated. The crude product was purified by silica-gel chromatography using 20% EtOAc in to give the two regioisomeric pyrazole esters 3 and 4.

Product 3: ¹HNMR (CDCl₃)(δ, ppm): 7.98 (s, 1H), 7.73 (d, 1H), 7.46 (d, 1H), 7.31 (s, 1H), 7.14 (s, 1H), 4.40 (q, 2H), 4.25 (s, 3H), 1.43 (t, 3H). MS (ESI): m/e 309.2 (M+1)⁺.

Product 4: ¹HNMR (CDCl₃)(δ, ppm): 7.61 (s, 2H), 7.38 (m, 2H), 6.8 (s, 1H), 4.45 (q, 2H), 3.98 (s, 3H), 1.43 (t, 3H). MS (ESI): m/e 309.2 (M+1)⁺.

Step 3: 3-(3-bromophenyl)-1-methyl-1H-pyrazole-5-carboxamide (5)

5-(3-bromophenyl)-1-methyl-1H-pyrazole-3-carboxamide (6)

A solution of 3 from Step 2 (0.090 g, 0.29 mmol) in methanol was saturated with ammonia gas, placed in a sealed tube and stirred at room temperature for 48 hours. The reaction was then concentrated and dried under vacuum to give 0.086 g of the titled product 5 (95% yield). The product 6 was prepared similarly from 4.

Step 4: 1-Methyl-3-[2'-(trifluoromethoxy)-1,1'-biphenyl-3-yl]-1H-pyrazole-5-carboxamide (1)

1-Methyl-5-[2'-(trifluoromethoxy)-1,1'-biphenyl-3-yl]-1H-pyrazole-3-carboxamide (2)

The carboxamide 5 (0.042 g, 0.1 mmol) was reacted with 2-trifluoromethoxyphenyl boronic acid as described in Step 2 of EXAMPLE 137. The crude product obtained was purified on silica-gel chromatography using (3.5:1.5; hexanes/EtOAc) to yield 0.025 g (54%) of the titled product 1.
$^1$HNMR (CD$_3$OD)(δ, ppm): 7.89 (s, 1H), 7.82 (d, 1H), 7.55-7.42 (m, 6H), 7.20 (s, 1H), 4.18 (s, 3H). MS (ESI): m/e 362.1 (M+1)$^+$ The titled product 2 was obtained similarly from the carboxamide 6 (Step 3).
$^1$HNMR (CD$_3$OD)(δ, ppm): 7.62-7.55 (m, 5H), 7.50-7.44 (m, 3H), 6.84 (s, 1H), 3.96(s, 3H). MS (ESI): m/e 362.1 (M+1)$^+$.

EXAMPLE 141

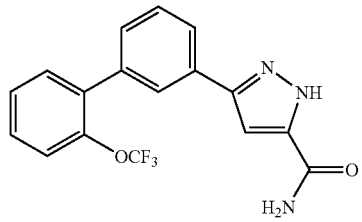

3-[2'-(trifluoromethoxy)-1,1'-biphenyl-3-yl]-1H-pyrazole-5-carboxamide

Step 1: Ethyl 3-oxo-3-[2'-(trifluoromethoxy)-1,1'-biphenyl-3-yl]propanoate

A solution of 1-(2'-trifluoromethoxy-1,1'-biphenyl-3-yl)ethanone (0.63 g, 2.3 mmol) in DMF (3 mL) at 0° C. was treated with sodium hydride and stirred at room temperature for 10 minutes. Diethyloxalate (0.4 mL, 2.9 mmol) was then added and stirring continued at room temperature for 16 hours. The reaction mixture was poured into ice cold water, acidified with 1N HCl, and the solid formed was filtered and dried in vacuo to give the titled product (0.80 g, 91% yield).

Step 2: Ethyl 3-[2'-(trifluoromethoxy)-1,1'-biphenyl-3-yl]-1H-pyrazole-5-carboxylate A mixture of the ester from Step 2 (0.23 g, 0.6 mmol), ethanol (2 mL) and hydrazine hydrate (0.026 mL, 0.9 mmol) was refluxed for 16 hours, then cooled to room temperature and partitioned between EtOAc and water. The organic phase was washed with saturated sodium bicarbonate, brine, dried over sodium sulfate, filtered and concentrated. Purification of the crude product by chromatography using 20% EtOAc in hexanes gave the titled product (0.095 g, 42%) as a solid.
$^1$HNMR (CD$_3$OD)(δ, ppm): 7.88 (s, 1H), 7.81 (d, 1H), 7.57-7.43 (m, 6H), 7.18 (s, 1H), 4.40 (q, 2H), 1.40 (t, 3H). MS (ESI): m/e 377.5 (M+1)$^+$.

Step 3: 3-[2'-(trifluoromethoxy)-1,1'-biphenyl-3-yl]-1H-pyrazole-5-carboxamide

The pyrazole ester (47 mg, 0.1 mmol) from Step 2 was treated with ammonia gas in a sealed tube as described in Step 2 of EXAMPLE 140 to provide the titled compound, after purification by reverse phase HPLC (acetonitrile/water system) (gradient: 40% to 100% acetonitrile over 11 minutes) in 74% yield (0.036 g, retention time 6.57 minutes).
$^1$HNMR (CD$_3$OD)(δ, ppm): 7.84 (s, 1H), 7.77 (d, 1H), 7.57-7.53 (m, 2H), 7.49-7.42 (m, 3H), 7.12 (s, 1H). MS (ESI): m/e 348.1 (M+1)$^+$.

The following additional EXAMPLES (summarized in TABLE 7) were prepared using the methods described in EXAMPLE 141.

TABLE 7

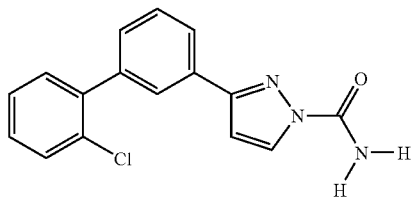

EXAMPLE 142
MS (ESI): m/e 298.0

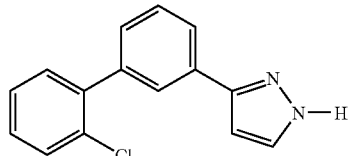

EXAMPLE 143
MS (ESI): m/e 254.9

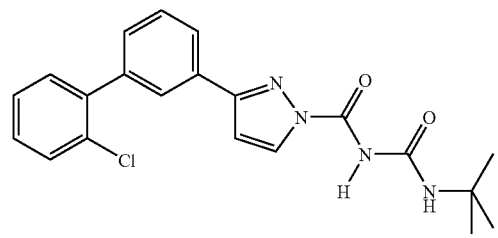

EXAMPLE 144
MS (ESI): m/e 397.0

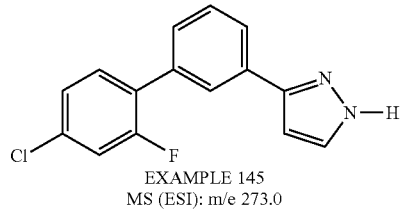

EXAMPLE 145
MS (ESI): m/e 273.0

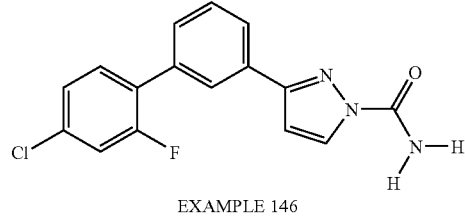

EXAMPLE 146
MS (ESI): m/e 316.0

Further examples of the present invention are summarized in TABLE 8.

TABLE 8
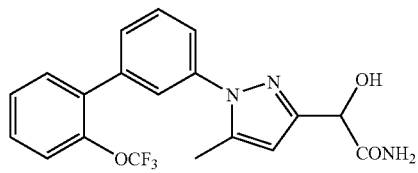
EXAMPLE 147
MS (ESI): m/e 391.9 (M + 1)+
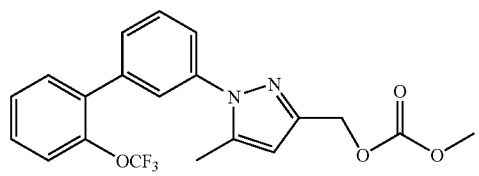
EXAMPLE 148
MS (ESI): m/e 348.2 (M − OCOOMe + 1)+
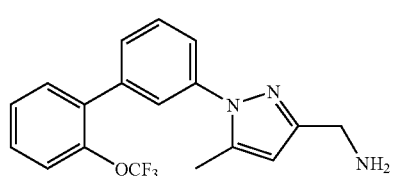
EXAMPLE 149
MS (ESI): m/e 348.1 (M + 1)+
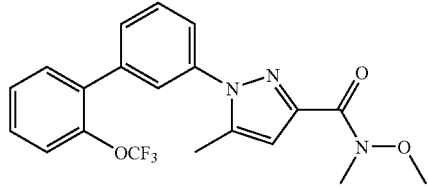
EXAMPLE 150
MS (ESI): m/e 406.0 (M + 1)+
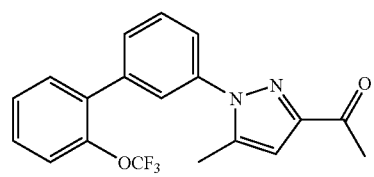
EXAMPLE 151
MS (ESI): m/e 360.9 (M + 1)+
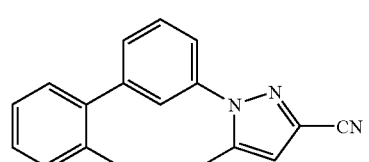
EXAMPLE 152
MS (ESI): m/e 344.0 (M + 1)+
TABLE 8-continued
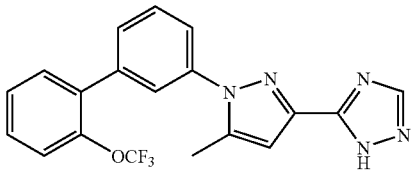
EXAMPLE 153
MS (ESI): m/e 385.9 (M + 1)+
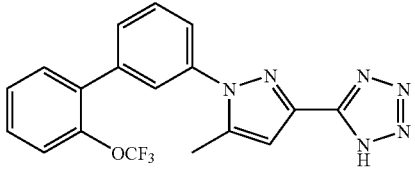
EXAMPLE 154
MS (ESI): m/e 388.0 (M + 1)+
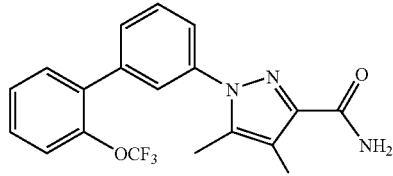
EXAMPLE 155
MS (ESI): m/e 440.0 (M + 1)+
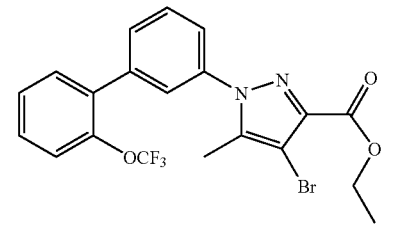
EXAMPLE 156
MS (ESI): m/e 469.1 (M + 1)+
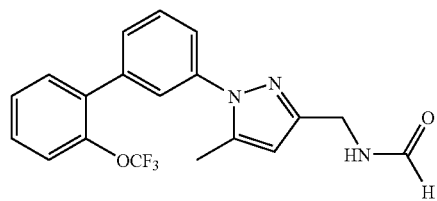
EXAMPLE 157
MS (ESI): m/e 375.9 (M + 1)+
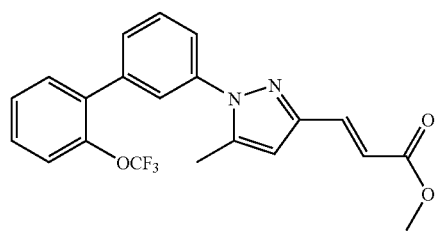
EXAMPLE 158
MS (ESI): m/e 403.0 (M + 1)+

TABLE 8-continued

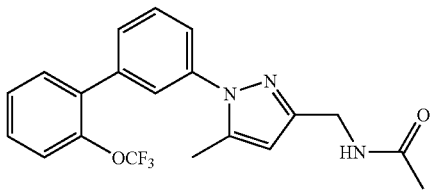

EXAMPLE 159
MS (ESI): m/e 390.0 (M + 1)+

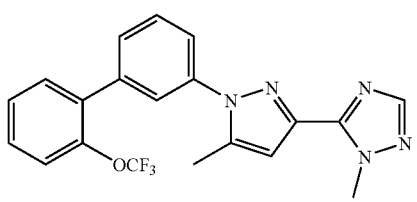

EXAMPLE 160
MS (ESI): m/e 399.9 (M + 1)+

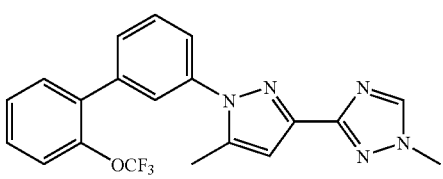

EXAMPLE 161
MS (ESI): m/e 400.0 (M + 1)+

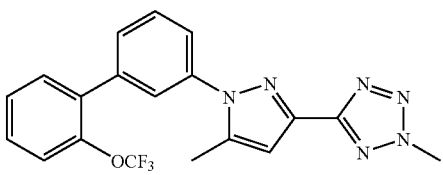

EXAMPLE 162
MS (ESI): m/e 401.1 (M + 1)+

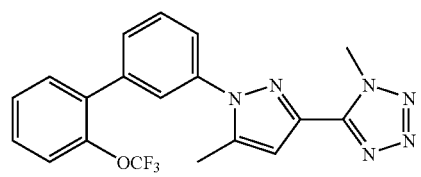

EXAMPLE 163
MS (ESI): m/e 401.0 (M + 1)+

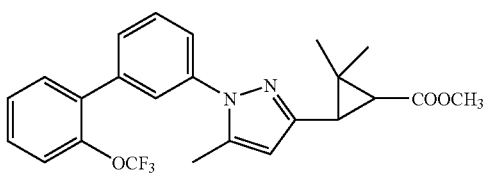

EXAMPLE 164
MS (ESI): m/e 445.2 (M + 1)+

EXAMPLE 165

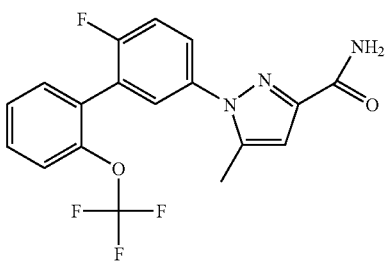

1-[6-fluoro-2'-(trifluoromethoxy)-1,1'-biphenyl-3-yl]-5-methyl-1H-pyrazole-3-carboxamide Step 1:

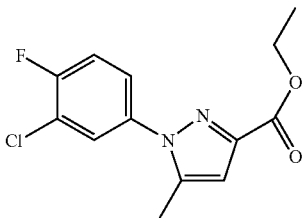

Ethyl-1-(3-Chloro-4-fluorophenyl)-5-methyl-1H-pyrazole-3-carboxylate

A solution of 3-chloro-4-fluorophenylhydrazine (2 g, 12.4 mmol) and ethyl-2,4-dioxovalerate (2.36 g, 14.9 mmol) in ethanol (40 ml) was refluxed for 16 hours, then cooled to room temperature and partitioned between EtOAc and water. The organic layer was washed with saturated bicarbonate, brine solution, dried over sodium sulfate, filtered, concentrated and purified by silica-gel column chromatography using 4% EtOAc in heaxanes to give the product (2.45 g, 71%) as a solid.

$^1$HNMR (CD$_3$OD)(δ, ppm): 7.76 (dd, 1H), 7.56-7.53 (m, 1H), 7.47 (t, 1H), 6.77 (s, 1H), 4.37 (q, 2H), 2.23 (s, 3H), 1.39 (t, 3H). MS (ESI): m/e 283.1 (M+1)+.

Step 2:

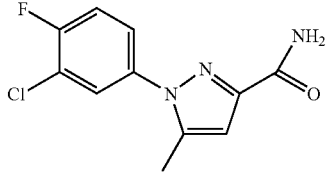

1-(3-Chloro-4-fluorophenyl)-5-methyl-1H-pyrazole-3-carboxamide

Ammonia gas was bubbled into a chilled solution of ethyl 1-(3-chloro-4-fluorophenyl)-5-methyl-1H-pyrazole-3-carboxylate (from Step 1) (1.0 g, 3 mmol) in MeOH (1.5 ml) for 5 minutes. The resulting mixture was placed in a sealed tube and stirred at room temperature for 2 days. The reaction was then concentrated in vacuo, and the residue obtained was dried under vacuum to give titled product (0.72 g, 80%) as a solid.

$^1$HNMR (CD$_3$OD)(δ, ppm): 7.79 (dd, 1H), 7.58-7.54 (m, 1H), 7.45 (t, 1H), 6.71 (s, 1H), 2.39 (s, 3H). MS (ESI): m/e 254.2 (M+1)$^+$.

Step 3: 1-[6-fluoro-2'-(trifluoromethoxy)-1,1'-biphenyl-3-yl]-5-methyl-1H-pyrazole-3-carboxamide To a solution of the carboxamide (from step 2) (0.063 g, 0.2 mmol) and 2-trifluromethoxyphenyl boronic acid (0.076 g, 0.37 mmol) in dioxane (1 mL) were added NiCl$_2$(dppf)$_2$ (0.002 g, 1 mole %) and potassium phosphate (0.158 g, 0.74 mmol) and the mixture was stirred at 95° C. for 16 hours. After cooling, the reaction was partitioned between EtOAc and water. The organic phase was washed with saturated sodium bicarbonate, brine and then dried over sodium sulfate. The crude product, obtained upon concentration of the organic phase, was purified by reverse phase HPLC (acetonitrile/water system) (gradient: 10% to 90% acetonitrile over 10 minutes) to yield the titled product (0.009 g, 9.5%).

$^1$HNMR (CD$_3$OD)(□, ppm): 7.66-7.63 (m, 1H), 7.58-7.39 (m, 6H), 6.71 (s, 1H), 2.37 (s, 3H). MS (ESI): m/e 380.1 (M+1)$^+$.

The following amide analogs (TABLE 9) were prepared using Step 2 of EXAMPLE 1, replacing ammonium acetate with an appropriate amine.

TABLE 9

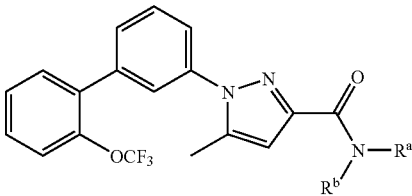

| EXAMPLE # | R$^a$ | R$^b$ | MS: m/e (M + 1) |
|---|---|---|---|
| 166 | —CH$_2$CH$_2$OH | H | 406.0 |
| 167 | —CH$_2$CH$_2$CH$_2$OH | H | 420.1 |
| 168 | —CH(CH$_2$OH)$_2$ | H | 436.0 |
| 169 | —CH$_3$ | H | 375.9 |
| 170 | —CH$_2$CH$_3$ | H | 391.0 |
| 171 | (3-methyl-1H-1,2,4-triazol-5-yl)methyl | H | 457.0 |
| 172 | (1-methyl-1H-pyrazol-4-yl)methyl | H | 456.1 |
| 173 | (1H-pyrazol-5-yl)methyl | H | 442.0 |
| 174 | (1H-pyrazol-4-yl)methyl | H | 443.1 |

TABLE 9-continued

| EXAMPLE # | R$^a$ | R$^b$ | MS: m/e (M + 1) |
|---|---|---|---|
| 175 | (4-methyl-1,2,5-oxadiazol-3-yl)methyl | H | 458.0 |
| 176 | (5-oxo-4,5-dihydro-1H-1,2,4-triazol-3-yl)methyl | CH$_3$ | 473.0 |
| 177 | 2-(1-methyl-1H-pyrazol-4-yl)ethyl | CH$_3$ | 484.2 |
| 178 | (1,3-thiazol-5-yl)methyl | H | 459.0 |

EXAMPLE 179

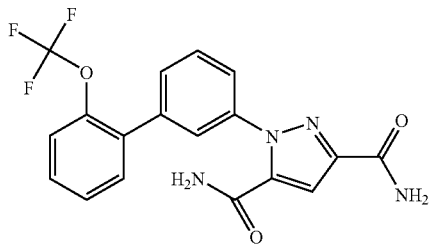

Step 1: Diethyl-1-(3-bromophenyl)-1H-pyrazole-3,5-dicarboxylate

A mixture of diethyl-3,5-pyrazoledicarboxylate (1.0 g, 4.71 mmol), 3-bromophenylboronicacid (1.89 g, 9.42 mmol) and di-Micron-hydroxo-bis[(N,N,N',N'-tetramethylethylenediamine)copper(II)]chloride (0.21 g, 0.47 mmol) in dichloromethane (22 mL) was stirred under air for 36 hours under air. It was filtered over a short silica gel pad, concentrated and purified by column chromatography (hexanes: ethyl acetate; 90:10) to yield 1.45 g (85%) of the product as a white solid.

$^1$H NMR (CDCl$_3$) (δ, ppm): 7.64 (t, J=1.8 Hz, 1H), 7.61-7.60 (m, 1H), 7.51 (s, 1H), 7.40-7.38 (m, 1H), 7.33 (t, J=8.0 Hz, 1H), 4.44 (q, J=7.1 Hz, 2H), 4.27 (q, J=7.1 Hz, 2H), 1.41 (t, J=7.1 Hz, 3H), 1.27 (t, J=7.1 Hz, 3H). MS (ESI): m/e 367.2 (M+1)$^+$ Step 2: 1-(3-bromophenyl)-1H-pyrazole-3,5-dicarboxamide To a solution of diethyl-1-(3-bromophenyl)-1H-pyrazole-3,5-dicarboxylate (0.71 g, 1.96 mmol) in ethanol (5.9 mL), ammonia gas was bubbled through it at 0° C. for 5 minutes. The solution was then stirred at room temperature for 16 hours. The reaction was concentrated and purified by reverse phase HPLC (acetonitrile/water system) (gradient: 25% to 90% acetonitrile over 15 minutes) to give the titled diamide (140 mg, 23%, yield, retention time 4.05 minutes) as a white solid.

$^1$H NMR (CD3OD) ($\delta$, ppm): 7.57 (t, J=1.8 Hz, 1H), 7.65-7.63 (m, 1H), 7.52-7.50 (m, 1H), 7.42 (t, J=8.1 Hz, 1H), 7.31 (s, 1H). MS (ESI): m/e 309 (M+1)$^+$ The following two additional products were also obtained from this reaction: Ethyl-5-aminocarbonyl)-1-(3-bromophenyl)-1H-pyrazole-3-carboxylate (160 mg, 24%, yield, retention time 6.71 minutes).

$^1$H NMR (CDCl$_3$) ($\delta$, ppm): 7.73-7.72 (m, 1H), 7:62-7.60 (m, 1H), 7.47-7.45 (m, 1H), 7.35 (t, J=8.0 Hz, 1H), 7.31 (s, 1H), 5.95 (br s, 1H), 5.78 (br s, 1H), 4.48 (q, J=7.1 Hz, 2H), 1.27 (t, J=7.1 Hz, 3H). MS (ESI): m/e 338.1 (M+1)$^+$ and ethyl-3-aminocarbonyl)-1-(3-bromophenyl)-1H-pyrazole-5-carboxylate (130 mg, 19%, yield, retention time 7.35 minutes).

$^1$H NMR (CDCl$_3$) ($\delta$, ppm): 7.63-7.62 (m, 2H), 7.54 (s, 1H), 7.40-7.34 (m, 2H), 6.78 (br s, 1H), 5.53 (br s, 1H), 4.27 (q, J=7.1 Hz, 2H), 1.28 (t, J=7.1 Hz, 3H). MS (ESI): m/e 338.1 (M+1)$^+$ Step 3: 1-[2'-(trifluoromethyl)biphenyl-3yl-1]-1H-pyrazole-3,5-dicarboxamide To a solution of 1-(3-bromophenyl)-1H-pyrazole-3,5-dicarboxamide (90 mg, 0.28 mmol) and 2-trifluromethoxyphenyl boronic acid (116 mg, 0.56 mmol) in ethanol/toluene (0.23 mL: 0.70 mL) mixture were added tetrakis(triphenylphosphine)palladium (6.5 mg, 0.005 mmol) and 2N sodium carbonate (0.28 mL, 0.56 mmol). The reaction mixture was heated at 90° C. for 16 hours, cooled and partitioned between ethyl acetate and water. The organic phase was washed with saturated sodium bicarbonate and brine, dried over sodium sulfate and concentrated. The crude product was purified by silica-gel column chromatography (0.5:4.5 hexanes/ethyl acetate) to give the product (65 mg, 59%) as a white solid.

$^1$H NMR (CD$_3$OD) ($\delta$, ppm): 7.61 (s, 1H), 7.59-7.55 (m, 4H), 7.51-7.42 (m, 3H), 7.29 (s, 1H). MS (ESI): m/e 391.4 (M+1)$^+$

EXAMPLE 180

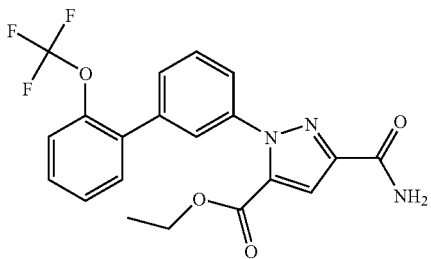

Ethyl-3-(aminocarbonyl)-1-[2'-(trifluoromethoxy)biphenyl-3yl]-1H-pyrazole-5-carboxylate To a solution of ethyl-3-aminocarbonyl)-1-(3-bromophenyl)-1H-pyrazole-5-carboxylate (62 mg, 0.18 mmol) in etha nol (0.61 mL), 2-trifluoromethoxyphenylboronic acid (75 mg, 0.36 mmol) was added followed by PdCl$_2$(dppf)$_2$ (2.4 mg, 0.003 mmol). The solution was heated in a Smith Creators microwave reactor (commercially available from Personal Chemistry, Inc.) at 150° C. for 1000 seconds. After cooling to room temperature, the reaction mixture was partitioned between EtOAc and water. The organic layer was washed with saturated sodium bicarbonate and brine, then dried over sodium sulfate, filtered and concentrated. Purification of the crude product by reverse phase HPLC (acetonitrile/water system) (gradient: 25% to 90% acetonitrile over 15 minutes) yielded 55 mg of the product (72% yield, retention time 8.9 minutes) of the product as a white solid.

$^1$H NMR (CDCl$_3$) ($\delta$, ppm): 7.65-7.63 (m, 1H), 7.60-7.57 (m, 3H), 7.52-7.39 (m, 5H), 6.84 (br s, 1H), 5.51 (br s, 1H), 4.28 (q, J=7.1 Hz, 2H), 1.27 (t, J=7.1 Hz, 3H). MS (ESI): m/e 420.1 (M+1)$^+$

EXAMPLE 181

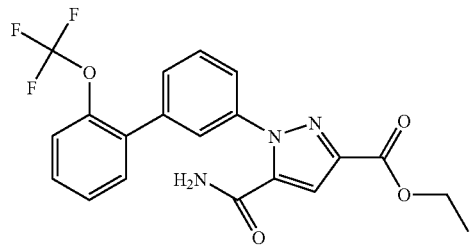

Ethyl-5-(aminocarbonyl)-1-[2'-(trifluoromethoxy)biphenyl-3yl]-1H-pyrazole-3-carboxylate To a solution of ethyl-5-aminocarbonyl)-1-(3-bromophenyl)-1H-pyrazole-3-carboxylate (62 mg, 0.18 mmol) in ethanol (0.61 mL), 2-trifluoromethoxyphenylboronic acid (75 mg, 0.36 mmol) was added followed by PdCl$_2$(dppf)$_2$ (2.4 mg, 0.003 mol). The solution was heated in a Smith Creator™ microwave reactor (commercially available from Personal Chemistry, Inc.) at 150° C. for 1000 seconds. After cooling to room temperature, the reaction mixture was partitioned between EtOAc and water. The organic layer was washed with saturated sodium bicarbonate and brine, then dried over sodium sulfate, filtered and concentrated. Purification of the crude product by reverse phase HPLC (acetonitrile/water system) (gradient: 25% to 90% acetonitrile over 15 minutes) yielded 45 mg of the product (59% yield, retention time 8.6 minutes) of the product as a white solid.

$^1$H NMR (CDCl$_3$) ($\delta$, ppm): 7.61-7.51 (m, 4H), 7.46-7.39 (m, 5H), 6.14 (br s, 1H), 5.88 (br s, 1H), 4.44 (q, J=7.1 Hz, 2H), 1.41 (t, J=7.1 Hz, 3H). MS (ESI): m/e 420.1 (M+1)$^+$ The following additional EXAMPLES (summarized in TABLE 10) were prepared using the methods described in EXAMPLES 179-181.

TABLE 10

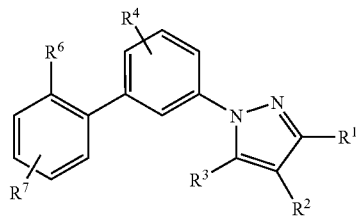

| EXAMPLE # | R7 | R6 | R4 | R3 | R2 | R1 | MS: m/e (M + 1) |
|---|---|---|---|---|---|---|---|
| 182 | H | CF$_3$ | H | CONH$_2$ | H | CONH$_2$ | 375 |
| 183 | H | OCF$_3$ | H | CONH$_2$ | H | CONH$_2$ | 391 |
| 184 | 4-CF$_3$ | CF$_3$ | H | CONH$_2$ | H | CONH$_2$ | 443 |
| 185 | 5-F | CF$_3$ | H | CONH$_2$ | H | CONH$_2$ | 393 |
| 186 | 5-CF$_3$ | OCF$_3$ | H | CONH$_2$ | H | CONH$_2$ | 459 |
| 187 | H | OCHF$_2$ | H | CONH$_2$ | H | CONH$_2$ | 373 |
| 188 | 5-CF$_3$ | CF$_3$ | H | CONH$_2$ | H | CONH$_2$ | 443 |
| 189 | 6-F | CF$_3$ | H | CONH$_2$ | H | CONH$_2$ | 393 |
| 190 | 4-F | OCH$_2$CF$_3$CF$_3$ | H | CONH$_2$ | H | CONH$_2$ | 473 |
| 191 | 6-CF$_3$ | CF$_3$ | H | CONH$_2$ | H | CONH$_2$ | 443 |
| 192 | H | OCH(CH$_3$)$_2$ | H | CONH$_2$ | H | CONH$_2$ | 365 |
| 193 | 3-OCF$_3$ | OCH$_2$CF$_3$CF$_3$ | H | CONH$_2$ | H | CONH$_2$ | 539 |
| 194 | 3-CF$_3$ | OCH$_2$CF$_3$CF$_3$ | H | CONH$_2$ | H | CONH$_2$ | 523 |
| 195 | 5-F | OCH$_2$CF$_3$CF$_3$ | H | CONH$_2$ | H | CONH$_2$ | 473 |
| 196 | 5-F | OCF$_3$ | H | CONH$_2$ | H | CONH$_2$ | 409 |
| 197 | 4-F | CF$_3$ | H | CONH$_2$ | H | CONH$_2$ | 393 |
| 198 | H | CF$_3$ | H | CONH-Et | H | CONH-Et | 431 |
| 199 | H | CF$_3$ | H | CONH$_2$ | H | CONH-Et | 403 |
| 200 | H | OCF$_3$ | 4-F | CONH$_2$ | H | CONH$_2$ | 409 |
| 201 | H | OCF$_3$ | H | CONH-Et | H | CONH$_2$ | 419 |
| 202 | H | OCF$_3$ | H | COOEt | H | COOEt | 449 |
| 203 | H | CF$_3$ | H | COOEt | H | COOEt | 433 |
| 204 | H | OCF$_3$ | H | COOEt | H | CONH$_2$ | 420 |
| 205 | H | CF$_3$ | H | COOEt | H | CONH$_2$ | 404 |
| 206 | 4-CF$_3$ | CF$_3$ | H | COOEt | H | CONH$_2$ | 472 |
| 207 | 4-CF$_3$ | CF$_3$ | H | CONH$_2$ | H | COOEt | 472 |
| 208 | H | OCF$_3$ | H | CONH$_2$ | H | COOEt | 420 |
| 209 | H | CF$_3$ | H | CONH$_2$ | H | COOEt | 404 |
| 210 | H | OCF$_3$ | 4-F | COOH | H | COOEt | 439 |
| 211 | H | OCF$_3$ | 4-F | COOH | H | CONH$_2$ | 410 |
| 212 | H | OCF$_3$ | 4-F | CONH$_2$ | H | COOEt | 438 |
| 213 | H | OCF$_3$ | H | COOH | H | CONH$_2$ | 392 |
| 214 | H | OCF$_3$ | H | CH$_3$ | COOMe | COOEt | 449 |
| 215 | H | OCF$_3$ | H | CH$_3$ | COOH | COOH | 407 |
| 216 | 4-CF$_3$ | CF$_3$ | H | CH$_3$ | COOH | COOH | 459 |
| 217 | H | OCF$_3$ | H | CH$_3$ | CONH$_2$ | CONH$_2$ | 405 |
| 218 | 4-CF$_3$ | CF$_3$ | H | CH$_3$ | CONH$_2$ | CONH$_2$ | 457 |
| 219 | H | CF$_3$ | H | CH$_3$ | COOH | COOH | 391 |
| 220 | H | CF$_3$ | H | CH$_3$ | CONH$_2$ | CONH$_2$ | 389 |
| 221 | 5-CF$_3$ | CF$_3$ | H | CH$_3$ | CONH$_2$ | CONH$_2$ | 457 |
| 222 | 5-CF$_3$ | CF$_3$ | H | CH$_3$ | COOH | COOH | 459 |
| 223 | H | CF$_3$ | 4-OCF$_3$ | CH$_3$ | COOMe | COOH | 488 |
| 224 | H | OCF$_3$ | 4-OCF$_3$ | CH$_3$ | CONH$_2$ | CONH$_2$ | 489 |
| 225 | H | CF$_3$ | 4-OCF$_3$ | CH$_3$ | CONH$_2$ | CONH$_2$ | 473 |
| 226 | H | OCF$_3$ | 4-F | CH$_3$ | COOEt | COOEt | 481 |
| 227 | H | CF$_3$ | 4-F | CH$_3$ | COOEt | COOEt | 465 |
| 228 | H | OCF$_3$ | 4-F | CH$_3$ | COOEt | CONH$_2$ | 451 |
| 229 | H | OCF$_3$ | 4-F | CH$_3$ | CONH$_2$ | CONH$_2$ | 423 |
| 230 | H | CF$_3$ | 4-F | CH$_3$ | COOEt | CONH$_2$ | 435 |
| 231 | H | CF$_3$ | 4-F | CH$_3$ | CONH$_2$ | CONH$_2$ | 407 |
| 232 | H | OCF$_3$ | 4-F | CH$_3$ | COOH | COOH | 425 |
| 233 | H | Cl | H | H | CONH-Me | H | 311 |
| 234 | H | Cl | H | H | CONH$_2$ | CF$_3$ | 365 |
| 235 | H | OCF$_3$ | H | H | COOEt | NH$_2$ | 391 |
| 236 | H | CF$_3$ | H | H | COOEt | NH$_2$ | 376 |
| 237 | H | OCF$_3$ | H | H | COOH | H | 349 |
| 238 | H | OCF$_3$ | H | H | COOEt | H | 377 |
| 239 | 4-CF$_3$ | CF$_3$ | H | H | COOEt | NH$_2$ | 444 |
| 240 | H | OCF$_3$ | H | H | COOH | NH$_2$ | 364 |
| 241 | H | OCF$_3$ | H | H | CONH$_2$ | H | 347 |
| 242 | H | OCF$_3$ | H | H | CONH$_2$ | NH$_2$ | 363 |
| 243 | H | OCF$_3$ | H | CH$_3$ | CONH$_2$ | CH$_3$ | 376 |
| 244 | H | Cl | H | H | CONH$_2$ | H | 297 |

EXAMPLE 245

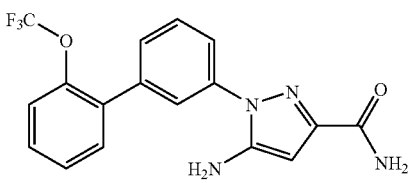

Step 1:

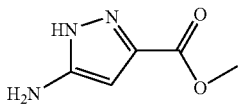

To a cold (0° C.) solution of 5-nitro-3-pyrazole carboxylic acid (500 mg, 3.2 mmol) in anhydrous methanol (5 mL) was added thionyl chloride (417 mL, 3.5 mmol) dropwise. The reaction was stirred at 0° C. for 30 minutes, and refluxed for 1 hour. The reaction solution was concentrated in vacuo to give the methyl ester hydrochloride as a white solid, 570 mg, MS (ESI): m/e 172.03 (M+1)$^+$. The above methyl ester was dissolved in methanol under nitrogen, after aging for 20 minute, 10% Pd on carbon was added carefully, and the mixture was stirred under hydrogen atmosphere for 6 hours. The Pd catalyst was filtered off through a Celite pad. The resulting solution was concentrated to give an off-white solid, 419.5 mg, 93% yield over two steps.

$^1$H NMR (CDCl$_3$) (δ, ppm): 6.02 (s, 1H), 6.20-5.70 (bs, 2H), 3.87 (s, 3H), 3.47 (s, 1H). MS (ESI): m/e 109.95 (M-OMe)$^+$ Step 2:

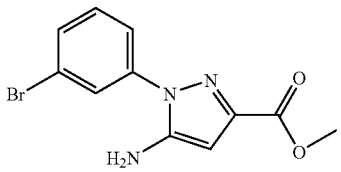

To the solution of the 5-amino-3-pyrazole methyl ester (400 mg, 2.84 mmol) (from Step 1) in dry dichloromethane (3 mL) were added 3-bromophenyl boronic acid (800 mg, 4.0 mmol) and Di-Micron-hydroxo-bis[(N,N,N',N'-tetramethylenediamine) copper(II)] chloride (264 mg, 0.57 mmol). The reaction mixture was refluxed under air for 24 h. and then filtered through a Celite pad. The filter cake was washed with dichloromethane (3×) and the combined organic layer was concentrated in vacuo. The crude product (a mixture of regioisomer) was purified via a column chromatography on silica gel to give titled product as a yellow solid (140 mg, 17% yield).

$^1$H NMR (CDCl$_3$) (δ, ppm): 7.62 (s, 1H), 7.54 (d, 1H, J=8 Hz), 7.42 (bs, 1H), 7.36 (d, 1H, J=7 Hz), 7.31 (m, 2H), 6.44 (bs, 1H), 3.84 (s, 3H). MS (ESI): m/e 298.06 (M+1)$^+$ Step 3:

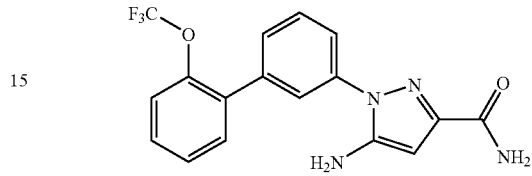

The 3-bromophenyl pyrazole methyl ester (300 mg, 1 mmol) (from Step 2) was mixed with ammonia-methanol (7.0 N, 4 mL) in a sealed tube and heated overnight at 70° C. After cooling, the reaction mixture was concentrated to give the corresponding amide product as yellow foam 220 mg (73%). To a solution of 2-trifluoromethoxyphenyl boronic acid (134 mg, 0.65 mmol) and the above 3-bromophenyl pyrozole amide (130 mg, 0.46 mmol) in toluene (4 mL) and methanol (1 mL) was added tetrakis(triphenyl phosphine) palladium (106 mg, 0.13 mmol), and aqueous sodium carbonate (2.0 M, 0.5 mL, 1.3 mmol). The reaction mixture was stirred at 90° C. for 14 hours. After cooling to room temperature, the mixture was filtered through a Celite pad, and washed with ethyl acetate (3×). The combined filtrate was concentrated in vacuo, and the resulting residue was dissolved in ethyl acetate. The organic phase was washed with saturated sodium carbonate aqueous solution and brine, and then dried over anhydrous sodium sulfate. After concentration, the crude product was purified by column chromatography on silica gel to afford the titled compound as a yellow solid (125 mg, 75% yield).

$^1$H NMR (CDCl$_3$) (δ, ppm): 7.80-7.70 (m, 3H), 7.59-7.44 (m, 6H), 6.79 (bs, 1H), 5.40 (bs, 1H). MS (ESI): m/e 363.16 (M+1)$^+$ The following additional EXAMPLES (summarized in TABLE 11 and 12) were prepared using the methods described in EXAMPLE 141.

TABLE 11

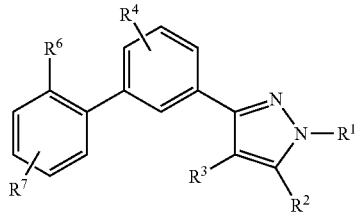

| EXAMPLE # | R$^7$ | R$^6$ | R$^4$ | R$^3$ | R$^2$ | R$^1$ | MS: m/e (M + 1) |
|---|---|---|---|---|---|---|---|
| 246 | H | OCF$_3$ | H | H | COOCH$_3$ | H | 377 |
| 247 | H | CF$_3$ | H | NH$_2$ | CONH$_2$ | H | 363 |
| 248 | H | OCF$_3$ | H | NH$_2$ | COOH | H | 380 |
| 249 | H | OCF$_3$ | H | NH$_2$ | CONH$_2$ | H | 379 |
| 250 | H | CF$_3$ | H | NH$_2$ | COOH | H | 364 |
| 251 | H | OCF$_3$ | H | H | COOEt | H | 391 |
| 252 | H | CF$_3$ | H | H | COOEt | H | 375 |

TABLE 11-continued

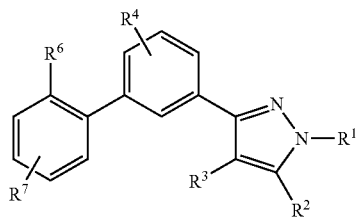

| EXAMPLE # | R7 | R6 | R4 | R3 | R2 | R1 | MS: m/e (M + 1) |
|---|---|---|---|---|---|---|---|
| 253 | H | CF3 | H | H | CONH2 | 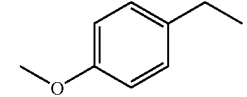 | 452 |
| 254 | H | OCF3 | F | H | COOEt | H | 408 |
| 255 | H | OCF3 | F | H | CONH2 | H | 407 |
| 256 | H | OCF3 | H | CH3 | COOEt | H | 375 |
| 257 | H | OCF3 | H | CH3 | COOH | H | 347 |
| 258 | H | OCF3 | H | CH3 | CONH2 | H | 346 |
| 259 | H | CF3 | H | CH3 | COOH | H | 331 |
| 260 | H | CF3 | H | CH3 | CONH2 | H | 330 |
| 261 | 4-CF3 | CF3 | H | CH3 | COOH | H | 415 |
| 262 | 4-CF3 | CF3 | H | CH3 | CONH2 | H | 414 |
| 263 | H | OCF3 | F | H | COOH | H | 380 |
| 264 | 5-CF3 | CF3 | H | H | COOH | H | 401 |
| 265 | 5-CF3 | CF3 | H | H | CONH2 | H | 400 |
| 266 | H | CF3 | H | CH3 | CONH2 | t-Bu | 402 |
| 267 | H | OCF3 | H | H | COOH | t-Bu | 405 |
| 268 | H | OCF3 | H | H | CONH2 | t-Bu | 404 |
| 269 | 6-F | CF3 | H | H | CONH2 | H | 350 |
| 270 | 6-F | CF3 | H | H | COOH | H | 351 |
| 271 | 5-F | OCF3 | H | H | COOH | H | 367 |
| 272 | 5-F | OCF3 | H | H | CONH2 | H | 366 |
| 273 | 4-CF3 | CF3 | H | H | CONH2 | H | 400 |
| 274 | H | OCF3 | H | H | CONHNMe2 | H | 391 |

TABLE 12

EXAMPLE 275

MS: m/e 424

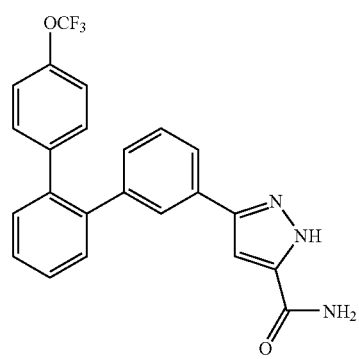

TABLE 12-continued

EXAMPLE 276
MS: m/e 408

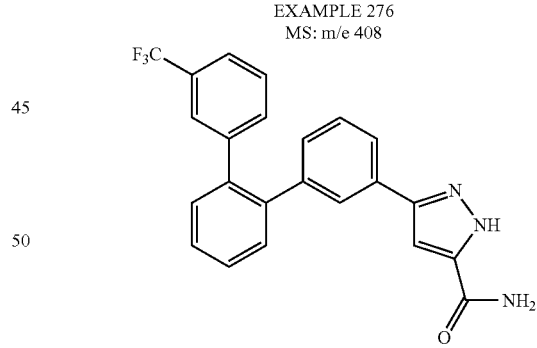

EXAMPLE 277
MS: m/e 442

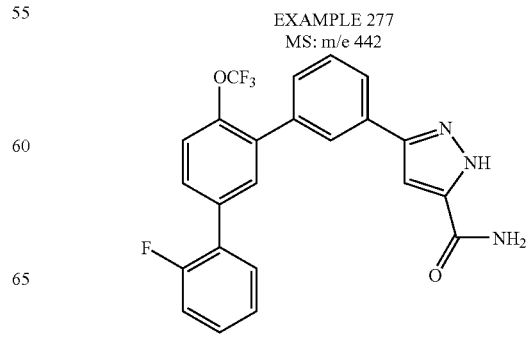

TABLE 12-continued
EXAMPLE 278
MS: m/e 443
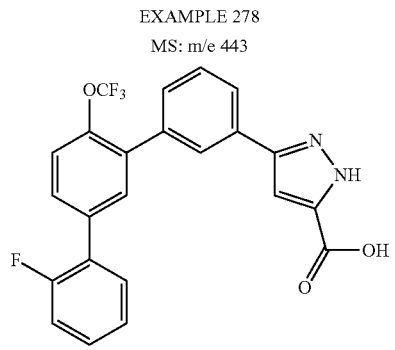
EXAMPLE 279
MS: m/e 412
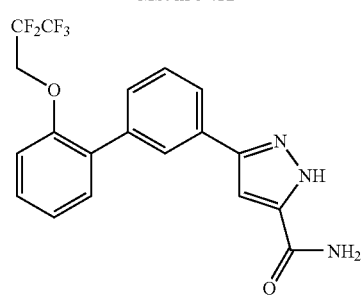
EXAMPLE 280
MS: m/e 388
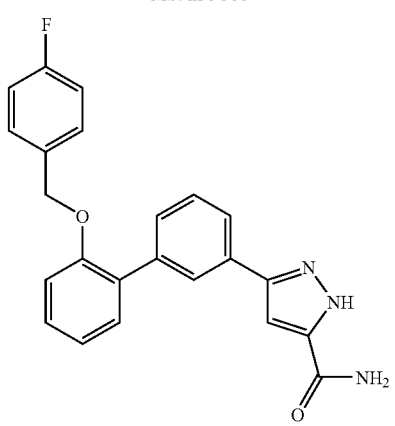
EXAMPLE 281
MS: m/e 358
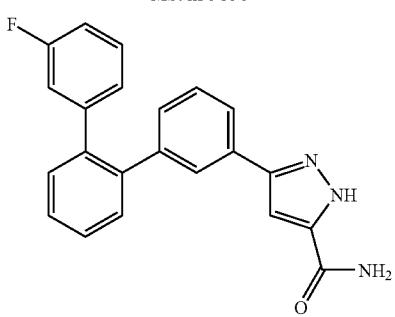
TABLE 12-continued
EXAMPLE 282
MS: m/e 375
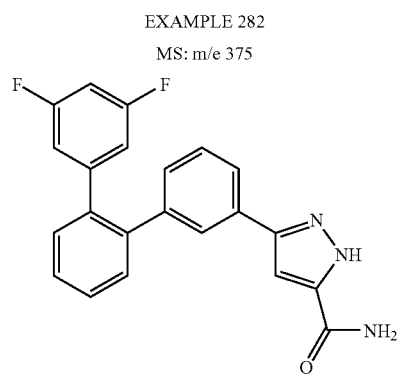
EXAMPLE 283
MS: m/e 375
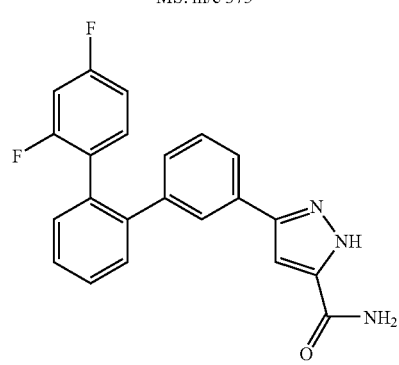
EXAMPLE 284
MS: m/e 413
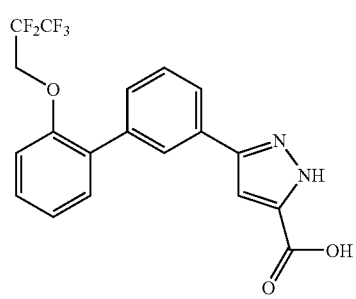
EXAMPLE 285
MS: m/e 340
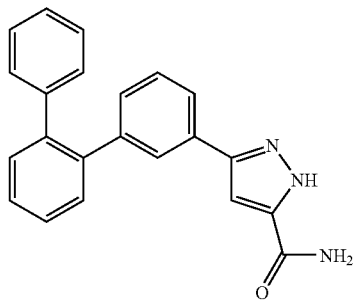

TABLE 12-continued

EXAMPLE 286
MS: m/e 320

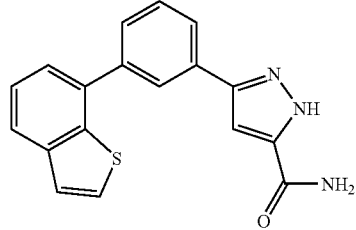

EXAMPLE 287
MS: m/e 431

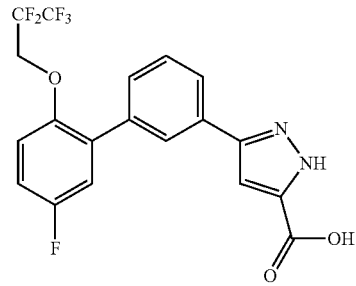

EXAMPLE 288
MS: m/e 430

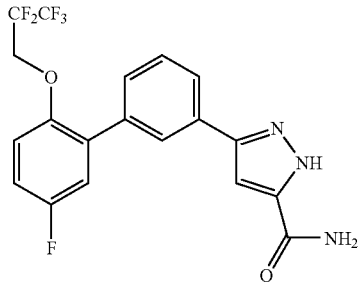

EXAMPLE 289
MS: m/e 469

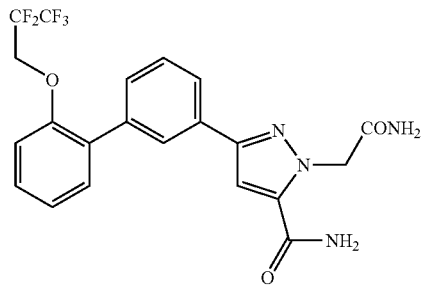

EXAMPLE 290
MS: m/e 265

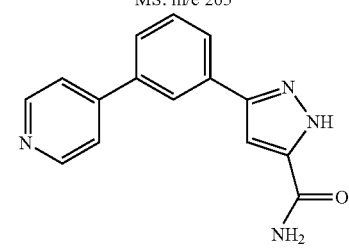

TABLE 12-continued

EXAMPLE 291
MS: m/e 304

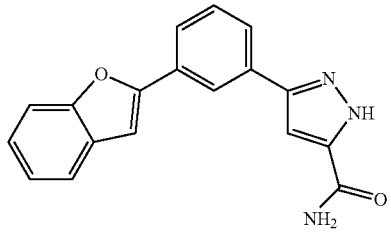

EXAMPLE 292
MS: 469

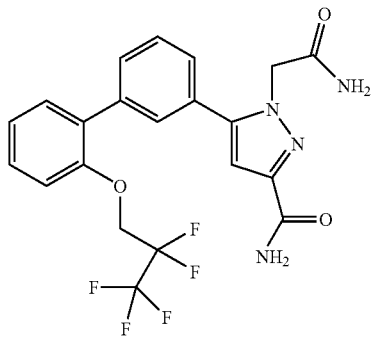

Other variations or modifications, which will be obvious to those skilled in the art, are within the scope and teachings of this invention. This invention is not to be limited except as set forth in the following claims.

What is claimed is:

1. A compound represented by Formula (I), (II), (III) or (IV):

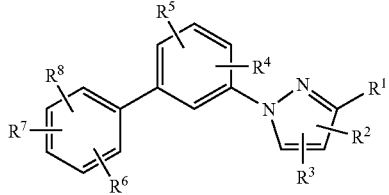
(I)

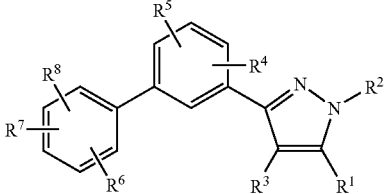
(II)

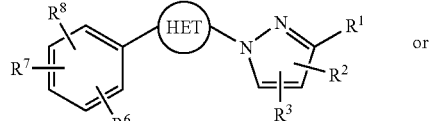
(III)

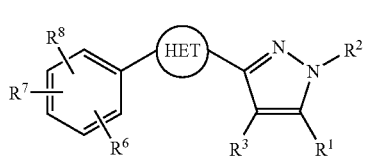
(IV)

or a pharmaceutically acceptable salt thereof, wherein

HET is one of the following heterocycles:

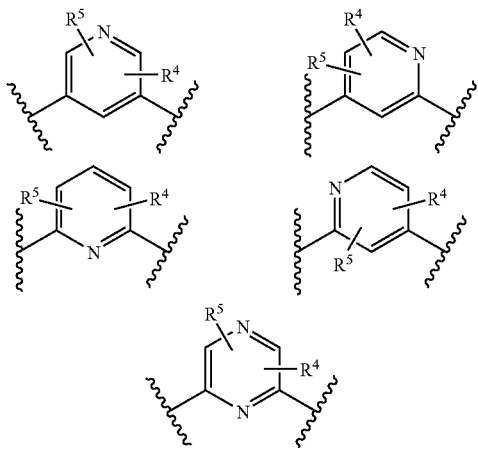

R¹ is (a) H;

(b) $C_1$-$C_6$-alkyl, $C_2$-$C_4$-alkenyl, $C_2$-$C_4$-alkynyl, $C_3$-$C_6$-cycloalkyl, or $C_1$-$C_4$-alkyl-[$C_3$-$C_6$-cycloalkyl], any of which is optionally substituted with one or more of the following substituents: F, $CF_3$, OH, O—($C_1$-$C_4$)alkyl, $S(O)_{0-2}$—($C_1$-$C_4$)alkyl, O—$CONR^aR^b$, $NR^aR^b$, $N(R^a)CONR^aR^b$, COO—($C_1$-$C_4$)alkyl, COOH, CN, CON$R^aR^b$, $SO_2NR^aR^b$, $N(R^a)SO_2NR^aR^b$, —C(=NH)$NH_2$, tetrazolyl, triazolyl, imidazolyl, oxazolyl, oxadiazolyl, isooxazolyl, thiazolyl, furyl, thienyl, pyrazolyl, pyrrolyl, pyridyl, pyrimidinyl, pyrazinyl, phenyl, piperidinyl, morpholinyl, pyrrolidinyl or piperazinyl;

(c) —O—$C_1$-$C_6$-alkyl, —O—$C_3$-$C_6$-cycloalkyl, —S—$C_1$-$C_6$-alkyl or —S—$C_3$-$C_6$-cycloalkyl, any of which is optionally substituted with one or more of the following substituents: F, $CF_3$, OH, O—($C_1$-$C_4$)alkyl, $S(O)_{0-2}$—($C_1$-$C_4$)alkyl, O—$CONR^aR^b$, $NR^aR^b$, $N(R^a)CONR^aR^b$, COO—($C_1$-$C_4$)alkyl, COOH, CN, CON$R^aR^b$, $SO_2NR^aR^b$, $N(R^a)SO_2NR^aR^b$, —C(=NH)$NH_2$, tetrazolyl, triazolyl, imidazolyl, oxazolyl, oxadiazolyl, isooxazolyl, thiazolyl, furyl, thienyl, pyrazolyl, pyrrolyl, pyridyl, pyrimidinyl, pyrazinyl, phenyl, piperidinyl, morpholinyl, pyrrolidinyl or piperazinyl;

(d) —$C_0$-$C_4$-alkyl-$C_1$-$C_4$-perfluoroalkyl, or —O—$C_0$-$C_4$-alkyl-$C_1$-$C_4$-perfluoroalkyl;

(e) —OH;

(f) —O-aryl, or —O—$C_1$-$C_4$-alkyl-aryl, wherein aryl is phenyl, pyridyl, pyrimidinyl, furyl, thienyl, pyrrolyl, triazolyl, pyrazolyl, thiazolyl, isoxazolyl, oxazolyl, or oxadiazolyl, any aryl of which is optionally substituted with 1-3 substituents selected from i) F, Cl, Br, I, ii) —CN, iii) —$NO_2$, iv) —C(=O)($R^a$), v) —$OR^a$, vi) —$NR^aR^b$, vii) —$C_{0-4}$alkyl-CO—$OR^a$, viii) —$C_{0-4}$alkyl)-NH—CO—$OR^a$, ix) —($C_{0-4}$alkyl)-CO—N($R^a$)($R^b$), x) —$S(O)_{0-2}R^a$, xi) —$SO_2N(R^a)(R^b)$, xii) —$NR^aSO_2R^a$, xiii) —$C_{1-10}$alkyl, and xiv) —$C_{1-10}$alkyl, wherein one or more of the alkyl carbons can be replaced by a —$NR^a$—, —O—, —$S(O)_{1-2}$—, —O—C(O)—, —C(O)—O—, —C(O)—N($R^a$)—, —N($R^a$)—C(O)—, —N($R^a$)—C(O)—N($R^a$)—, —C(O)—, —CH(OH)—, —C=C—, or —C≡C—;

(g) —OCON($R^a$)($R^b$), or —$OSO_2N(R^a)(R^b)$;

(h) —SH, or —SCON($R^a$)($R^b$);

(i) $NO_2$;

(j) $NR^aR^b$, —N(COR$^a$)R$^b$, —N($SO_2R^a$)R$^b$, —N($R^a$)$SO_2N(R^a)_2$, —N($OR^a$)CON$R^aR^b$, —N($R^a$)$SO_2R^a$ or —N($R^a$)CON($R^a$)$_2$;

(k) —CH(OR$^a$)R$^a$, —C(OR$^b$)$CF_3$, —CH(NHR$^b$)R$^a$, —C(=O)R$^a$, C(=O)$CF_3$, —$SOCH_3$, —$SO_2CH_3$, COOR$^a$, CN, CONR$^aR^b$, —COCONR$^aR^b$, —$SO_2NR^aR^b$, —$CH_2O$—$SO_2NR^aR^b$, $SO_2N(R^a)OR^a$, —C(=NH)$NH_2$, —CR$^a$=N—OR$^a$, CH=CHCONR$^aR^b$;

(l) —CONR$^a$(CH$_2$)$_{0-2}$C(R$^a$)(R$^b$)(CH$_2$)$_{0-2}$CONR$^aR^b$;

(m) tetrazolyl, tetrazolinonyl, triazolyl, triazolinonyl, imidazolyl, imidozolonyl, oxazolyl, oxadiazolyl, isooxazolyl, thiazolyl, furyl, thienyl, pyrazolyl, pyrazolonyl, pyrrolyl, pyridyl, pyrimidinyl, pyrazinyl, or phenyl, any of which is optionally substituted with 1-3 substituents selected from i) F, Cl, Br, I, ii) —CN, iii) —$NO_2$, iv) —C(=O)R$^a$, v) $C_1$-$C_6$-alkyl, vi) —O—R$^a$, vii) —NR$^aR^b$, viii) —$C_0$-$C_4$-alkyl-CO—OR$^a$, ix) —($C_0$-$C_4$-alkyl) -NH—CO—OR$^a$, x) —($C_0$-$C_4$-alkyl)-CO—NR$^aR^b$, xi) —$S(O)_{0-2}R^a$, xii) —$SO_2NR^aR^b$, xiii) —$NHSO_2R^a$, xiv) —$C_1$-$C_4$-perfluoroalkyl, and xv) —O—$C_1$-$C_4$-perfluoroalkyl;

(n) —C(R$^a$)=C(R$^b$)—COOR$^a$, or —C(R$^a$)=C(R$^b$)—CONR$^aR^b$;

(o)

(p) piperidin-1-yl, morpholin-1-yl, pyrrolidin-1-yl, piperazin-1-yl or 4-susbstituted piperazin-1-yl, any of which is optionally substituted with 1-3 substituents selected from i) —CN, ii) —C(=O)(R$^a$), iii) $C_1$-$C_6$-alkyl, iv) —OR$^a$, v) —NR$^aR^b$, vi) —$C_0$-$C_4$-alkyl -CO—OR$^a$, vii) —($C_0$-$C_4$-alkyl)-NH—CO—OR$^a$, viii) —($C_0$-$C_4$-alkyl)-CON(R$^a$)(R$^b$), ix) —SR$^a$, x) —$S(O)_{0-2}R^a$, xi) —$SO_2N(R^a)(R^b)$, xii) —NR$^a$SO$_2$R$^a$ xiii) —$C_1$-$C_4$-perfluoroalkyl and xiv) —O—$C_1$-$C_4$-perfluoroalkyl;

R$^a$ is (a) H;

(b) $C_1$-$C_4$-alkyl, optionally substituted with one or more of the following substituents: F, $CF_3$, OH, O—($C_1$-$C_4$)alkyl, $S(O)_{0-2}$—($C_1$-$C_4$)alkyl, —OCONH$_2$, —OCONH($C_1$-$C_4$alkyl), —OCON($C_1$-$C_4$alkyl)($C_1$-$C_4$alkyl), —OCONHC$_1$-$C_4$alkyl-aryl), —OCON($C_1$-$C_4$alkyl)($C_1$-$C_4$alkyl-aryl), NH$_2$, NH($C_1$-$C_4$alkyl), N($C_1$-$C_4$alkyl)($C_1$-$C_4$alkyl), NH($C_1$-$C_4$alkyl-aryl), N($C_1$-$C_4$alkyl)($C_1$-$C_4$alkyl-aryl), NHCONH$_2$, NHCONH($C_1$-$C_4$alkyl), NHCONH($C_1$-$C_4$alkyl-aryl), —NHCON($C_1$-$C_4$alkyl)($C_1$-$C_4$alkyl), NHCON ($C_1$-$C_4$alkyl)($C_1$-$C_4$alkyl-aryl), N($C_1$-$C_4$alkyl)CON($C_1$-$C_4$alkyl)($C_1$-$C_4$alkyl), N($C_1$-$C_4$alkyl)CON($C_1$-$C_4$alkyl)($C_1$-$C_4$alkyl-aryl), COO—($C_1$-$C_4$-alkyl), COOH, CN, CONH$_2$, CONH($C_1$-$C_4$alkyl), CON($C_1$-$C_4$alkyl)($C_1$-$C_4$alkyl), SO$_2$NH$_2$, SO$_2$NH ($C_1$-$C_4$alkyl), SO$_2$NH($C_1$-$C_4$alkyl-aryl), SO$_2$N($C_1$-$C_4$alkyl)($C_1$-$C_4$alkyl), NHSO$_2$NH$_2$, —C(=NH)NH$_2$, tetrazolyl, triazolyl, imidazolyl, oxazolyl, oxadiazolyl, isooxazolyl, thiazolyl, furyl, thienyl, pyrazolyl, pyrrolyl, pyridyl, pyrimidinyl, pyrazinyl, phenyl, piperidinyl, morpholinyl, pyrrolidinyl or piperazinyl;

(c) $C_0$-$C_4$-alkyl-($C_1$-$C_4$)-perfluoroalkyl; or (d) —$C_1$-$C_4$-alkyl-aryl, wherein aryl is phenyl, pyridyl, pyrimidinyl, furyl, thienyl, pyrrolyl, triazolyl, pyrazolyl, thiazolyl, isoxazolyl, oxazolyl, or oxadiazolyl, any aryl of which is optionally substituted with 1-3 substituents selected from i) F, Cl, Br, I, ii) —CN, iii) —$NO_2$, iv) —C(=O)($C_1$-$C_4$-alkyl), v) —O($C_1$-$C_4$-alkyl), vi) —N($C_1$-$C_4$-alkyl)($C_1$-$C_4$-alkyl), vii) —$C_{1-10}$alkyl, and viii) —$C_{1-10}$alkyl, wherein one or more of the alkyl carbons can be replaced by a —O—, —$S(O)_{1-2}$—, —O—C(O)—, —C(O)—O—, —C(O)—CH(OH)—, —C=C—, or —C≡C—;

$R^b$ is
(a) H; or
(b) $C_1$-$C_6$-alkyl, optionally substituted with one or more of the following substituents: F, $CF_3$, OH, O—($C_1$-$C_4$) alkyl, $S(O)_{0-2}$—($C_1$-$C_4$)alkyl, —$OCONH_2$, —OCONH ($C_1$-$C_4$alkyl), $NH_2$, NH($C_1$-$C_4$alkyl), N($C_1$-$C_4$alkyl) ($C_1$-$C_4$alkyl), $NHCONH_2$, NHCONH ($C_1$-$C_4$alkyl), —NHCON($C_1$-$C_4$alkyl)($C_1$-$C_4$alkyl), COO—($C_1$-$C_4$-alkyl), COOH, CN, or $CONH_2$;

$R^2$ is:
(a) H;
(b) —$C_1$-$C_4$-alkyl, —$C_3$-$C_6$-cycloalkyl or —$C_1$-$C_4$-alkyl-($C_3$-$C_6$)-cycloalkyl, optionally substituted with one or more of the following substituents: F, $CF_3$, OH, O—($C_1$-$C_4$)alkyl, $S(O)_{0-2}$—($C_1$-$C_4$)alkyl, O—$CONR^aR^b$, $NR^aR^b$, $N(R^a)CONR^aR^b$, COO—($C_1$-$C_4$)alkyl, COOH, CN, $CONR^aR^b$, $SO_2NR^aR^b$, $N(R^a)SO_2NR^aR^b$, —C(=NH)$NH_2$, tetrazolyl, triazolyl, imidazolyl, oxazolyl, oxadiazolyl, isooxazolyl, thiazolyl, furyl, thienyl, pyrazolyl, pyrrolyl, pyridyl, pyrimidinyl, pyrazinyl, phenyl, piperidinyl, morpholinyl, pyrrolidinyl or piperazinyl;
(c) —$C_0$-$C_4$-alkyl-$C_1$-$C_4$-perfluoroalkyl;
(d) aryl or —($C_1$-$C_4$-alkyl)-aryl, wherein aryl is phenyl, pyridyl, pyrimidinyl, furyl, thienyl, pyrrolyl, triazolyl, pyrazolyl, thiazolyl, isoxazolyl, oxazolyl, or oxadiazolyl, any aryl of which is optionally substituted with 1-3 substituents selected from i) F, Cl, Br, I, ii) —CN, iii) —$NO_2$, iv) —C(=O)($R^a$), v) —$OR^a$, vi) —$NR^aR^b$, vii) —$C_{0-4}$alkyl-CO—$OR^a$, viii) —($C_{0-4}$alkyl)-NH—CO—$OR^a$, ix) —($C_{0-4}$alkyl)-CO—N($R^a$)($R^b$), x) —$S(O)_{0-2}R^a$, xi) —$SO_2N(R^a)(R^b)$, xii) —$NR^aSO_2R^a$, xiii) —$C_{1-10}$alkyl, and xiv) —$C_{1-10}$alkyl, wherein one or more of the alkyl carbons can be replaced by a —$NR^a$—, —O—, —$S(O)_{1-2}$—, —O—C(O)—, —C(O)—O—, —C(O)—N($R^a$)—, —N($R^a$)—C(O)—, —N($R^a$)—C(O)—N($R^a$)—, —C(O)—, —CH(OH)—, —C=C—, or —C≡C—;
(e) —C(=O)($R^a$), —$CONR^aR^b$, COO—$C_1$-$C_4$)alkyl, —$SO_2R^a$, $N(R^a)COR^a$, —$SO_2N(R^a)(R^b)$;

$R^3$ is
(a) H;
(b) —$C_1$-$C_4$-alkyl, —$C_3$-$C_6$-cycloalkyl or —$C_1$-$C_4$-alkyl-($C_3$-$C_6$)-cycloalkyl, optionally substituted with one or more of the following substituents: F, $CF_3$, OH, O—($C_1$-$C_4$)alkyl, $S(O)_{0-2}$-($C_1$-$C_4$)alkyl, O—$CONR^aR^b$, $NR^aR^b$, $N(R^a)CONR^aR^b$, COO—($C_1$-$C_4$)alkyl, COOH, CN, $CONR^aR^b$, $SO_2NR^aR^b$, $N(R^a)SO_2NR^aR^b$, —C(=NH)$NH_2$, tetrazolyl, triazolyl, imidazolyl, oxazolyl, oxadiazolyl, isooxazolyl, thiazolyl, furyl, thienyl, pyrazolyl, pyrrolyl, pyridyl, pyrimidinyl, pyrazinyl, phenyl, piperidinyl, morpholinyl, pyrrolidinyl or piperazinyl;
(c) —$C_0$-$C_4$-alkyl-$C_1$-$C_4$-perfluoroalkyl;
(d) aryl or —($C_1$-$C_4$-alkyl)-aryl, wherein aryl is phenyl, pyridyl, pyrimidinyl, furyl, thienyl, pyrrolyl, triazolyl, pyrazolyl, thiazolyl, isoxazolyl, oxazolyl, or oxadiazolyl, any aryl of which is optionally substituted with 1-3 substituents selected from i) F, Cl, Br, I, ii) —CN, iii) —$NO_2$, iv) —C(=O)($R^a$), v) —$OR^a$, vi) —$NR^aR^b$, vii) —$C_{0-4}$alkyl-CO—$OR^a$, viii) —($C_{0-4}$alkyl)-NH—CO—$OR^a$, ix) —($C_{0-4}$alkyl)-CO—N($R^a$)($R^b$), x) —$S(O)_{0-2}R^a$, xi) —$SO_2N(R^a)(R^b)$, xii) —$NR^aSO_2R^a$, xiii) —$C_{1-10}$alkyl, and xiv) —$C_{1-10}$alkyl, wherein one or more of the alkyl carbons can be replaced by a —$NR^a$—, —O—, —$S(O)_{1-2}$—, —O—C(O)—, —C(O)—O—, —C(O)—N($R^a$)—, —N($R^a$)—C(O)—, —N($R^a$)—C(O)—N($R^a$)—, —C(O)—, —CH(OH)—, —C=C—, or —C≡C—;
(e) —O—$C_1$-$C_4$-alkyl, —O—$C_0$-$C_4$-alkyl-$C_1$-$C_4$-perfluoroalkyl, —O-aryl or —O($C_1$-$C_4$-alkyl)-aryl;
(f) —C(=O)($R^a$), —$SO_2R^a$, —$SO_2N(R^a)(R^b)$, CN, $NR^aR^b$, $NO_2$, F, Cl, Br, I, OH, $OCONR^aR^b$, O($C_1$-$C_4$-alkyl)$CONR^aR^b$, —$OSO_2NR^aR^b$, $COOR^a$, $N(R^a)COR^a$, or $CONR^aR^b$;

$R^4$ and $R^5$ each independently is:
(a) H;
(b) —$C_1$-$C_6$-alkyl, —$C_2$-$C_6$-alkenyl, —$C_2$-$C_6$-alkynyl or —$C_3$-$C_6$-cycloalkyl, any of which is optionally substituted with one or more of the following substituents: F, $CF_3$, —O—($C_1$-$C_4$)alkyl, CN, —$N(R^a)(R^b)$, —$NR^aR^b$, CO—($C_1$-$C_4$)alkyl, $COOR^b$, $CON(R^a)(R^b)$ or phenyl;
(c) —O—$C_0$-$C_6$-alkyl, —O-aryl, or —O—$C_1$-$C_4$-alkyl-aryl, wherein aryl is phenyl, pyridyl, pyrimidinyl, furyl, thienyl, pyrrolyl, triazolyl, pyrazolyl, thiazolyl, isoxazolyl, oxazolyl, or oxadiazolyl, any aryl of which is optionally substituted with 1-3 substituents selected from i) F, Cl, Br, I, ii) —CN, iii) —$NO_2$, iv) —C(=O)($R^a$), v) —$OR^a$, vi) —$NR^aR^b$, vii) —$C_{0-4}$alkyl-CO—$OR^a$, viii) —($C_{0-4}$alkyl)-NH—CO—$OR^a$, ix) —($C_{0-4}$alkyl)-CO—N($R^a$)($R^b$), x) —$S(O)_{0-2}R^a$, xi) —$SO_2N(R^a)(R^b)$, xii) —$NR^aSO_2R^a$, xiii) —$C_{1-10}$alkyl, and xiv) —$C_{1-10}$alkyl, wherein one or more of the alkyl carbons can be replaced by a —$NR^a$—, —O—, —$S(O)_{1-2}$—, —O—C(O)—, —C(O)—O—, —C(O)—N($R^a$)—, —N($R^a$)—C(O)—, —N($R^a$)—C(O)—N($R^a$)—, —C(O)—, —CH(OH)—, —C=C—, or —C≡C—;
(d) —$C_0$-$C_4$-alkyl-$C_1$-$C_4$-perfluoroalkyl, or —O—$C_0$-$C_4$-alkyl-$C_1$-$C_4$-perfluoroalkyl; or
(e) CN, $NH_2$, $NO_2$, F, Cl, Br, I, OH, $OCON(R^a)(R^b)$O($C_1$-$C_4$-alkyl)$CONR^aR^b$, —$OSO_2N(R^a)(R^b)$, $COOR^b$, $CON(R^a)(R^b)$, or aryl, wherein aryl is phenyl, pyridyl, pyrimidinyl, furyl, thienyl, pyrrolyl, triazolyl, pyrazolyl, thiazolyl, isoxazolyl, oxazolyl, or oxadiazolyl, any aryl of which is optionally substituted with 1-3 substituents selected from i) F, Cl, Br, I, ii) —CN, iii) —$NO_2$, iv) —C(=O)($R^a$), v) —$OR^a$, vi) —$NR^aR^b$, vii) —$C_{0-4}$ alkyl-CO—$OR^a$, viii) —($C_{0-4}$alkyl)-NH—CO—$OR^a$, ix) —($C_{0-4}$alkyl)—CO—N($R^a$)($R^b$), x) —$S(O)_{0-2}R^a$, xi) —$SO_2N(R^a)(R^b)$, xii) —$NR^aSO_2R^a$, xiii) —$C_{1-10}$ alkyl, and xiv) —$C_{1-10}$alkyl, wherein one or more of the alkyl carbons can be replaced by a —$NR^a$—, —O—, —$S(O)_{1-2}$—, —O—C(O)—, —C(O)—O—, —C(O)—N($R^a$)—, —N($R^a$)—C(O)—, —N($R^a$)—C(O)—N($R^a$)—, —C(O)—, —CH(OH)—, —C=C—, or —C≡C; and $R^6$, $R^7$ and $R^8$ each independently is:
(a) H;
(b) $C_1$-$C_6$-alkyl, $C_2$-$C_4$-alkenyl, $C_2$-$C_4$-alkynyl or $C_3$-$C_6$-cycloalkyl, any of which is optionally substituted with one or more of the following substituents: F, $CF_3$, OH, O—($C_1$-$C_4$)alkyl, $OCON(R^a)(R^b)$, $NR^aR^b$, $COOR^a$, CN, $CONR^aR^b$, $N(R^a)CONR^aR^b$, $N(R^a)SO_2NR^aR^b$, SO$_2$NR$^a$R$^b$, S(O)$_{0-2}$(C$_1$-C$_4$-alkyl), —C(=NH)NH$_2$, tetrazolyl, triazolyl, imidazolyl, oxazolyl, oxadiazolyl, isooxazolyl, thiazolyl, furyl, thienyl, pyrazolyl, pyrrolyl, pyridyl, pyrimidinyl, pyrazinyl, phenyl, piperidinyl, morpholinyl, pyrrolidinyl, or piperazinyl;

(c)   —O—C$_1$-C$_6$-alkyl,   —O—C$_3$-C$_6$-cycloalkyl, —S—C$_1$-C$_6$-alkyl or —S—C$_3$-C$_6$-cycloalkyl, any of which is optionally substituted with one or more of the following substituents: F, CF$_3$, OH, O—(C$_1$-C$_4$)alkyl, NH$_2$, NH(C$_1$-C$_4$-alkyl), N(C$_1$-C$_4$-alkyl)$_2$, COOH, CN, CONH$_2$, CONH(C$_1$-C$_4$-alkyl), CONH(C$_1$-C$_4$-alkyl)$_2$, SO$_2$NH$_2$, SO$_2$NH(C$_1$-C$_4$-alkyl), tetrazolyl, triazolyl, imidazolyl, oxazolyl, oxadiazolyl, isooxazolyl, thiazolyl, furyl, thienyl, pyrazolyl, pyrrolyl, pyridyl, pyrimidinyl, pyrazinyl, phenyl, piperidinyl, morpholinyl, pyrrolidinyl, or piperazinyl;

(d) —C$_0$-C$_4$-alkyl-C$_1$-C$_4$-perfluoroalkyl, or —O—C$_0$-C$_4$-alkyl-C$_1$-C$_4$-perfluoroalkyl;

(e) —O-aryl, or —O—C$_1$-C$_4$-alkyl-aryl, wherein aryl is phenyl, pyridyl, pyrimidinyl, furyl, thienyl, pyrrolyl, triazolyl, pyrazolyl, thiazolyl, isoxazolyl, oxazolyl, or oxadiazolyl, any aryl of which is optionally substituted with 1-3 substituents selected from i) F, Cl, Br, I, ii) —CN, iii) —NO$_2$, iv) —C(=O)(R$^a$), v) —OR$^a$, vi) —NR$^a$R$^b$, vii) —C$_{0-4}$alkyl-CO—OR$^a$, viii) —C$_{0-4}$alkyl)-NH—CO—OR$^a$, ix) —(C$_{0-4}$alkyl)-CO—N(R$^a$)(R$^b$), x) —S(O)$_{0-2}$R$^a$, xi) —SO$_2$N(R$^a$)(R$^b$), xii) —NR$^a$SO$_2$R$^a$, xiii) —C$_{1-10}$alkyl, and xiv) —C$_{1-10}$alkyl, wherein one or more of the alkyl carbons can be replaced by a —NR$^a$—, —O—, —S(O)$_{1-2}$—, —O—C(O)—, —C(O)—O—, —C(O)—N(R$^a$)—, —N(R$^a$)—C(O)—, —N(R$^a$)—C(O)—N(R$^a$)—, —C(O)—, —CH(OH)—, —C=C—, or —C≡C; (f) CN, N(R$^a$)(R$^b$), NO$_2$, F, Cl, Br, I, —OR$^a$, —SR$^a$, —OCON(R$^a$)(R$^b$), —OSO$_2$N(R$^a$)(R$^b$), COOR$^b$, CON(R$^a$)(R$^b$), —N(R$^a$)CON(R$^a$)(R$^b$), —N(R$^a$)SO$_2$N(R$^a$)(R$^b$), C(OR$^b$)R$^a$, —C(OR$^a$)CF$_3$, C(NHR$^a$)CF$_3$, C(=O)R$^a$, C(=O)CF$_3$, —SOCH$_3$, —SO$_2$CH$_3$, —NHSO$_2$(C$_{1-6}$-alkyl), —NHSO$_2$-aryl, SO$_2$N(R$^a$)(R$^b$), —CH$_2$OSO$_2$N(R$^a$)(R$^b$), SO$_2$N(R$^b$)—OR$^a$, —C(=NH)NH$_2$, —CR$_a$=N—OR$_a$, CH=CH or aryl, wherein aryl is phenyl, pyridyl, pyrimidinyl, furyl, thienyl, pyrrolyl, triazolyl, pyrazolyl, thiazolyl, isoxazolyl, oxazolyl, or oxadiazolyl, any aryl of which is optionally substituted with 1-3 substituents selected from i) F, Cl, Br, I, ii) —CN, iii) —NO$_2$, iv) —C(=O)(R$^a$), v) —OR$^a$, vi) —NR$^a$R$^b$, vii) —C$_{0-4}$alkyl-CO—OR$^a$, viii) —(C$_{0-4}$alkyl)-NH—CO—OR$^a$, ix) —(C$_{0-4}$alkyl)-CO—N(R$^a$)(R$^b$), x) —S(O)$_{0-2}$R$^a$, xi) —SO$_2$N(R$^a$)(R$^b$), xii) —NR$^a$SO$_2$R$^a$, xiii) —C$_{1-10}$alkyl, and xiv) —C$_{1-10}$alkyl, wherein one or more of the alkyl carbons can be replaced by a —NR$^a$—, —O—, —S(O)$_{1-2}$—, —O—C(O)—, —C(O)—O—, —C(O)—N(R$^a$)—, —N(R$^a$)—C(O)—, —N(R$^a$)—C(O)—N(R$^a$)—, —C(O)—, —CH(OH)—, —C=C—, or —C≡C; or when R$^6$ and R$^7$ are present on adjacent carbon atoms, R$^6$ and R$^7$, together with the ring to which they are attached, may form a bicyclic aromatic ring selected from naphthyl, indolyl, quinolinyl, isoquinolinyl, quinoxalinyl, benzofuryl, benzothienyl, benzoxazolyl, benzothiazolyl, and benzimidazolyl, any aromatic ring of which is optionally substituted with 1-4 independent substituents selected from i) halogen, ii) —CN, iii) —NO$_2$, iv) —CHO, v) —O—C$_{1-4}$alkyl, vi) —N(C$_{0-4}$alkyl)(C$_{0-4}$alkyl), vii) —C$_{0-4}$alkyl-CO—O(C$_{0-4}$alkyl), viii) —(C$_{0-4}$alkyl)-NH—CO—O(C$_{0-4}$alkyl), ix) —(C$_{0-4}$alkyl)-CO—N(C$_{0-4}$alkyl)(C$_{0-4}$alkyl), x) —S(C$_{0-4}$alkyl), xi) —S(O)(C$_{1-4}$alkyl), xii) —SO$_2$(C$_{0-4}$alkyl), xiii) —SO$_2$N(C$_{0-4}$alkyl)(C$_{0-4}$alkyl), xiv) —NHSO$_2$(C$_{0-4}$alkyl)(C$_{0-4}$alkyl), xv) —C$_{1-10}$alkyl and xvi) —C$_{1-10}$alkyl in which one or more of the carbons can be replaced by a —N(C$_{0-6}$alkyl)-, —O—, —S(O)$_{1-2}$—, —O—C(O)—, —C(O)—O—, —C(O)—N(C$_{0-6}$alkyl)-, —N(C$_{0-6}$alkyl)-C(O)—, —N(C$_{0-6}$alkyl)-C(O)—N(C$_{0-6}$alkyl)-, —C(O)—, —CH(OH)—, —C=C—, or —C≡C—; with the proviso that R$^1$, R$^3$ and R$^6$ are Not hydrogen at the same time.

2. The compound according to claim 1 represented by Formula (I), or a pharmaceutically acceptable salt thereof.

3. The compound according to claim 2, or a pharmaceutically acceptable salt thereof, wherein
R$^6$ is other than H and is attached at the ortho position.

4. The compound according to claim 1 represented by Formula (II), or a pharmaceutically acceptable salt thereof.

5. The compound according to claim 4, or a pharmaceutically acceptable salt thereof, wherein
R$^6$ is other than H and is attached at the ortho position.

6. The compound according to claim 1 represented by Formula (III), or a pharmaceutically acceptable salt thereof.

7. The compound according to claim 6, or a pharmaceutically acceptable salt thereof, wherein
HET is

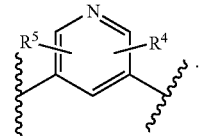

8. The compound according to claim 6, or a pharmaceutically acceptable salt thereof, wherein
HET is

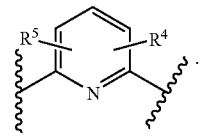

9. The compound according to claim 6, or a pharmaceutically acceptable salt thereof, wherein
HET is

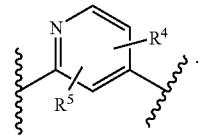

10. The compound according to claim 6 or a pharmaceutically acceptable salt thereof, wherein
HET is

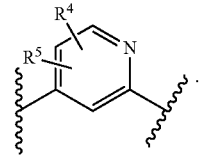

11. The compound according to claim 6, or a pharmaceutically acceptable salt thereof, wherein
HET is

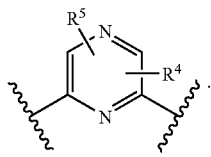

12. The compound according to claim 6, or a pharmaceutically acceptable salt thereof, wherein
$R^6$ is other than H and is attached at the ortho position.

13. The compound according to claim 1 represented by Formula (IV), or a pharmaceutically acceptable salt thereof.

14. The compound according to claim 13, or a pharmaceutically acceptable salt thereof, wherein
HET is

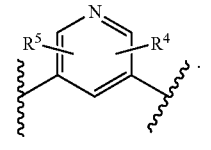

15. The compound according to claim 13, or a pharmaceutically acceptable salt thereof, wherein
HET is

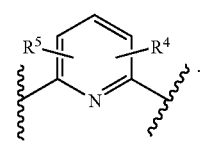

16. The compound according to claim 13, or a pharmaceutically acceptable salt thereof, wherein
HET is

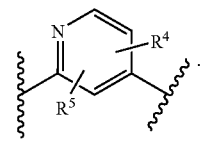

17. The compound according to claim 13, or a pharmaceutically acceptable salt thereof, wherein
HET is

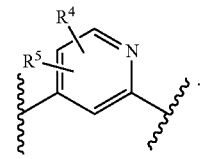

18. The compound according to claim 13, or a pharmaceutically acceptable salt thereof, wherein
HET is

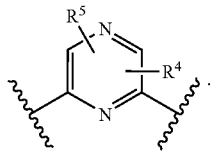

19. The compound according to claim 13, or a pharmaceutically acceptable salt thereof, wherein
$R^6$ is other than H and is attached at the ortho position.

20. A compound represented by

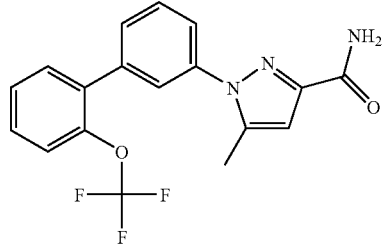

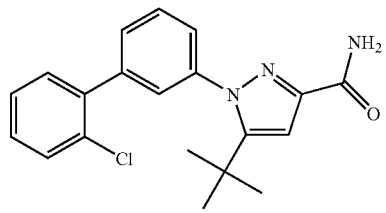

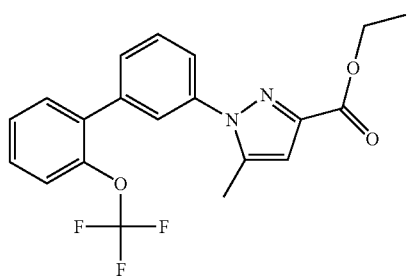

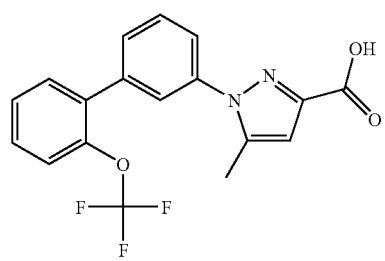

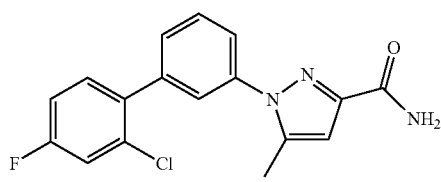

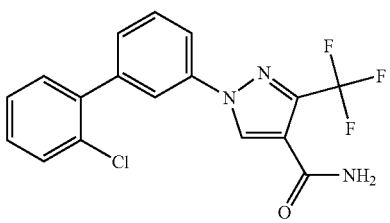

or a pharmaceutically acceptable salt thereof.

21. The compound according to claim 1 represented by

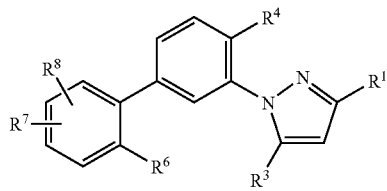

as indicated by the compound number herein:

| Compd | R⁸ | R⁷ | R⁶ | R⁴ | R³ | R¹ |
|---|---|---|---|---|---|---|
| 1 | H | H | CF₃ | H | H | CH₃ |
| 2 | H | H | OCF₃ | H | H | CH₃ |
| 3 | H | H | OCF₃ | H | CH₃ | H |
| 4 | H | H | CF₃ | H | CH₃ | H |
| 5 | H | H | CF₃ | H | CH₃ | CH₃ |
| 6 | H | H | OCF₃ | H | CH₃ | CH₃ |
| 7 | H | H | Cl | H | H | CF₃ |
| 8 | H | H | Cl | H | CH₃ | CONH₂ |
| 9 | H | H | CF₃ | H | CH₃ | CONH₂ |
| 10 | H | H | CF₃ | H | CH₃ | COOCH₃ |
| 11 | H | H | CF₃ | H | CH₃ | COOH |
| 12 | H | H | Cl | H | t-Bu | COOH |
| 13 | H | H | OCF₃ | H | CH₃ | COOCH₃ |
| 14 | H | H | OCF₃ | H | CH₃ | CONH₂ |
| 15 | H | H | OCF₃ | H | CH₃ | COOH |
| 16 | H | H | OCF₃ | H | COOEt | CH₃ |
| 17 | H | H | CF₃ | H | COOEt | CH₃ |
| 18 | H | H | OCF₃ | H | COOH | CH₃ |
| 19 | H | H | CF₃ | H | COOH | CH₃ |
| 20 | H | H | OH | H | CH₃ | CONH₂ |
| 21 | H | H | 0-Ph | H | CH₃ | COOH |
| 22 | H | H | 0-Ph | H | CH₃ | COOMe |
| 23 | H | H | 0-Ph | H | CH₃ | COOEt |
| 24 | H | H | 0-Ph | H | CH₃ | CONH₂ |
| 25 | H | H | CHO | H | CH₃ | CONH₂ |
| 26 | H | 4-Cl | Cl | H | CH₃ | CONH₂ |
| 27 | H | 4-CF₃ | H | H | CH₃ | CONH₂ |
| 28 | H | 3-CF₃ | H | H | CH₃ | CONH₂ |
| 29 | 5-Cl | 3-Cl | H | H | CH₃ | CONH₂ |
| 30 | H | 3-F | H | H | CH₃ | CONH₂ |
| 31 | 5-CF₃ | 3-CF₃ | H | H | CH₃ | CONH₂ |
| 32 | 4-F | 3-Cl | H | H | CH₃ | CONH₂ |
| 33 | H | 4-Cl | H | H | CH₃ | CONH₂ |
| 34 | H | 4-F | H | H | CH₃ | CONH₂ |
| 35 | 4-Cl | 3-Cl | H | H | CH₃ | CONH₂ |
| 36 | H | 3-OCH₃ | OCH₃ | H | CH₃ | CONH₂ |
| 37 | H | 3-Cl | CH₃ | H | CH₃ | CONH₂ |
| 38 | H | 5-Cl | OCH₃ | H | CH₃ | CONH₂ |
| 39 | H | H | (tetrazol-5-yl) | H | CH₃ | CONH₂ |
| 40 | H | 3-(pyrazol-1-yl) | H | H | CH₃ | CONH₂ |
| 41 | H | 3-Ph | H | H | CH₃ | CONH₂ |
| 42 | H | H | (1-(2-oxopiperidin-4-one-ethyl)) | H | CH₃ | CONH₂ |
| 43 | H | 4-CH₂OH | H | H | CH₃ | CONH₂ |
| 44 | H | H | H | H | CH₃ | CONH₂ |
| 45 | H | H | CH₃ | H | CH₃ | CONH₂ |
| 46 | H | 3-COOH | CH₃ | H | CH₃ | CONH₂ |
| 47 | H | 3-F | CH₃ | H | CH₃ | CONH₂ |
| 48 | H | 4-OPh | H | H | CH₃ | CONH₂ |
| 49 | H | 3-Cl | H | H | CH₃ | CONH₂ |
| 50 | H | 3-OEt | H | H | CH₃ | CONH₂ |
| 51 | H | H | F | H | CH₃ | CONH₂ |
| 52 | H | 4-OEt | H | H | CH₃ | CONH₂ |
| 53 | H | 6-F | F | H | CH₃ | CONH₂ |
| 54 | H | 6-CH₃ | CH₃ | H | CH₃ | CONH₂ |
| 55 | H | 4-t-Bu | H | H | CH₃ | CONH₂ |
| 56 | H | 4-OCF₃ | H | H | CH₃ | CONH₂ |
| 57 | H | 4-COCH₃ | H | H | CH₃ | CONH₂ |
| 58 | H | 3-COCH₃ | H | H | CH₃ | CONH₂ |
| 59 | H | 3-CH₃ | CH₃ | H | CH₃ | CONH₂ |
| 60 | H | 4-COOH | H | H | CH₃ | CONH₂ |
| 61 | H | 4-CHO | H | H | CH₃ | CONH₂ |
| 62 | H | 4-CF₃ | CF₃ | H | CH₃ | CONH₂ |
| 63 | H | 6-CF₃ | CF₃ | H | CH₃ | CONH₂ |
| 64 | H | 6-F | CF₃ | H | CH₃ | CONH₂ |
| 65 | H | 5-F | CF₃ | H | CH₃ | CONH₂ |
| 66 | H | 4-Cl | CF₃ | H | CH₃ | CONH₂ |
| 67 | H | 3-Cl | Cl | H | CH₃ | CONH₂ |
| 68 | H | H | OCH₂CF₃ | H | CH₃ | CONH₂ |
| 69 | H | H | OCF₃ | F | CH₃ | COOEt |
| 70 | H | H | OCF₃ | F | CH₃ | CONH₂ |
| 71 | H | H | OCF₃ | F | COOEt | CH₃ |
| 72 | H | H | OCF₃ | F | CONH₂ | CH₃ |
| 73 | H | 3-Cl | Cl | F | CH₃ | CONH₂ |
| 74 | H | 4-CF₃ | CF₃ | F | CH₃ | CONH₂ |
| 75 | H | H | OCF₃ | F | CH₃ | COOH |
| 76 | H | 5-F | OH | H | CH₃ | CONH₂ |
| 77 | H | 5-NMe₂ | OCF₃ | H | CH₃ | CONH₂ |
| 78 | H | 4-F | CF₃ | H | CH₃ | COOH |
| 79 | H | 4-CF₃ | CF₃ | H | CH₃ | COOH |
| 80 | H | 4-CF₃ | F | H | CH₃ | COOH |
| 81 | H | 3-CF₃ | CF₃ | H | CH₃ | COOH |
| 82 | H | H | OCF₃ | H | CH₃ | CF₃ |
| 83 | H | H | OCF₃ | H | t-Bu | CONH₂ |
| 84 | H | H | OCF₃ | H | OCH₂CH₃ | CH₃ |
| 85 | H | 5-F | CF₃ | H | CH₃ | COOH |
| 86 | H | 3-Cl | Cl | H | CH₃ | COOH |
| 87 | H | 4-Cl | CF₃ | H | CH₃ | COOH |
| 88 | H | 3-Cl | Cl | F | CH₃ | COOH |
| 89 | H | 6-Cl | Cl | H | CH₃ | COOH |
| 90 | H | 6-Cl | Cl | H | CH₃ | CONH₂ |
| 91 | H | 6-F | CF₃ | H | CH₃ | COOH |
| 92 | H | H | CF₃ | H | CH₃ | COOH |
| 93 | H | 6-CF₃ | CF₃ | H | CH₃ | COOH |
| 94 | H | 6-Cl | CF₃ | H | CH₃ | CONH₂ | or a pharmaceutically acceptable salt thereof.

22. The compound of claim 1 represented by
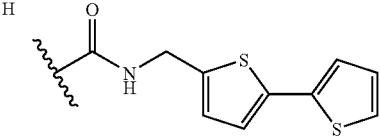
as represented by the compound number below:
| Compd | R⁶ | R³ | R² | R¹ |
|---|---|---|---|---|
| 1 | Cl | H | CONH-t-Bu | H |
| 2 | Cl | H | CONH-Me | H |
| 3 | Cl | H | 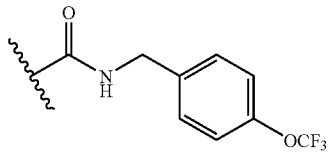 | H |
| 4 | Cl | H | 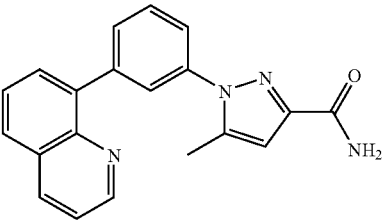 | H |
| 5 | CF₃ | H | COOEt | NH₂ |
| 6 | CF₃ | H | COOH | H |
| 7 | OCF₃ | H | COOEt | H |
| 8 | OCF₃ | H | COOH | NH₂ |
or a pharmaceutically acceptable salt thereof.
23. A compound represented by
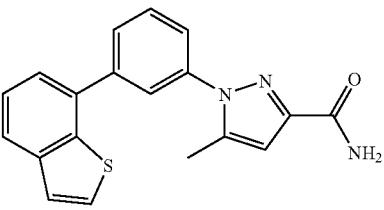
-continued
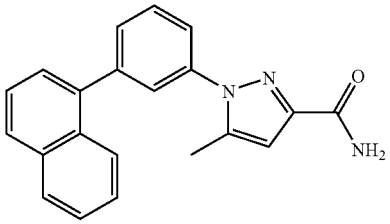
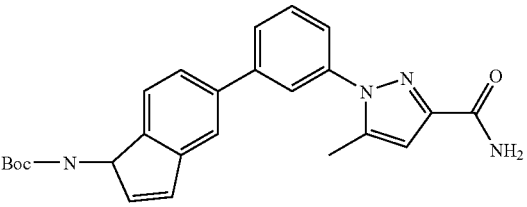
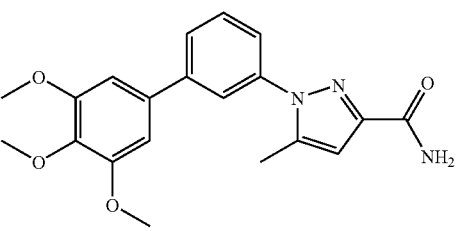

-continued
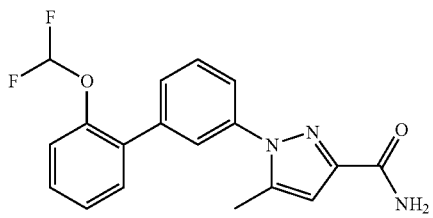
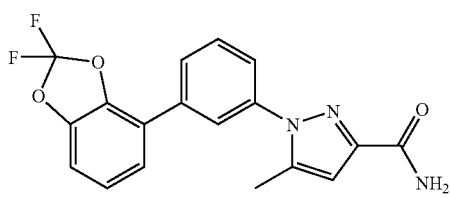
or a pharmaceutically acceptable salt thereof.
24. A compound represented by
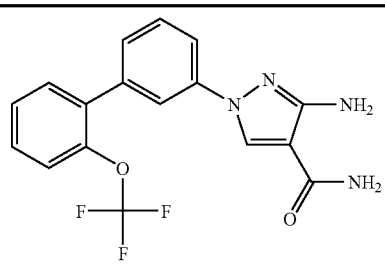
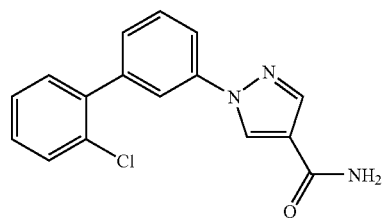
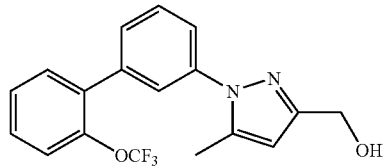
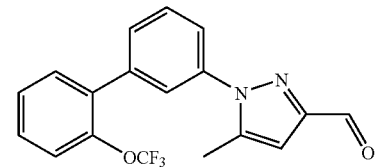
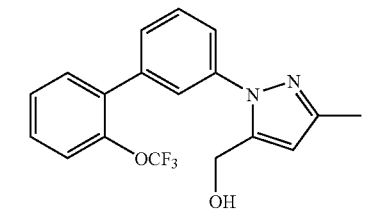
-continued
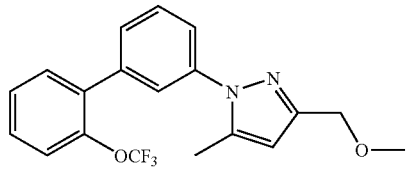
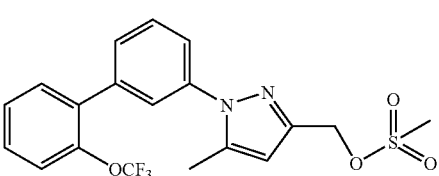
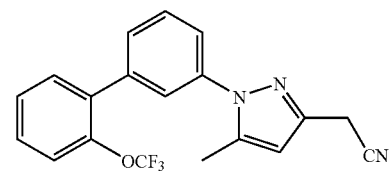
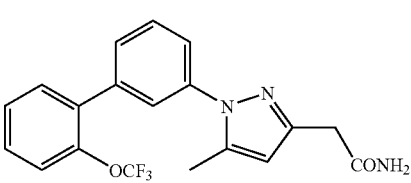
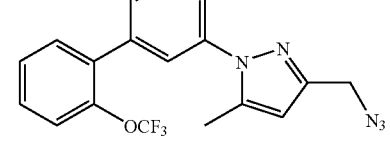
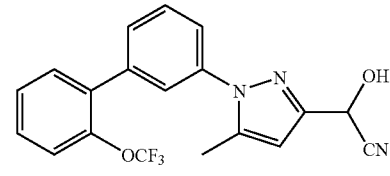
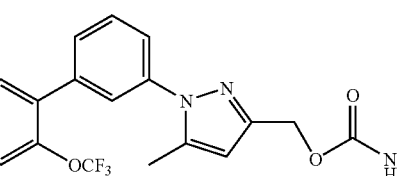
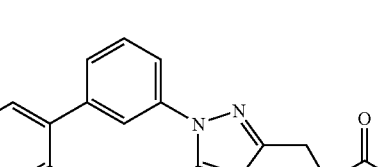
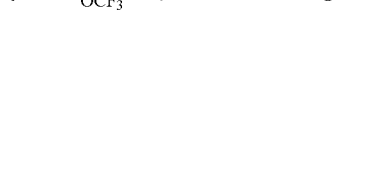

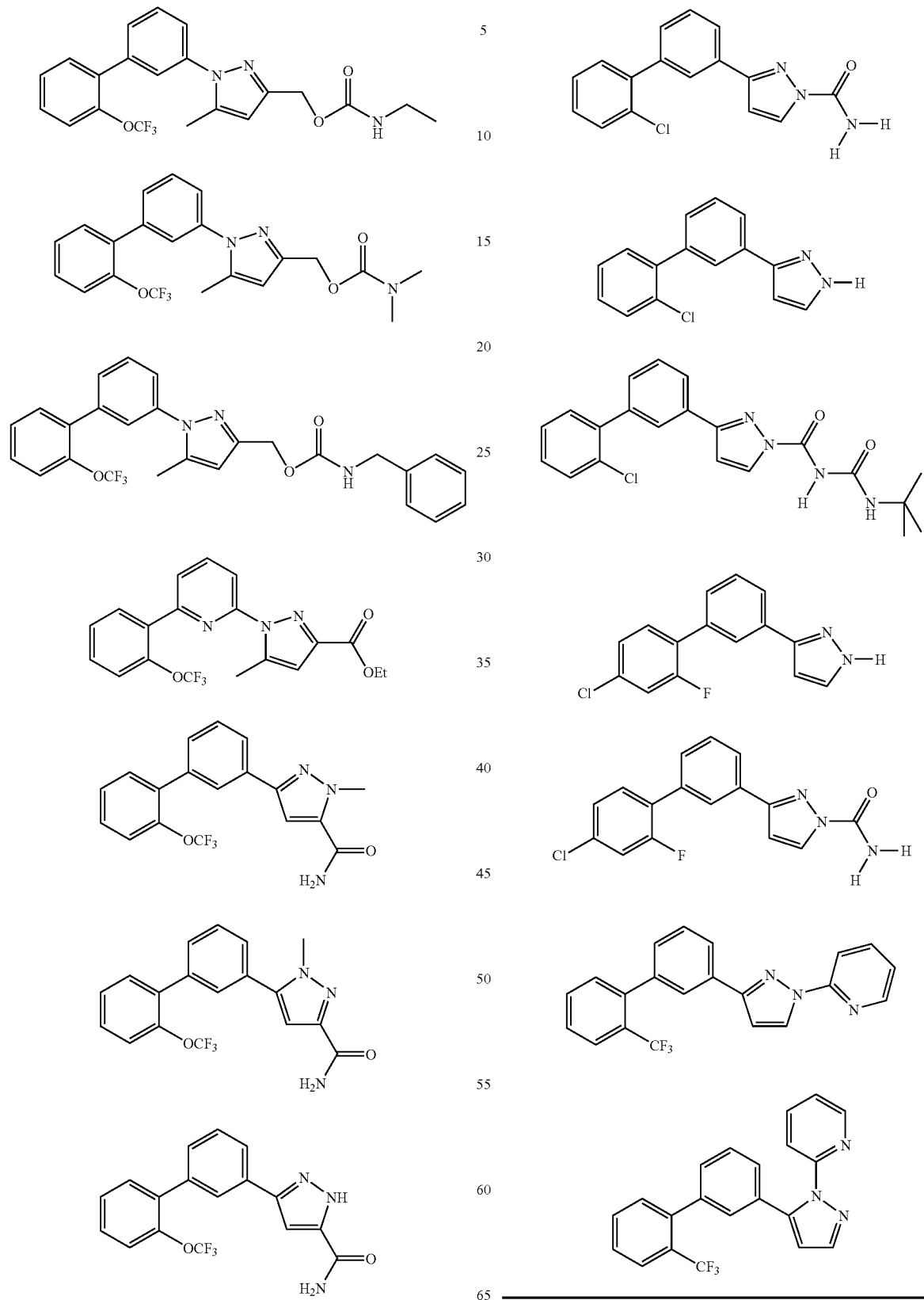
or a pharmaceutically acceptable salt thereof.

25. A compound represented by
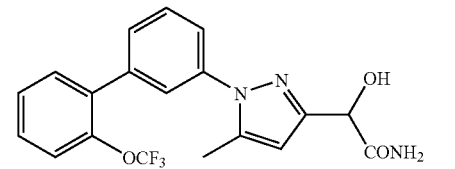
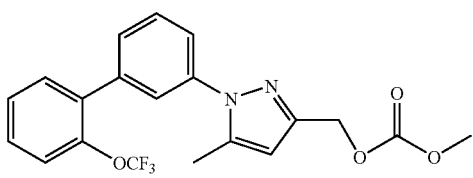
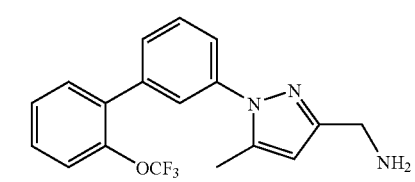
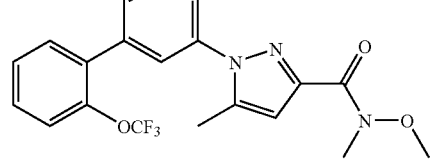
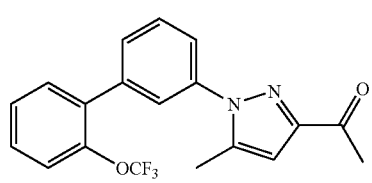
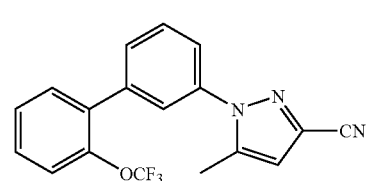
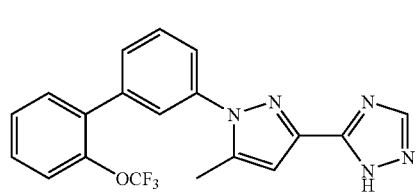
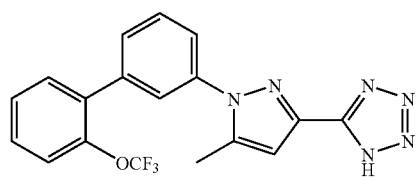
-continued
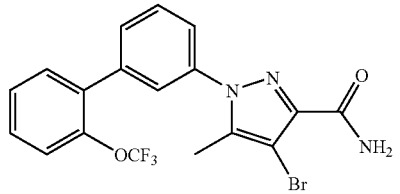
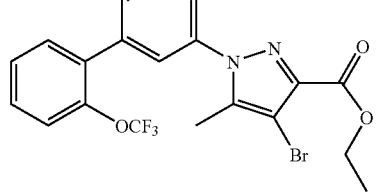
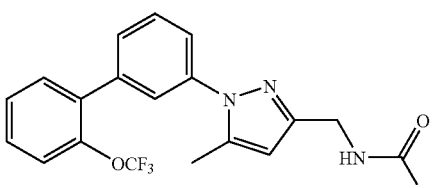
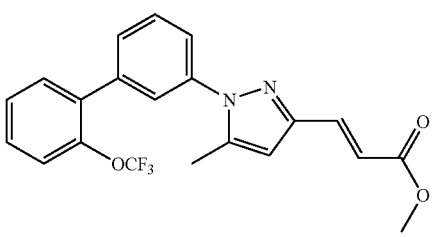
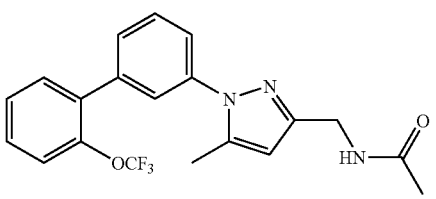
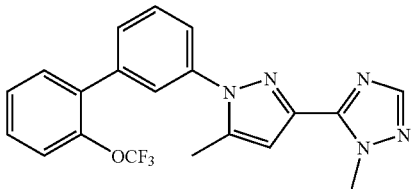
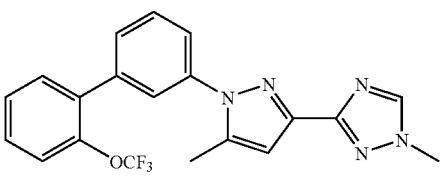

-continued

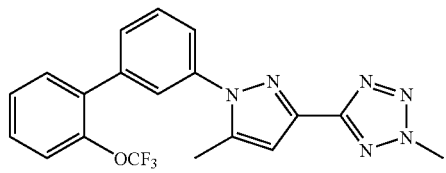

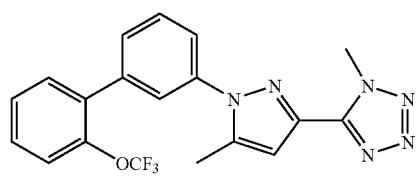

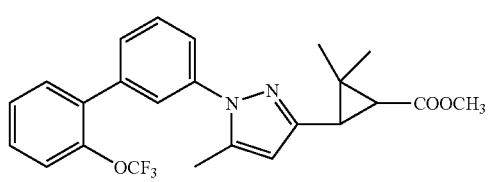

or a pharmaceutically acceptable salt thereof.

26. The compound of claim 1 is represented by

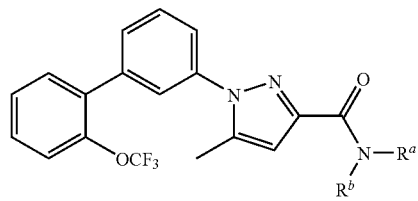

as represented by the compound number below:

| Compound | $R^a$ | $R^b$ |
|---|---|---|
| 1 | —CH$_2$CH$_2$OH | H |
| 2 | —CH$_2$CH$_2$CH$_2$OH | H |
| 3 | —CH(CH$_2$OH)$_2$ | H |
| 4 | —CH$_3$ | H |
| 5 | —CH$_2$CH$_3$ | H |
| 6 | 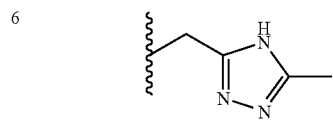 | H |
| 7 | 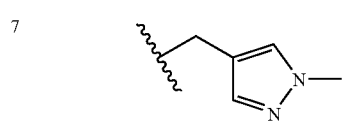 | H |
| 8 | 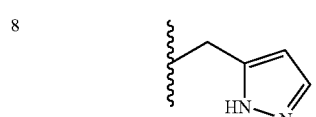 | H |
| 9 | 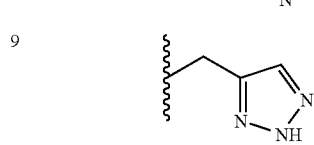 | H |

-continued

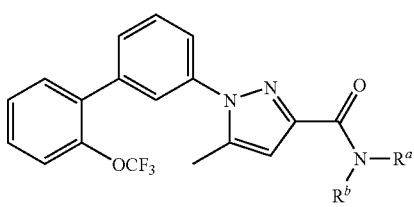

as represented by the compound number below:

| Compound | $R^a$ | $R^b$ |
|---|---|---|
| 10 | 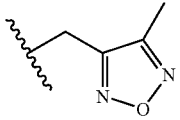 | H |
| 11 | 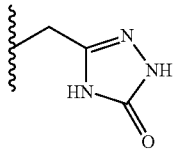 | CH$_3$ |
| 12 | 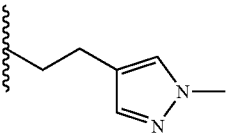 | CH$_3$ |
| 13 | 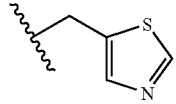 | H | or a pharmaceutically acceptable salt thereof.

27. A compound represented by

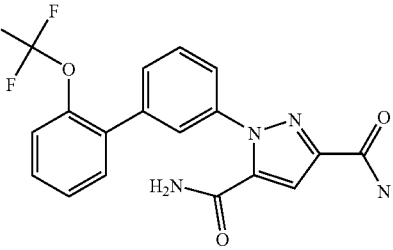

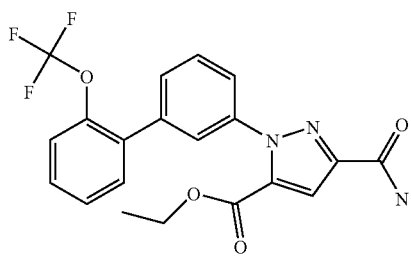

-continued
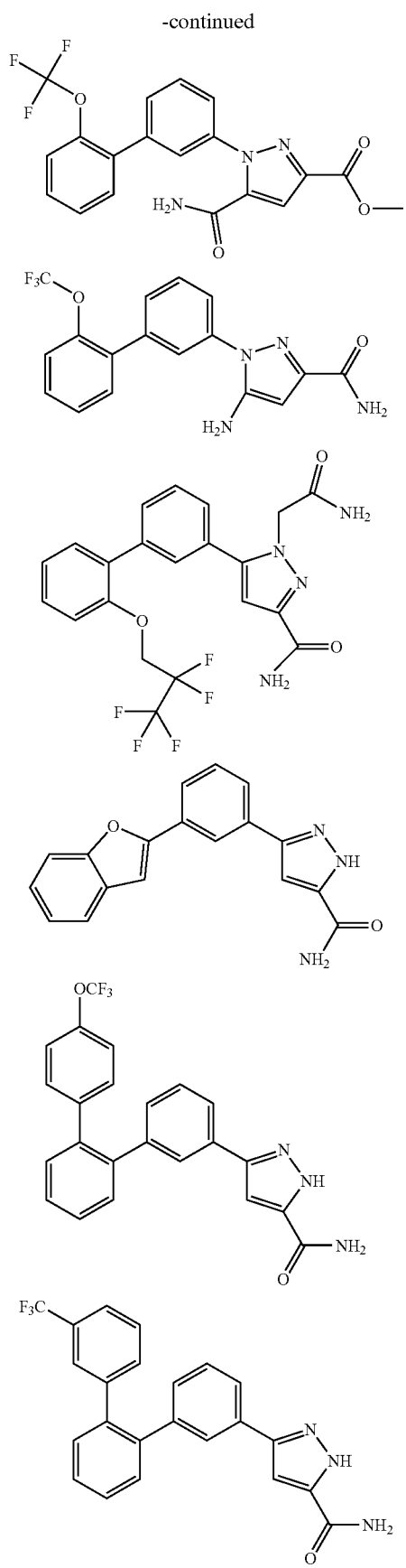
-continued
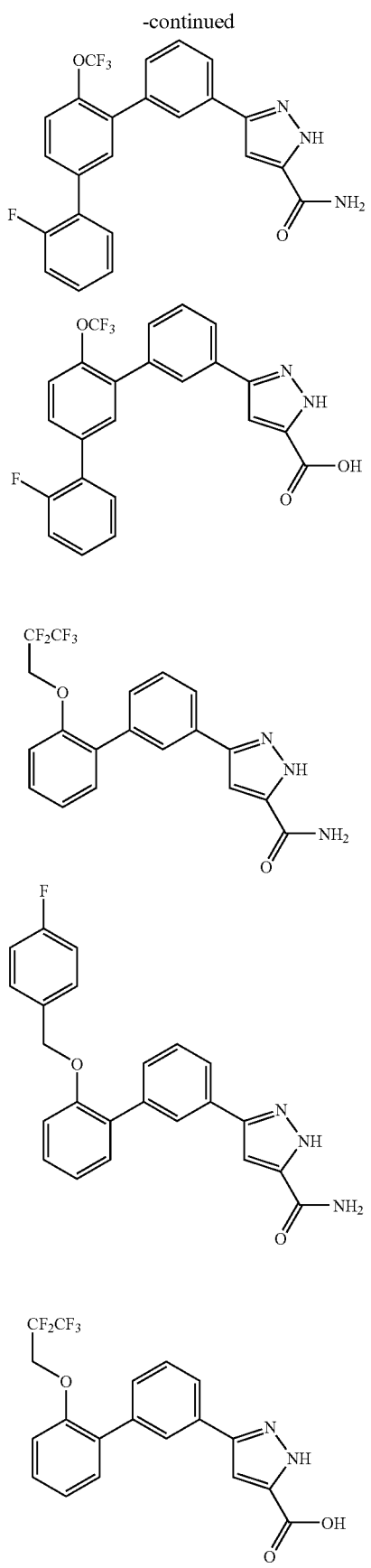

-continued

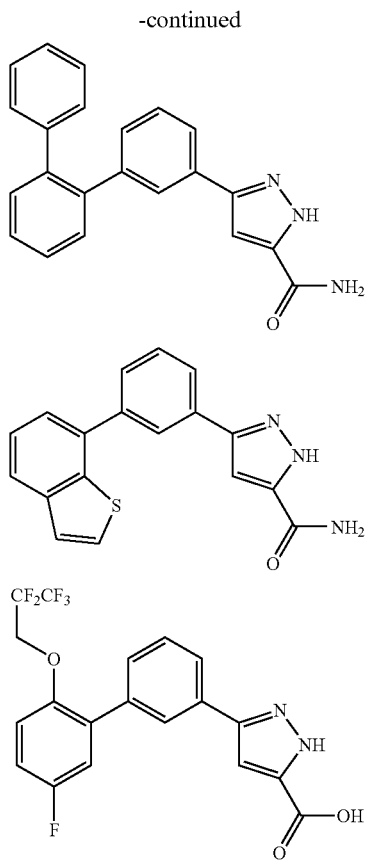

-continued

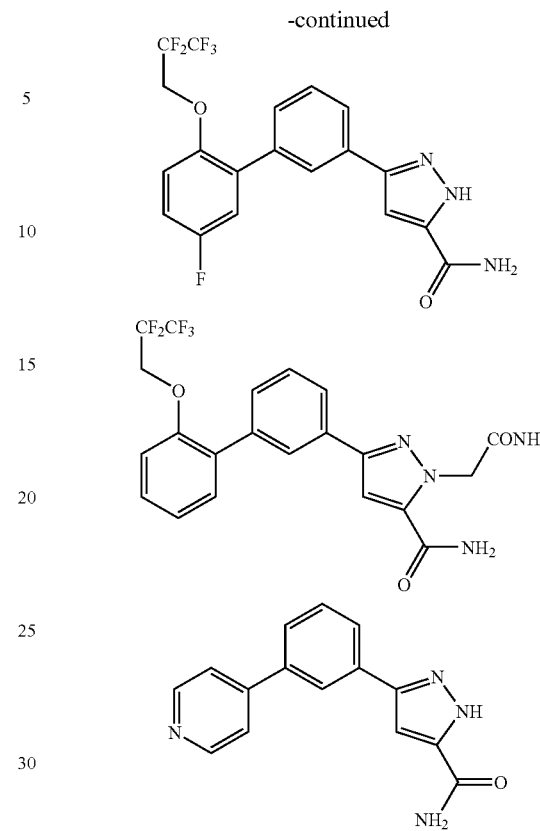

or a pharmaceutically acceptable salt thereof.

28. The compound of claim 1 represented by as represented by the compound number below:

| Compd | R$^7$ | R$^6$ | R$^4$ | R$^3$ | R$^2$ | R$^1$ |
|---|---|---|---|---|---|---|
| 1 | H | CF$_3$ | H | CONH$_2$ | H | CONH$_2$ |
| 2 | H | OCF$_3$ | H | CONH$_2$ | H | CONH$_2$ |
| 3 | 4-CF$_3$ | CF$_3$ | H | CONH$_2$ | H | CONH$_2$ |
| 4 | 5-F | CF$_3$ | H | CONH$_2$ | H | CONH$_2$ |
| 5 | 5-CF$_3$ | OCF$_3$ | H | CONH$_2$ | H | CONH$_2$ |
| 6 | H | OCHF$_2$ | H | CONH$_2$ | H | CONH$_2$ |
| 7 | 5-CF$_3$ | CF$_3$ | H | CONH$_2$ | H | CONH$_2$ |
| 8 | 6-F | CF$_3$ | H | CONH$_2$ | H | CONH$_2$ |
| 9 | 4-F | OCH$_2$CF$_3$CF$_3$ | H | CONH$_2$ | H | CONH$_2$ |
| 10 | 6-CF$_3$ | CF$_3$ | H | CONH$_2$ | H | CONH$_2$ |
| 11 | H | OCH(CH$_3$)$_2$ | H | CONH$_2$ | H | CONH$_2$ |
| 12 | 3-OCF$_3$ | OCH$_2$CF$_3$CF$_3$ | H | CONH$_2$ | H | CONH$_2$ |
| 13 | 3-CF$_3$ | OCH$_2$CF$_3$CF$_3$ | H | CONH$_2$ | H | CONH$_2$ |
| 14 | 5-F | OCH$_2$CF$_3$CF$_3$ | H | CONH$_2$ | H | CONH$_2$ |
| 15 | 5-F | OCF$_3$ | H | CONH$_2$ | H | CONH$_2$ |
| 16 | 4-F | CF$_3$ | H | CONH$_2$ | H | CONH$_2$ |
| 17 | H | CF$_3$ | H | CONH-Et | H | CONH-Et |
| 18 | H | CF$_3$ | H | CONH$_2$ | H | CONH-Et |
| 19 | H | OCF$_3$ | 4-F | CONH$_2$ | H | CONH$_2$ |
| 20 | H | OCF$_3$ | H | CONH-Et | H | CONH$_2$ |
| 21 | H | OCF$_3$ | H | COOEt | H | COOEt |
| 22 | H | CF$_3$ | H | COOEt | H | COOEt |

-continued

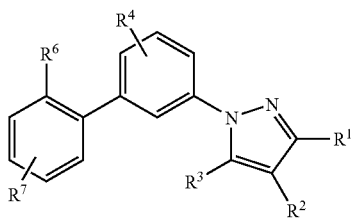

as represented by the compound number below:

| Compd | R⁷ | R⁶ | R⁴ | R³ | R² | R¹ |
|---|---|---|---|---|---|---|
| 23 | H | OCF₃ | H | COOEt | H | CONH₂ |
| 24 | H | CF₃ | H | COOEt | H | CONH₂ |
| 25 | 4-CF₃ | CF₃ | H | COOEt | H | CONH₂ |
| 26 | 4-CF₃ | CF₃ | H | CONH₂ | H | COOEt |
| 27 | H | OCF₃ | H | CONH₂ | H | COOEt |
| 28 | H | CF₃ | H | CONH₂ | H | COOEt |
| 29 | H | OCF₃ | 4-F | COOH | H | COOEt |
| 30 | H | OCF₃ | 4-F | COOH | H | CONH₂ |
| 31 | H | OCF₃ | 4-F | CONH₂ | H | COOEt |
| 32 | H | OCF₃ | H | COOH | H | CONH₂ |
| 33 | H | OCF₃ | H | CH₃ | COOMe | COOEt |
| 34 | H | OCF₃ | H | CH₃ | COOH | COOH |
| 35 | 4-CF₃ | CF₃ | H | CH₃ | COOH | COOH |
| 36 | H | OCF₃ | H | CH₃ | CONH₂ | CONH₂ |
| 37 | 4-CF₃ | CF₃ | H | CH₃ | CONH₂ | CONH₂ |
| 38 | H | CF₃ | H | CH₃ | COOH | COOH |
| 39 | H | CF₃ | H | CH₃ | CONH₂ | CONH₂ |
| 40 | 5-CF₃ | CF₃ | H | CH₃ | CONH₂ | CONH₂ |
| 41 | 5-CF₃ | CF₃ | H | CH₃ | COOH | COOH |
| 42 | H | CF₃ | 4-OCF₃ | CH₃ | COOMe | COOH |
| 43 | H | OCF₃ | 4-OCF₃ | CH₃ | CONH₂ | CONH₂ |
| 44 | H | CF₃ | 4-OCF₃ | CH₃ | CONH₂ | CONH₂ |
| 45 | H | OCF₃ | 4-F | CH₃ | COOEt | COOEt |
| 46 | H | CF₃ | 4-F | CH₃ | COOEt | COOEt |
| 47 | H | OCF₃ | 4-F | CH₃ | COOEt | CONH₂ |
| 48 | H | OCF₃ | 4-F | CH₃ | CONH₂ | CONH₂ |
| 49 | H | CF₃ | 4-F | CH₃ | COOEt | CONH₂ |
| 50 | H | CF₃ | 4-F | CH₃ | CONH₂ | CONH₂ |
| 51 | H | OCF₃ | 4-F | CH₃ | COOH | COOH |
| 52 | H | Cl | H | H | CONH—Me | H |
| 53 | H | Cl | H | H | CONH₂ | CF₃ |
| 54 | H | OCF₃ | H | H | COOEt | NH₂ |
| 55 | H | CF₃ | H | H | COOEt | NH₂ |
| 56 | H | OCF₃ | H | H | COOH | H |
| 57 | H | OCF₃ | H | H | COOEt | H |
| 58 | 4-CF₃ | CF₃ | H | H | COOEt | NH₂ |
| 59 | H | OCF₃ | H | H | COOH | NH₂ |
| 60 | H | OCF₃ | H | H | CONH₂ | H |
| 61 | H | OCF₃ | H | H | CONH₂ | NH₂ |
| 62 | H | OCF₃ | H | CH₃ | CONH₂ | CH₃ |
| 63 | H | Cl | H | H | CONH₂ | H | or a pharmaceutically acceptable salt thereof.

29. The compound of claim 1 represented by

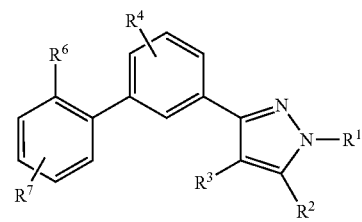

as represented by the compound number below:

| Compd | R⁷ | R⁶ | R⁴ | R³ | R² | R¹ |
|---|---|---|---|---|---|---|
| 1 | H | OCF₃ | H | H | COOCH₃ | H |
| 2 | H | CF₃ | H | NH₂ | CONH₂ | H |
| 3 | H | OCF₃ | H | NH₂ | COOH | H |

-continued

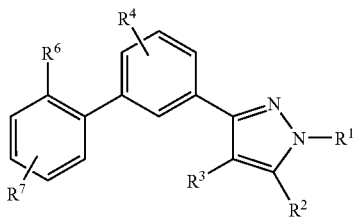

as represented by the compound number below:

| Compd | R⁷ | R⁶ | R⁴ | R³ | R² | R¹ |
|---|---|---|---|---|---|---|
| 4 | H | OCF₃ | H | NH₂ | CONH₂ | H |
| 5 | H | CF₃ | H | NH₂ | COOH | H |
| 6 | H | OCF₃ | H | H | COOEt | H |
| 7 | H | CF₃ | H | H | COOEt | H |
| 8 | H | CF₃ | H | H | CONH₂ | |
| 9 | H | OCF₃ | F | H | COOEt | H |
| 10 | H | OCF₃ | F | H | CONH₂ | H |
| 11 | H | OCF₃ | H | CH₃ | COOEt | H |
| 12 | H | OCF₃ | H | CH₃ | COOH | H |
| 13 | H | OCF₃ | H | CH₃ | CONH₂ | H |
| 14 | H | CF₃ | H | CH₃ | COOH | H |
| 15 | H | CF₃ | H | CH₃ | CONH₂ | H |
| 16 | 4-CF₃ | CF₃ | H | CH₃ | COOH | H |
| 17 | 4-CF₃ | CF₃ | H | CH₃ | CONH₂ | H |
| 18 | H | OCF₃ | F | H | COCH | H |
| 19 | 5-CF₃ | CF₃ | H | H | COOH | H |
| 20 | 5-CF₃ | CF₃ | H | H | CONH₂ | H |
| 21 | H | CF₃ | H | CH₃ | CONH₂ | t-Bu |
| 22 | H | OCF₃ | H | H | COOH | t-Bu |
| 23 | H | OCF₃ | H | H | CONH₂ | t-Bu |
| 24 | 6-F | CF₃ | H | H | CONH₂ | H |
| 25 | 6-F | CF₃ | H | H | COOH | H |
| 26 | 5-F | OCF₃ | H | H | COOH | H |
| 27 | 5-F | OCF₃ | H | H | CONH₂ | H |
| 28 | 4-CF₃ | CF₃ | H | H | CONH₂ | H |
| 29 | H | OCF₃ | H | H | CONHNMe₂ | H | or a pharmaceutically acceptable salt thereof.

30. A pharmaceutical composition comprising a therapeutically effective amount of the compound according to claim 1, or a pharmaceutically acceptable salt thereof, and a pharmaceutically acceptable carrier.

31. The pharmaceutical composition according to claim 27, further comprising a second therapeutic agent selected from the group consisting of: i) opiate agonists, ii) opiate antagonists, iii) calcium channel antagonists, iv) 5HT receptor agonists, v) 5HT receptor antagonists vi) sodium channel antagonists, vii) NMDA receptor agonists, viii) NMDA receptor antagonists, ix) COX-2 selective inhibitors, x) NK1 antagonists, xi) non-steroidal anti-inflammatory drugs, xii) selective serotonin reuptake inhibitors, xiii) selective serotonin and norepinephrine reuptake inhibitors, xiv) tricyclic antidepressant drugs, xv) norepinephrine modulators, xvi) lithium, xvii) valproate, and xviii) neurontin.

* * * * *